(12) United States Patent
Boer et al.

(10) Patent No.: US 11,925,193 B2
(45) Date of Patent: *Mar. 12, 2024

(54) STEVIOL GLYCOSIDE TRANSPORT

(71) Applicant: DSM IP ASSETS B.V., Heerlen (NL)

(72) Inventors: Viktor Marius Boer, Echt (NL);
Priscilla Zwartjens, Echt (NL); Eric Van Den Berg, Echt (NL)

(73) Assignee: DSM IP Assets B.V., Heerlen (NL)

( * ) Notice: Subject to any disclaimer, the term of this patent is extended or adjusted under 35 U.S.C. 154(b) by 121 days.

This patent is subject to a terminal disclaimer.

(21) Appl. No.: 17/512,368

(22) Filed: Oct. 27, 2021

(65) Prior Publication Data

US 2022/0110350 A1    Apr. 14, 2022

Related U.S. Application Data

(62) Division of application No. 15/751,674, filed as application No. PCT/EP2016/069356 on Aug. 15, 2016, now Pat. No. 11,297,862.

(60) Provisional application No. 62/204,702, filed on Aug. 13, 2015.

(51) Int. Cl.
| | |
|---|---|
| C12N 1/16 | (2006.01) |
| A23L 2/60 | (2006.01) |
| A23L 27/30 | (2016.01) |
| C07K 14/39 | (2006.01) |
| C07K 14/395 | (2006.01) |
| C07K 14/40 | (2006.01) |
| C12N 9/24 | (2006.01) |
| C12P 15/00 | (2006.01) |
| C12P 19/56 | (2006.01) |

(52) U.S. Cl.
CPC ............... *A23L 27/36* (2016.08); *A23L 2/60* (2013.01); *C07K 14/39* (2013.01); *C07K 14/395* (2013.01); *C07K 14/40* (2013.01); *C12N 1/16* (2013.01); *C12N 9/2402* (2013.01); *C12P 15/00* (2013.01); *C12P 19/56* (2013.01)

(58) Field of Classification Search
CPC ................................. C12N 9/2405; C12N 1/16
See application file for complete search history.

(56) References Cited

U.S. PATENT DOCUMENTS

| | | | |
|---|---|---|---|
| 11,297,862 B2* | 4/2022 | Boer ..................... | C12P 15/00 |
| 2015/0031868 A1 | 1/2015 | Lehmann et al. | |
| 2016/0153017 A1 | 6/2016 | Van Der Hoeven et al. | |
| 2016/0160257 A1 | 6/2016 | Broers et al. | |
| 2016/0177360 A1 | 6/2016 | Boer et al. | |

FOREIGN PATENT DOCUMENTS

| | | |
|---|---|---|
| CN | 103732753 A | 4/2014 |
| WO | 2004026043 A1 | 4/2004 |
| WO | 2004032648 A1 | 4/2004 |
| WO | 2013110673 A1 | 8/2013 |
| WO | 2014122328 A1 | 8/2014 |
| WO | 2014191581 A2 | 12/2014 |
| WO | 2015/007748 A1 | 1/2015 |
| WO | 2015011209 A1 | 1/2015 |

OTHER PUBLICATIONS

International Search Report issued in counterpart International Application No. PCT/EP2016/069357, dated Nov. 18, 2016.
Dujon et al., "Genome evolution in yeasts" Database, Uniprot: Q6c4M7. (Aug. 16, 2004) p. 1.
Bowie, J.U. et al., "A method to identify protein sequences that fold into a known three-dimensional structure", Science, Jul. 12, 1991, pp. 164-170, vol. 253, No. 5016.
Chothia, Cyrus et al., "The relation between the divergence of sequence and structure in proteins", The EMBO Journal, 1986, pp. 823-826, vol. 5, No. 4.
Ng, Pauline C. et al., "Predicting Deleterious Amino Acid Substitutions", Genome Research, 2001, pp. 863-874, vol. 11.
Henikoff, Steven et al., "Amino acid substitution matrices from protein blocks", Proceedings of the National Academy of Sciences of the United States of America, Nov. 1992, pp. 10915-10919, vol. 89.
Ho, Steffan N. et al., "Site-directed mutagenesis by overlap extension using the polymerase chain reaction", Gene, Apr. 15, 1989, pp. 51-59, vol. 77, No. 1.
Huelsenbeck, John P. et al., "Bayesian analysis of amino acid substitution models", Philosophical Transactions of the Royal Society B, Oct. 7, 2008, Abstract.
Landt, Olfert et al., "A general method for rapid site-directed mutagenesis using the polymerase chain reaction", Gene, 1990, pp. 125-128, vol. 96, No. 1.
Ng, Pauline C. et al., "Predicting the Effects of Amino Acid Substitutions on Protein Function", Annual Review of genomics and Human Genetics, 2006, pp. 61-80, vol. 7.
Taylor, W.R., "Pattern matching methods in protein sequence comparison and structure prediction", Protein Engineering, Design and Selection, Jul. 1988, pp. 77-86, vol. 2, No. 2.
Villoutreix, Bruno, "Mutations or Variations", VLS3D.com, Sep. 15, 2020.

(Continued)

*Primary Examiner* — Tekchand Saidha
(74) *Attorney, Agent, or Firm* — McBee, Moore & Vanik, IP, LLC

(57) ABSTRACT

A recombinant host capable of producing a steviol glycoside which overexpresses a polypeptide which mediates steviol glycoside transport and which polypeptide comprises the amino acid sequence set forth in SEQ ID NO: 29 or an amino acid sequence having at least about 50% sequence identity thereto. A recombinant host capable of producing a steviol glycoside which has been modified, preferably in its genome, to result in a deficiency in the production of a polypeptide which mediates steviol glycoside transport and which polypeptide comprises the amino acid sequence set forth in SEQ ID NO: 29 or an amino acid sequence having at least about 50% sequence identity thereto.

11 Claims, 21 Drawing Sheets
Specification includes a Sequence Listing.

(56) References Cited

OTHER PUBLICATIONS

Muller, Tobias et al., "Estimating Amino Acid Substitution Models: A Comparison of Dayhoff's Estimator, the Resolvent Approach and a Maximum Likelihood Method", Molecular Biology and Evolution, Jan. 2002, pp. 8-13, vol. 19, No. 1.
Kruskal, Joseph, "An Overview of Sequence Comparison: Time Warps, String Edits, and Macromolecules", SIAM Review, Apr. 1983, p. 201, vol. 25, No. 2.
Guo, H., et al., "Protein to Random Amino Acid Change," PNAS (2004), vol. 101, No. 21: 9205-9210.
Mottram, Donal S., et al., "Acrylamide is formed in the Maillard reaction," Nature, (2002), vol. 419, 448-449.
Tareke, E. et al., "Acrylamide: A Cooking Carcinogen?", Chemical Research in Toxicity, (2000), vol. 13, 517-522.
Wang, et al., "Pathway mining-based integration of critical enzyme parts for de novo biosynthesis of steviolglycosides sweetener in *Escherichia coli*," Cell Research, v. 26: pp. 258-261 (Sep. 11, 2015).

\* cited by examiner pHYPO-KAH/HYG-R PCR product
4614 bp

SEQUENCE LISTING

<160> NUMBER OF SEQ ID NOS: 34

<210> SEQ ID NO 1
<211> LENGTH: 1422
<212> TYPE: DNA
<213> ORGANISM: Artificial sequence
<220> FEATURE:
<223> OTHER INFORMATION: UGT2_1a CpO for Y. lipolitica

<400> SEQUENCE: 1

```
atggccacct ccgactccat tgtcgacgac cgaaagcagc tgcacgttgc caccttcccc      60
tggctcgcct tggccacat tctgccctac ctccagctct ccaagctcat tgctgagaag     120
ggccacaagg tttctttcct gtccaccacc cgaaacatcc agcgactctc ctcccacatc     180
tctcctctca tcaacgttgt ccagctcacc ctcccccgag tccaggagct ccccgaggat     240
gccgaggcca ccactgatgt ccaccccgag acatcccct acctcaagaa ggcctccgac     300
ggtctgcagc ccgaggtcac ccgattcctc gagcagcact ctcccgactg gatcatctac     360
gactacaccc actactggct cccctccatt gctgcttctc tcggtatctc tcgagcccac     420
ttctccgtca ccaccccctg ggccattgct acatgggcc cctctgctga cgccatgatc     480
aacggttccg acgccgaac caccgtcgag gatctcacca cccctcccaa gtggttcccc     540
ttccccacca aggtctgctg gcgaaagcac gatctcgccc gactcgtccc ctacaaggcc     600
cccggtatct ccgacggtta ccgaatgggg ctggttctca agggctccga ctgtctgctc     660
tccaagtgct accacgagtt tggtacccag tggctccccc tgctcgagac tctgcaccag     720
gtccccgttg tccccgtcgg tctgctccct ccgagatcc ccggtgacga aggacgag      780 acttgggttt ccatcaagaa gtggctcgac ggcaagcaga agggctccgt cgtctacgtt     840
gctctcggct ccgaggttct tgtctcccag actgaggtcg tcgagctcgc cctcggtctg     900
gagctctccg gtctgccctt cgtctgggcc taccgaaagc ccaagggtcc cgccaagtcc     960
gactccgtcg agctccccga cggtttcgtc gagcgaactc gagatcgagg tctggtctgg    1020
acctcttggg ctccccagct ccgaatcctc tcccacgagt ccgtctgcgg tttcctgacc    1080
cactgtggtt ccggctccat tgtcgagggc ctcatgttcg ccaccccct catcatgctg    1140 cccatcttcg gtgaccagcc cctcaacgcc cgactcctcg aggacaagca ggtcggtatc    1200
```

```
gagatccccc gaaacgaaga ggacggctgc ctcaccaagg agtctgttgc ccgatctctg    1260
cgatctgttg ttgtcgagaa agagggtgag atctacaagg ccaacgcccg agagctctcc    1320
aagatctaca acgacaccaa ggtcgagaag gagtacgttt cccagtttgt cgactacctc    1380
gagaagaacg cccgagctgt cgccattgac cacgagagtt aa                      1422

<210> SEQ ID NO 2
<211> LENGTH: 803
<212> TYPE: DNA
<213> ORGANISM: Yarrowia lipolytica

<400> SEQUENCE: 2
taccaaccac agattacgac ccattcgcag tcacagttca ctagggtttg ggttgcatcc      60
gttgagagtg gtttgttttt aaccttctcc atgtgctcac tcaggttttg ggttcagatc     120
aaatcaaggc gtgaaccact gtttgaggac aaatgtgaca caaccaacca gtgtcagggg     180
caagtccgtg acaaggggga agatacaatg caattactga cagttacgga ctgcctcgat     240
gccctaacct tgccccaaaa taagacaact gtcctcgttt aagcgcaacc ctattcagcg     300
tcacgtcata atagcgtttg gatagcacta gtctatgagg agcgttttat gttgcggtga     360
gggcgattgg tgctcatatg ggttcaattg aggtggtgga acgagcttag tcttcaattg     420
aggtgcgagc gacacaattg ggtgtcacgt ggcctaattg acctcggatc gtggagtccc     480
cagttataca gcaaccacga ggtgcatgag taggagacgt caccagacaa tagggttttt     540
ttggactgga gagggtaggg caaaagcgct caacgggctg tttggggagc tatggggag      600 gaattggcga tatttgtgag gttgacggct ccgatttgcg tgttttgtcg cttctgcatc     660
tccccatacc catatcttcc ctccccacct ctttccacga taattttacg gatcagcaat     720
aaggttcctt ctcctagttt ccacgtccat atatatctat gctgcgtcgt ccttttcgtg     780
acatcaccaa aacacataca aaa                                             803

<210> SEQ ID NO 3
<211> LENGTH: 995
<212> TYPE: DNA
<213> ORGANISM: Yarrowia lipolytica

<400> SEQUENCE: 3
ctgtacctgc tgtggaccac gcacggcgga acgtaccgta caaatatttt cttgctcaca      60
tgactctctc tcggccgcgc acgccggtgg caaattgctc ttgcattggc tctgtctcta     120
gacgtccaaa ccgtccaaag tggcaggggtg acgtgatgcg acgcacgaag gagatggccc    180
ggtggcgagg aaccggacac ggcgagccgg cgggaaaaaa ggcggaaaac gaaaagcgaa     240
gggcacaatc tgacggtgcg gctgccacca acccaaggag gctatttggg gtcgctttcc     300
atttcacatt cgccctcaat ggccactttg cggtggtgaa catggtttct gaaacaaccc     360
cccagaatta gagtatattg atgtgtttaa gattgggttg ctatttggcc attgtggggg     420 aggggtagcga cgtggaggac attccagggc gaattgagcc tagaaagtgg taccattcca    480
accgtctcag tcgtccgaat tgatcgctat aactatcacc tctctcacat gtctacttcc     540
ccaaccaaca tccccaacct cccccacact aaagttcacg ccaataatgt aggcactctt     600
tctgggtgtg ggacagcaga gcaatacgga ggggagatta cacaacgagc cacaattggg    660
gagatggtag ccatctcact cgacccgtcg acttttggca acgctcaatt acccaccaaa    720
tttgggctgg agttgagggg accgtgttcc agcgctgtag gaccagcaac acacacggta    780
```

| | |
|---|---|
| tcaacagcaa ccaacgcccc cgctaatgca cccagtactg cgcaggtgtg ggccaggtgc | 840 |
| gttccagatg cgagttggcg aaccctaagc cgacagtgta cttttttggga cgggcagtag | 900 |
| caatcgtggg cggagacccc ggtgtatata aaggggtgga gaggacggat tattagcacc | 960 |
| aacacacaca cttatactac atgctagcca caaaa | 995 |

<210> SEQ ID NO 4
<211> LENGTH: 1004
<212> TYPE: DNA
<213> ORGANISM: Yarrowia lipolytica

<400> SEQUENCE: 4

| | |
|---|---|
| gtcagaaggg gcagctctaa acgaagaact gcggtcaggt gacacaactt tttccatctc | 60 |
| agggtgtgtc gcgtgtgctt catccaaact ttagttgggg ttcgggttcg cgcgagatga | 120 |
| tcacgtgccc tgatttggtg tcgtccccg tcgcgctgcg cacgtgattt atttatttcc | 180 |
| ggtggctgct gtctacgcgg ggccttctct gcccttctgt ttcaaccttc gggcggttct | 240 |
| cgtaaccagc agtagcaatc catttcgaaa ctcaaagagc taaaaacgtt aaacctcagc | 300 |
| agtcgctcga cgaatgggct gcggttggga agcccacgag gcctatagcc agagcctcga | 360 |
| gttgacagga gcccagacgc ctttttccaac ggcaactttt atataaaatg gcaatgtatt | 420 |
| catgcaattg cggccgtgtc aggttggaga cactggacca cactctccat gcttcctga | 480 |
| ggagatggat cattgctagt gcatctacgc gcagcaatcc cgcaagctcg acaaccgtag | 540 |
| atgggctttg gtgggccaat caattacgca acccgcacgt taaattgtat gaggaaggaa | 600 |
| ggccacggta caaagtgggt ggtcttcacc cagtggttgt tggtggcgtc atgcagacca | 660 |
| tgcattgggg atagcacagg gttggggtgt cttgtggact caatgggtga aggagatgg | 720 |
| aaaagggcgg tgaaaagtgg tagaatcgaa atccctgacg tcaatttata aagtaaaatg | 780 |
| cgtttctgcc attttgctcc cctccttctt tcgcaatcgc ctccccaaaa gttgtcgtgg | 840 |
| cagtacacat gcttgcatac aatgaagcta atccggcttg ctcagtagtt gctatatcca | 900 |
| ggcatggtgt gaaaccccctc aaagtatata taggagcggt gagccccagt ctggggtctt | 960 |
| ttctctccat ctcaaaacta ctttctcaca tgctagccac aaaa | 1004 |

<210> SEQ ID NO 5
<211> LENGTH: 1422
<212> TYPE: DNA
<213> ORGANISM: Yarrowia lipolytica

<400> SEQUENCE: 5

| | |
|---|---|
| atttcttgtg tgtgcggcaa acgtagcaat tgcaactgca taaacgatga ttgtaaaagt | 60 |
| atcacacttt gctcagacag gttagattca cctggtacga gggcagtgtc ttaaaggttc | 120 |
| catctacctc ggcccttgtt tcttgaagag tggtcaatat gtgttttata cagctgaaat | 180 |
| ttcccctgta tgttgagatc gtgtatattg gtcataatct gggctctta gtcgatccca | 240 |
| gttttctcgg gcaagttttt ttctccacaa agtaccgctg gaaaactcta tgtgacttgt | 300 |
| tgacagatta cttgggttat ctgcgggata tgtcttggat aggcaaccgg gcatatatca | 360 |
| ccgggcggac tgttggttct gtacgtacat acagcacttt gagctcatgt ctcacacgca | 420 |
| accatggtgc gtggaggctt tggcatcctt tctacttgta gtggctatag tacttgcagt | 480 |
| ccaagcaaac atgagtatgt gcttgtatgt actgaaaccc gtctacggta atattttaga | 540 |
| gtgtggaact atgggatgag tgctcattcg atactatgtt gtcacccgat ttgccgtttg | 600 |
| cgaggtaaga cacattcggt ggttcaggcg gctacttgta tgtagcatcc acgttcatgt | 660 |

```
tttgtggatc agattaatgg tatggatatg cacggggcgt ttccccgta acgtgtaggc      720 agtccagtgc aacccagaca gctgagctct ctatagccgt gcgtgtgcgg tcatatcacg      780
ctacacttag ctacagaata aagctcggta gcgccaacag cgttgacaaa tagctcaagg      840
gcgtggagca cagggtttag gaggttttaa tgggcgagaa ggcgcgtaga tgtagtcttc      900
ctcggtccca tcggtaatca cgtgtgtgcc gatttgcaag acgaaaagcc acgagaataa      960
accgggagag gggatggaag tccccgaaca gcaaccagcc cttgccctcg tggacataac     1020 cttttcacttg ccagaactct aagcgtcacc acggtataca agcgcacgta gaagattgtg     1080
gaagtcgtgt tggagactgt tgatttgggc ggtggagggg ggtatttgag agcaagtttg     1140
agatttgtgc cattgagggg gaggttattg tggccatgca gtcggatttg ccgtcacggg     1200
accgcaacat gcttttcatt gcagtccttc aactatccat ctcacctccc ccaatggctt     1260
ttaactttcg aatgacgaaa gcacccccct ttgtacagat gactatttgg gaccaatcca     1320
atagcgcaat tgggtttgca tcatgtataa aaggagcaat cccccactag ttataaagtc     1380
acaagtatct cagtataccc gtctaaccac acatttatca cc                       1422
```

<210> SEQ ID NO 6
<211> LENGTH: 865
<212> TYPE: DNA
<213> ORGANISM: Yarrowia lipolytica

<400> SEQUENCE: 6

```
atgctcactt tgttgtcct gatgatctcc cgttatttcg ccgctcctct ggaaaccatc       60
cgcccgcaaa tccctctgc ccatcttgac aatgcacaat gcatcattct cagcctgcat      120
gaatgcgaaa gatggcaata ttggtggagg aggcgacggc ggtaaacaat ggagatagag      180
accacaaaag agacctggag acccaaaatg gactcacgac aactccccca ctcccccact      240
ccccatctcc ccctgggcat cagttgccca tcggtatctc aactgtcgca ctagttagcg      300
caaccatcac atactttaga cgccaaacaa tgggacaact catcgcgccg aactatgggc      360
agattttaac tcgcacaaca ttaccccaac tctaaaaggt aacctcgacc ggaaaacggg      420
aagacaggat cagcaaccgt gatcgacaga atcttcaggg cactacagtt gatagacata      480
ggttatgttg gtaggtctag acgggcctcg gggaattgac cccaccagtt gcaagtcacg      540
tgcccctgat acagctagtt tagcacatct gcccactacg tctggacgca ccatggtggt      600
gccagtcgcg tgaactcaaa cacccactag cctcgggaag gattcagtta atccgcacc      660 ttatttccaa cacaagaag cggttggcgg acaaagaaca tgtcctttct ggggcactgt      720
acattccagg actctgttca aggtcaaata tacaaaacac agatagagaa acatagacag      780
ctgcggcctt ataaatacct gggcgcactt ctctcttttt ccctcctcat cacacattcg      840
ttcaccacta agtcactcgt tcaaa                                            865
```

<210> SEQ ID NO 7
<211> LENGTH: 880
<212> TYPE: DNA
<213> ORGANISM: Yarrowia lipolytica

<400> SEQUENCE: 7

```
aaacaaaaga gctgaaatca tatccttcag tagtagtata gtcctgttat cacagcatca       60 attaccccg tccaagtaag ttgattggga tttttgttta cagatacagt aatatacttg      120
actatttctt tacaggtgac tcagaaagtg catgttggaa atgagccaca gaccaagaca      180
```

```
agatatgaca aaattgcact attcgatgca gaattcgacg gtgtttccat tggtgttatg        240
acattcatct gcattcatac aaaaaagtct tggtagtggt acttttgcgt tattacctcc        300
gatatctacg caccccccaa cccccctgct acagtaaaga gtgtgagtct actgtacatg        360
cttactaaac cacctactgt acagcgaaac ccctcagcaa aatcacacaa tcagctcatt       420
acaacacacc caatgacctc accacaaatt ctatacgcct tttgacgcca ttattacagt        480
agcttgcaac gccgttgtct taggttccat ttttagtgct ctattacctc acttaacccg        540
tataggcaga tcaggccatg cactaagtg tagagctaga ggttgatatc gccacgagtg         600
ctccatcagg gctagggtgg ggttagaaat acagtccgtg cgcactcaaa aggcgtccgg        660
gttagggcat ccgataatat cgcctggact cggcgccata ttctcgactt ctgggcgcgt       720
tgtattcatc tcctccgctt cccaacactt ccaccegttt ctccatccca accaatagaa       780
tagggtaacc ttattcggga cactttcgtc atacatagtc agatatacaa gcaatgtcac       840
tctccttcgt actcgtacat acaacacaac tacattcaaa                             880

<210> SEQ ID NO 8
<211> LENGTH: 1000
<212> TYPE: DNA
<213> ORGANISM: Yarrowia lipolytica

<400> SEQUENCE: 8
caattcatgt atcgtgtcaa ttcatgtatc gtgtcaattc atgtatcgtg tcaatactta        60
tatctcaagt ggttgcatcg caaacagcca tcgcatactc cactctactc tcactgagtt       120
cactcttacc cggctccacc ttctagaagc caccaccgat ccaccgacga tgatcagtcc       180
accacttgct ctgaatgtgc gttggagctg caccatgatt gatgacgtca ccgccattca       240
gatagggcaa aagacgagcg ccaatcgcaa caatgggcga gtgtcgacga ctccccgct       300 ctctgcggtt tcagcgactc caaccgtcgc caaaagaccg tcattttcgt ctaaagcgca       360
gcccagccca tctcttctaa aagattccag aaagataggg ttcaccaact acgcaccaat       420
atgtacagta tcgtagctac tccggcttgg ctgatctgag agatagagat ggctccgaaa       480
cgcggaaaac ggcggggtcg gaccgatcac gtgacacgta ctcatccgtc gcgccccgag       540
cgccatttca acaccaaata ctcccggtca cgtgccaccc cgcccgctct acccacgaga       600
tgtttctaca ctatacactg ccacgccgtc atacctgcag ctaggttaac attcgattaa       660
ttagtggagt caccagtgta caggactatg gcggaaaccg ggttacacaa accggcccgg       720
aatagcagca ttataccgct ggacgagatc accgtcaata aattgcgtcg ttactcggga       780
caaccattgc tcctccggct acacctgctc aaaggacttg ttccacactc ttccccagct       840 ctccacgca aacaaagaga gcaaccttaa gtggacagct catgagcact cccctcgttt       900
gctgcccacg ctcgattata taaagaccag cggatccct tctatttgga cttgcatcaa      960
ccaaccacaa cccacaccaa gcacacaaag cacaagaaca                            1000

<210> SEQ ID NO 9
<211> LENGTH: 127
<212> TYPE: DNA
<213> ORGANISM: Yarrowia lipolytica

<400> SEQUENCE: 9
aattaacaga tagtttgccg gtgataattc tcttaacctc ccacactcct ttgacataac        60
gatttatgta acgaaactga aatttgacca gatattgttg taaatagaaa atctggcttg       120
taggtgg                                                                127
```

<210> SEQ ID NO 10
<211> LENGTH: 200
<212> TYPE: DNA
<213> ORGANISM: Yarrowia lipolytica

<400> SEQUENCE: 10

```
gtttttgat caatgatcca atggctttca cataccccc cacgcctata attaaaacac     60
agagaaatat aatctaactt aataaatatt acggagaatc tttcgagtgt tcagcagaaa    120
tatagccatt gtaacaaaag ccggctatcg accgctttat cgaagaatat ttcccgcccc   180
ccagtggcca aacgatatcg                                                200
```

<210> SEQ ID NO 11
<211> LENGTH: 200
<212> TYPE: DNA
<213> ORGANISM: Yarrowia lipolytica

<400> SEQUENCE: 11

```
ctatccgaag atcaagagcg aagcaagttg taagtccagg acatgtttcc cgcccacgcg    60
agtgatttat aacacctctc ttttttgaca cccgctcgcc ttgaaattca tgtcacataa   120
attatagtca acgacgtttg aataacttgt cttgtagttc gatgatgatc atatgattac   180
attaatagta attactgtat                                                200
```

<210> SEQ ID NO 12
<211> LENGTH: 200
<212> TYPE: DNA
<213> ORGANISM: Yarrowia lipolytica

<400> SEQUENCE: 12

```
acttcgagct aatccagtag cttacgttac ccaggggcag gtcaactggc tagccacgag    60
tctgtcccag gtcgcaattt agtgtaataa acaatatata tattgagtct aaagggaatt   120
gtagctattg tgattgtgtg attttcgtct tgctggttct tattgtgtcc cattcgtttc   180
atcctgatga ggaccctgg                                                200
```

<210> SEQ ID NO 13
<211> LENGTH: 200
<212> TYPE: DNA
<213> ORGANISM: Yarrowia lipolytica

<400> SEQUENCE: 13

```
gctatttaca gcatgtgtaa tgaggaatat aacgttgatt gaattgtttg tgaaaaatgt    60
agaaaatttc agtgaagttg tgttttctat atagtaagca cttttggtac aagtatctgc   120
acatccctgc atgttacaag cctgatcatg cagggcaata ttctgactat aaatatacct   180
cgatatttta gcaagctata                                                200
```

<210> SEQ ID NO 14
<211> LENGTH: 300
<212> TYPE: DNA
<213> ORGANISM: Yarrowia lipolytica

<400> SEQUENCE: 14

```
atgtggtgat tgctgttgtg caagcctttg ctcgttttct gctgtatgta atttaaagaa    60
cgattgtatg aatcgaagtc aaggtgagtg tagtttgaga agtgtaaccc cagtgtcata   120
gctgtgtact ccattcattg aagggtgtag tcgtgtttta ttgcatgagc gcctattact   180
```

```
cgtataagta actgttttgt aacacttcat gaacggagat ggtatgaaca gaagtaataa    240
tatcctggaa gtcagctgtg cccagaggtg tgtgtgggtg tggcatactt tgggacaaca    300
```

<210> SEQ ID NO 15
<211> LENGTH: 1503
<212> TYPE: DNA
<213> ORGANISM: Artificial sequence
<220> FEATURE:
<223> OTHER INFORMATION: tHMG CpO for Yarrowia lipolitica

<400> SEQUENCE: 15

```
atgacccagt ctgtgaaggt ggttgagaag cacgttccta tcgtcattga gaagcccagc     60
gagaaggagg aggacacctc ttctgaagac tccattgagc tgactgtcgg aaagcagccc    120
aagcccgtga ccgagacccg ttctctggac gacttggagg ctatcatgaa ggcaggtaag    180
accaagctcc tggaggacca cgaggttgtc aagctctctc tcgaaggcaa gctccctttg    240
tatgctcttg agaagcagct tggtgacaac acccgagctg ttggcatccg acgatctatc    300
atctcccagc agtctaatac caagactctt gagacctcaa agctccctta cctgcactac    360
gactacgacc gtgtttttgg agcctgttgc gagaacgtta ttggttacat gcctctcccc    420
gttggtgttg ctggccccat gaacattgat ggcaagaact accacattcc tatggccacc    480
actgagggtt gtcttgttgc ctcaaccatg cgaggttgca aggccatcaa cgccggtggc    540
ggtgttacca ctgtgcttac tcaggacggt atgacacgag gtcctgtgt ttccttcccc    600 tctctcaagc gggctggagc cgctaagatc tggcttgatt ccgaggaggg tctcaagtcc    660
atgcgaaagg ccttcaactc cacctctcga tttgctcgtc tccagtctct tcactctacc    720
cttgctggta acctgctgtt tattcgattc cgaaccacca ctggtgatgc catgggcatg    780
aacatgatct ccaagggcgt cgaacactct ctggccgtca tggtcaagga gtacggcttc    840
cctgatatgg acattgtgtc tgtctcgggt aactactgca ctgacaagaa gcccgcagcg    900
atcaactgga tcgaaggccg aggcaagagt gttgttgccg aagccaccat ccctgctcac    960
attgtcaagt ctgttctcaa aagtgaggtt gacgctcttg ttgagctcaa catcagcaag   1020
aatctgatcg gtagtgccat ggctggctct gtgggaggtt tcaatgcaca cgccgcaaac   1080
ctggtgaccg ccatctacct tgccactggc caggatcctg ctcagaatgt cgagtcttcc   1140
aactgcatca cgctgatgag caacgtcgac ggtaacctgc tcatctccgt ttccatgcct   1200
tctatcgagg tcggtaccat tggtggaggt actattttgg agccccaggg tgctatgctg   1260
gagatgcttg gcgtgcgagg tcctcacatc gagaccccccg tgccaacgc caacagctt    1320 gctcgcatca ttgcttctgg agttcttgca gcggagcttt cgctgtgttc tgctcttgct   1380
gccggccatc ttgtgcaaag tcatatgacc cacaaccgtt cccaggctcc tactccggcc   1440
aagcagtctc aggccgatct gcagcgtctc caaaacggtt cgaatatctg cattcggtca   1500
tag                                                                 1503
```

<210> SEQ ID NO 16
<211> LENGTH: 984
<212> TYPE: DNA
<213> ORGANISM: Artificial sequence
<220> FEATURE:
<223> OTHER INFORMATION: GGS CpO for Yarrowia lipolitica

<400> SEQUENCE: 16

```
atggattata cagcgcgga tttcaaggag atctggggca aggccgccga caccgcgctg     60
ctgggaccgt acaactacct cgccaacaac cggggccaca acatcagaga acacttgatc    120
```

```
gcagcgttcg gagcggttat caaggtggac aagagcgatc tcgaaaccat ttcgcacatc    180
accaagattt tgcataactc gtcgctgctt gttgatgacg tggaagacaa ctcgatgctc    240
cgacgaggcc tgccggcagc ccattgtctg tttggagtcc cccaaaccat caactccgcc    300
aactacatgt actttgtggc tctgcaggag gtgctcaagc tcaagtctta tgatgccgtc    360 tccatttttca ccgaggaaat gatcaacttg catagaggtc agggtatgga tctctactgg    420
agagaaacac tcacttgccc ctcggaagac gagtatctgg agatggtggt gcacaagacc    480
ggaggactgt ttcggctggc tctgagactt atgctgtcgg tggcatcgaa acaggaggac    540
catgaaaaga tcaactttga tctcacacac cttaccgaca cactgggagt catttaccag    600
attctggatg attacctcaa cctgcagtcc acggaattga ccgagaacaa gggattctgc    660
gaagatatca gcgaaggaaa gttttcgttt ccgctgattc acagcatccg gaccaacccg    720
gataaccacg agattctcaa cattctcaaa cagcgaacaa gcgacgcttc actcaaaaag    780
tacgccgtgg actacatgag aacagaaacc aagagtttcg actactgcct caagagaatc    840
caggccatgt cactcaaggc aagttcgtac attgatgatc tcgcagcagc cggccacgat    900
gtctccaagt tgcgagccat tttgcattat tttgtgtcca cctctgactg tgaggagaga    960
aagtactttg aggatgcgca gtga                                           984
```

```
<210> SEQ ID NO 17
<211> LENGTH: 1446
<212> TYPE: DNA
<213> ORGANISM: Artificial sequence
<220> FEATURE:
<223> OTHER INFORMATION: UGT1 CpO for Yarrowia lipolitica

<400> SEQUENCE: 17
```

```
atggacgcca tggccaccac cgagaagaag ccccacgtca tcttcatccc cttcccgcc     60 cagtcccaca tcaaggccat gctcaagctc gcccagctcc tccaccacaa gggcctccag    120
atcacctttg tcaacaccga cttcatccac aaccagttcc tcgagtcctc cggcccccac    180
tgtctggacg tgctcccggt tttccgattt gagactatcc ccgatggtgt ctcccactcc    240
cccgaggcct ccatcccccat ccgagagtct ctgctccgat ccattgagac taacttcctc    300
gaccgattca ttgatctcgt caccaagctc cccgatcctc ccacctgtat catctccgac    360
ggtttcctgt ccgtttttcac cattgatgct gccaagaagc tcggtatccc cgtcatgatg    420
tactggactc tggctgcctg tggtttcatg ggtttctacc acatccactc tctgatcgag    480
aagggctttg ctcctctcaa ggacgcctcc tacctcacca acggttacct cgacaccgtc    540
attgactggg tccccggtat ggagggtatc cgactcaagg acttccccct cgactggtcc    600
accgacctca cgacaaggt tctcatgttc accaccgagg ctcccagcg atcccacaag    660 gtttcccacc acatcttcca caccttcgac gagctcgagc cctccatcat caagactctg    720
tctctgcgat acaaccacat ctacaccatt ggccccctcc agctcctcct cgaccagatc    780
cccgaggaga agaagcagac cggtatcacc tctctgcacg gctactctct cgtcaaggaa    840
gagcccgagt gcttccagtg gctccagtcc aaggagccca actccgttgt ctacgtcaac    900
tttggctcca ccaccgtcat gtctctcgag gacatgacccg agtttggctg gggtctggcc    960
aactccaacc actacttcct gtggatcatc cgatccaacc tcgtcattgg cgagaacgcc   1020
gttctgcctc ccgagctcga ggagcacatc aagaagcgag gcttcattgc ctcttggtgc   1080
tcccaggaga aggttctcaa gcaccccctcc gtcggtggtt tcctgaccca ctgcggctgg   1140
```

```
ggctccacca ttgagtctct gtccgctggt gtcccatga tctgctggcc ctactcctgg    1200
gaccagctca ccaactgccg atacatctgc aaggagtggg aggttggtct ggagatgggt    1260
accaaggtca agcgagatga ggtcaagcga ctcgtccagg agctcatggg cgagggtggt    1320
cacaagatgc gaaacaaggc caaggactgg aaggagaagg cccgaattgc cattgccccc    1380
aacggctctt cttctctcaa cattgacaag atggtcaagg agatcactgt tctcgctcga    1440
aactaa                                                              1446

<210> SEQ ID NO 18
<211> LENGTH: 1383
<212> TYPE: DNA
<213> ORGANISM: Artificial sequence
<220> FEATURE:
<223> OTHER INFORMATION: UGT3 CpO for Yarrowia lipolitica

<400> SEQUENCE: 18
atggccgagc agcagaagat caagaagtct ccccacgttc tgctcatccc cttccctctg      60
cagggccaca tcaaccccct catccagttc ggcaagcgac tcatctccaa gggtgtcaag     120
accactctgg tcaccaccat ccacacccte aactccactc tcaaccactc caacaccacc     180
accacctcca tcgagatcca ggccatctcc gacggctgtg acgagggtgg tttcatgtct     240
gctggtgagt cttacctcga ctttcaag caggtcggtt ccaagtctct ggctgacctc       300
atcaagaagc tccagtccga gggtaccacc attgacgcca tcatctacga ctccatgacc     360
gagtgggttc tcgatgtcgc catcgagttt ggtattgacg gtggctcctt cttcacccag     420
gcctgtgtcg tcaactctct ctactaccac gtccacaagg tctgatctc tctgcccctc     480 ggcgagactg tctccgtccc cggtttcccc gttctgcagc gatgggagac tcctctcatt     540
ctccagaacc acgagcagat ccagtccccc tggtcccaga tgctcttcgg ccagttcgcc     600
aacattgacc aggcccgatg ggttttcacc aactccttct acaagctcga ggaagaggtc     660
attgagtgga cccgaaagat ctggaacctc aaggtcattg gccccaccct cccctccatg     720
tacctcgaca gcgactcga tgacgacaag acaacggtt tcaacctcta caaggccaac     780
caccacgagt gcatgaactg gctcgacgac aagcccaagg agtccgttgt ctacgttgcc     840
tttggctctc tggtcaagca cggccccgag caggttgagg agatcacccg agctctgatt     900
gactccgatg tcaacttcct gtgggtcatc aagcacaagg aagagggtaa gctccccgag     960
aacctgtccg aggtcatcaa gaccggcaag ggcctcattg ttgcctggtg caagcagctc    1020
gacgttctcg cccacgagtc cgtcggctgc tttgtcaccc actgcggttt caactccacc    1080
ctcgaggcta tctctctcgg tgtccccgtt gttgccatgc ccagttctc cgaccagacc    1140 accaacgcca agtccctcga tgagattctc ggtgtcggtg tccgagtcaa ggctgacgag    1200
aacggtattg tccgacgagg taacctggct tcttgtatca agatgatcat ggaggaagag    1260
cgaggtgtca tcatccgaaa gaacgccgtc aagtggaagg atctggccaa ggttgctgtc    1320
cacgagggtg gctcttccga caacgacatt gtcgagtttg tctccgagct catcaaggcc    1380
taa                                                                  1383

<210> SEQ ID NO 19
<211> LENGTH: 1377
<212> TYPE: DNA
<213> ORGANISM: Artificial sequence
<220> FEATURE:
<223> OTHER INFORMATION: UGT4 CpO for Yarrowia lipolitica

<400> SEQUENCE: 19
```

-continued

```
atggagaaca agaccgagac taccgtccga cgacgacgac gaatcattct cttccccgtc    60
cccttccagg gccacatcaa ccccattctg cagctcgcca acgttctgta ctccaagggc   120
ttctccatca ccatcttcca caccaacttc aacaagccca agacctccaa ctaccccccac  180
ttcactttcc gattcatcct cgacaacgac ccccaggacg agcgaatctc caacctgccc   240
acccacggtc tctggctgg tatgcgaatc cccatcatca acgagcacgg tgctgacgag    300
ctccgacgag agctcgagct gctcatgctc gcctccgaag aggacgagga agtctcctgt   360
ctgatcaccg atgctctgtg gtactttgcc cagtccgtcg ccgactctct caacctgcga   420
cgactcgttc tcatgacctc ctctctgttc aacttccacg cccacgtttc tctgccccag   480
tttgacgagc tcggttacct cgaccccgat gacaagaccc gactcgagga gcaggcttcc   540
ggtttcccca tgctcaaggt caaggacatc aagtccgcct actccaactg cagattctc    600
aaggagattc tcggcaagat gatcaagcag accaaggcct cctccggtgt catctggaac   660
tccttcaagg agctcgagga gtccgagctc gagactgtca tccgagagat ccccgctccc   720
tctttcctca tccccctgcc caagcacctc accgcttcct cctcttctct gctcgaccac   780
gaccgaaccg tctttcagtg gctcgaccag cagccccctt cctccgtcct ctacgtttcc   840
ttcggctcca cctccgaggt cgacgagaag gacttcctcg agattgctcg aggcctcgtt   900
gactccaagc agtccttcct gtgggttgtc cgacccggct tgtcaaggg ctccacctgg    960
gttgagcccc tgcccgatgg tttcctcggt gagcgaggcc gaattgtcaa gtgggtcccc  1020
cagcaggaag ttctggccca cggtgccatt ggtgccttct ggacccactc cggctggaac  1080
tccactctcg agtccgtctg cgagggtgtc cccatgatct ctccgactt tggcctcgac   1140
cagcccctca cgcccgata catgtccgat gttctcaagg tcggtgtcta cctcgagaac   1200
ggctgggagc gaggtgagat tgccaacgcc atccgacgag tcatggtcga cgaggaaggt  1260
gagtacatcc gacagaacgc ccgagtcctc aagcagaagg ccgatgtctc tctcatgaag  1320
ggtggttctt cttacgagtc tctcgagtct ctcgtttcct acatctcttc tttgtaa     1377
```

<210> SEQ ID NO 20
<211> LENGTH: 2232
<212> TYPE: DNA
<213> ORGANISM: Artificial sequence
<220> FEATURE:
<223> OTHER INFORMATION: tCPS_SR CpO for Yarrowia lipolitica

<400> SEQUENCE: 20

```
atgtgcaagg ctgtttccaa ggagtactcc gatctgctcc agaaggacga ggcctctttc    60
accaagtggg acgacgacaa ggtcaaggac cacctcgaca ccaacaagaa cctctacccc   120
aacgacgaga tcaaggagtt tgtcgagtcc gtcaaggcca tgttcggctc catgaacgac   180
ggcgagatta atgtctctgc ttacgacacc gcctgggttg ctctggtcca ggatgtcgac   240
ggttccggct ctcctcagtt cccttcctct ctcgagtgga tcgccaacaa ccagctgtcc   300
gacggttctt ggggtgacca cctgctcttc tctgctcacg accgaatcat caacaccctg   360
gcctgtgtca ttgctctgac ctcttggaac gtccacccct ccaagtgcga aagggtctg    420
aacttcctcc gagagaacat ctgcaagctc gaggacgaga acgccgagca catgcccatt   480
ggcttcgagg tcaccttccc ctctctgatt gacattgcca agaagctcaa cattgaggtc   540
cccgaggaca ccccgctct caaggagatc tacgctcgac gagacatcaa gctcaccaag   600
atccccatgg aggttctcca caaggtcccc accactctcc tccactctct cgagggtatg   660
```

-continued

```
cccgatctcg agtgggagaa gctgctcaag ctgcagtgca aggacggctc tttcctcttc      720
tccccctctt ccactgcctt cgccctcatg cagaccaagg acgagaagtg tctccagtac      780
ctcaccaaca ttgtcaccaa gttcaacggt ggtgtcccca acgtctaccc cgttgacctc      840
tttgagcaca tctgggttgt tgaccgactc cagcgactcg gtatcgcccg atacttcaag      900
tccgagatca aggactgtgt cgagtacatc aacaagtact ggaccaagaa cggtatctgc      960
tgggcccgaa acacccacgt ccaggacatt gacgacaccg ccatgggctt ccgagttctg     1020
cgagcccacg gctacgatgt caccccccgat gtctttcgac agtttgagaa ggacggcaag     1080
tttgtctgtt cgccggtcaa gtccaccccag gccgtcaccg gtatgttcaa cgtctaccga     1140
gcttctcaga tgctcttccc cggtgagcga atcctcgagg acgccaagaa gttctcctac     1200
aactacctca aggagaagca gtccaccaac gagctgctcg acaagtggat cattgccaag     1260
gatctgcccg gtgaggttgg ctacgccctc gacatcccct ggtacgcctc tctgccccga     1320
ctggagactc gatactacct cgagcagtac ggtggtgagg acgatgtctg gatcggtaag     1380
accctgtacc gaatgggcta cgtttccaac aacacctacc tcgagatggc caagctcgac     1440
tacaacaact acgttgccgt cctccagctc gagtggtaca ccatccagca gtggtacgtc     1500
gacattggta tcgagaagtt cgagtccgac aacatcaagt ccgtccttgt ctcctactac     1560
ctcgctgctg cctccatctt cgagcccgag cgatccaagg agcgaattgc ctgggccaag     1620
accaccatcc tcgtcgacaa gatcacctcc atcttcgact cctcccagtc ctccaaggaa     1680
gatatcaccg ccttcattga caagttccga aacaagtcct cctccaagaa gcactccatc     1740
aacggcgagc cctggcacga ggtcatggtt gctctcaaga aaactctcca cggctttgcc     1800
ctcgacgctc tgatgaccca ctctcaggac atccaccccc agctccacca ggcctgggag     1860
atgtggctca ccaagctcca ggacggtgtt gatgtcactg ctgagctcat ggtccagatg     1920
atcaacatga ccgccggccg atgggtttcc aaggagctcc tcacccaccc ccagtaccag     1980
cgactctcca ctgtcaccaa ctctgtctgc cacgacatca ccaagctcca caacttcaag     2040
gagaactcca ccaccgtcga ctccaaggtc caggagctgg tccagctcgt tttctccgac     2100 accccccgatg atctcgacca ggacatgaag cagaccttcc tgactgtcat gaaaactttc     2160
tactacaagg cctggtgcga ccccaacacc atcaacgacc acatctccaa ggtctttgag     2220
attgtgattt aa                                                          2232
```

<210> SEQ ID NO 21
<211> LENGTH: 2274
<212> TYPE: DNA
<213> ORGANISM: Artificial sequence
<220> FEATURE:
<223> OTHER INFORMATION: tKS-SR CpO for Yarrowia lipolitica

<400> SEQUENCE: 21

```
atgacctccc acggcggcca gaccaacccc accaacctca tcattgacac caccaaggag       60
cgaatccaga agcagttcaa gaacgtcgag atctccgttt cctcctacga caccgcctgg      120
gtcgccatgg tccctctctc caactccccc aagtctccct gcttccccga gtgtctcaac      180
tggctcatca caaccagct caacgacggc tcttggggtc tggtcaacca cacccacaac      240
cacaaccacc cctcctcaa ggactctctc tcttccactc tcgcctgcat tgttgctctc      300
aagcgatgga acgttggcga ggaccagatc aacaagggtc tgtctttcat tgagtccaac      360
ctcgcctccg ccaccgagaa gtcccagccc tcccccattg gctttgatat catcttcccc      420
ggtctgctcg agtacgccaa gaacctcgat atcaacctgc tctccaagca gaccgacttc      480
```

-continued

```
tctctcatgc tgcacaagcg agagctcgag cagaagcgat gccactccaa cgagatggac     540
ggctacctgg cctacatttc cgagggtctg ggtaacctct acgactggaa catggtcaag     600
aagtaccaga tgaagaacgg ttccgttttc aactccccct ctgccaccgc tgctgccttc     660
atcaaccacc agaaccccgg ctgtctcaac tacctcaact ctctgctcga caagtttggt     720
aacgccgtcc ccactgtcta cccccacgat ctcttcatcc gactctccat ggtcgacacc     780
attgagcgac tcggtatttc ccaccactt cgagtcgaga tcaagaacgt tctcgatgag      840
acttaccgat gctgggttga gcgagatgag cagatcttca tggacgttgt cacctgtgct     900
ctggccttcc gactcctccg aatcaacggt tacgaggttt cccccgaccc cctcgccgag     960
atcaccaacg agctggctct caaggacgag tacgccgccc tcgagactta ccacgcttct    1020
cacattctgt accaagagga tctgtcctcc ggcaagcaga ttctcaagtc cgccgacttc    1080
ctcaaggaga tcatctccac tgactccaac cgactctcca agctcatcca aggaagtc     1140 gagaacgctc tcaagttccc catcaacacc ggtctggagc gaatcaacac ccgacgaaac    1200
atccagctct acaacgtcga caacacccga attctcaaga ccacctacca ctcttccaac    1260
atctccaaca ccgactacct gcgactcgcc gtcgaggact tctacacctg ccagtccatc    1320
taccgagagg agctcaaggg tctggagcga tgggttgtcg agaacaagct cgaccagctc    1380
aagtttgccc gacaaaagac tgcctactgc tacttctccg ttgctgccac cctctcttct    1440
cccgagctct ccgacgcccg aatctcttgg gccaagaacg gtatcctgac cactgttgtc    1500
gacgacttct ttgacattgg tggcaccatt gacgagctga ccaacctcat ccagtgcgtc    1560
gagaagtgga acgtcgacgt tgacaaggac tgttgttccg agcacgtccg aatcctcttc    1620
ctggctctca aggacgccat ctgctggatc ggtgacgagg ccttcaagtg gcaggctcga    1680
gatgtcactt cccacgtcat ccagacctgg ctcgagctca tgaactccat gctgcgagag    1740
gccatctgga cccgagatgc ctacgtcccc accctcaacg agtacatgga gaacgcctac    1800
gtcagctttg ctctcggtcc cattgtcaag cccgccatct actttgtcgg tcccaagctg    1860
tccgaggaga ttgtcgagtc ctccgagtac acaaacctct tcaagctcat gtccacccag    1920
ggccgactcc tcaacgatat ccactccttc aagcgagagt tcaaggaagg taagctcaac    1980
gccgttgctc tgcacctgtc caacggtgag tccggcaagg tcgaggaaga ggtcgtcgag    2040
gagatgatga tgatgatcaa gaacaagcga aaggagctca tgaagctcat cttcgaggag    2100
aacggctcca ttgtcccccg agcctgcaag gacgccttct ggaacatgtg ccacgtcctc    2160
aacttcttct acgccaacga cgacggtttc accggcaaca ccattctcga caccgtcaag    2220
gacatcatct acaaccctct ggttctggtc aacgagaacg aggagcagag gtaa          2274
```

<210> SEQ ID NO 22
<211> LENGTH: 1578
<212> TYPE: DNA
<213> ORGANISM: Artificial sequence
<220> FEATURE:
<223> OTHER INFORMATION: KAH_4 CpO for Yarrowia lipolitica

<400> SEQUENCE: 22

```
atggagtctc tggttgtcca caccgtcaac gccatctggt gcattgtcat tgtcggtatc      60
ttctccgtcg gctaccacgt ctacggccga gctgttgtcg agcagtggcg aatgcgacga     120
tctctcaagc tccagggtgt caagggtcct cctcccctca tcttcaacgg taacgtttcc     180
gagatgcagc gaatccagtc cgaggccaag cactgctccg gtgacaacat catctcccac     240
```

```
gactactctt cttctctgtt ccccccacttt gaccactggc gaaagcagta cggccgaatc     300
tacacctact ccactggcct caagcagcac ctctacatca accacccccga gatggtcaag     360
gagctctccc agaccaacac cctcaacctc ggccgaatca cccacatcac caagcgactc     420
aaccccattc tcggtaacgg tatcatcacc tccaacggcc cccactgggc ccaccagcga     480
cgaatcattg cctacgagtt cacccacgac aagatcaagg gtatggtcgg tctgatggtc     540
gagtccgcca tgcccatgct caacaagtgg gaggagatgg tcaagcgagg tggtgagatg     600
ggctgtgaca tccgagtcga cgaggacctc aaggatgtct ccgctgacgt cattgccaag     660
gcctgtttcg gctcttcctt ctccaagggc aaggccatct tctccatgat ccgagatctg     720
ctcaccgcca tcaccaagcg atccgtcctc ttccgattca acggtttcac cgacatggtt     780
ttcggctcca agaagcacgg tgacgttgac attgacgctc tcgagatgga gctcgagtcc     840
tccatctggg agactgtcaa ggagcgagag attgagtgca aggacaccca caagaaggac     900
ctcatgcagc tcattctcga gggtgccatg cgatcttgtg acggtaacct gtgggacaag     960
tctgcttacc gacgattcgt tgtcgacaac tgcaagtcca tctactttgc cggccacgac    1020
tccaccgccg tttccgtttc ttggtgcctc atgctgctcg ctctcaaccc ctcttggcag    1080
gtcaagatcc gagatgagat tctgtcctcc tgcaagaacg gtatcccga cgccgagtcc    1140
atccccaacc tcaagaccgt caccatggtc atccaggaga ctatgcgact ctaccctccc    1200
gctcccattg tcggccgaga ggcctccaag gacattcgac tcggtgatct ggttgtcccc    1260
aagggtgtct gtatctggac cctcatcccc gctctgcacc gagatccga gatctggggt    1320
cccgacgcca acgacttcaa gcccgagcga ttctccgagg gtatctccaa ggcctgcaag    1380
taccccagt cctacatccc ctttggcctc ggccccgaa cctgtgtcgg caagaacttt    1440
ggtatgatgg aggtcaaggt cctcgtttct ctgattgtct ccaagttctc cttcactctg    1500
tctcccacct accagcactc tccctcccac aagctgctcg tcgagcccca gcacggtgtt    1560
gtcatccgag ttgtataa                                                  1578

<210> SEQ ID NO 23
<211> LENGTH: 1578
<212> TYPE: DNA
<213> ORGANISM: Artificial sequence
<220> FEATURE:
<223> OTHER INFORMATION: KO_Gib CpO for Yarrowia lipolitica

<400> SEQUENCE: 23
atgtccaagt ccaactccat gaactccacc tcccacgaga ctctcttcca gcagctcgtt      60
ctcggcctcg accgaatgcc cctcatggac gtccactggc tcatctacgt tgccttttggt    120
gcctggctct gctcctacgt catccacgtt ctgtcctctt cctccactgt caaggtcccc    180
gtcgtcggtt accgatccgt tttcgagccc acctggctcc tccgactgcg attcgtctgg    240
gagggtggtt ccatcattgg ccagggctac aacaagttca aggactccat cttccaggtc    300
cgaaagctcg gtaccgacat tgtcatcatc cctcccaact acattgacga ggtccgaaag    360
ctctcccagg acaagacccg atccgtcgag cccttcatca acgactttgc cggccagtac    420
acccgaggta tggtctttct gcagtccgat ctccagaacc gagtcatcca gcagcgactc    480
accccccaagc ttgtctctct caccaaggtc atgaaggaag agctcgacta cgctctgacc    540
aaggagatgc ccgacatgaa gaacgacgag tgggttgagg tcgacatctc ttccatcatg    600
gtccgactca tctctcgaat ctccgcccga gttttcctcg ccccgagca ctgccgaaac    660
caggagtggc tcaccaccac cgccgagtac tccgagtctc tcttcatcac cggcttcatc    720
```

```
ctccgagttg tcccccacat tctccgaccc ttcattgctc ctctgctgcc ctcttaccga    780
accctgctgc gaaacgtttc ttccggccga cgagtcattg gtgatatcat ccgatcccag    840
cagggtgacg gtaacgagga catcctctct tggatgcgag atgctgccac tggtgaggag    900
aagcagatcg acaacattgc ccagcgaatg ctcattctgt ctctcgcctc catccacacc    960
accgccatga ccatgaccca cgccatgtac gatctgtgtg cctgccccga gtacattgag   1020
cccctccgag atgaggtcaa gtccgtcgtt ggtgcttctg gctgggacaa gaccgctctc   1080
aaccgattcc acaagctcga ctctttcctc aaggagtccc agcgattcaa ccccgttttc   1140
ctgctcacct tcaaccgaat ctaccaccag tccatgaccc tctccgatgg taccaacatc   1200
ccctccggta cccgaattgc tgtcccctct cacgccatgc tccaggactc cgcccacgtc   1260
cccggtccca ctcctcccac tgagttcgac ggtttccgat actccaagat ccgatccgac   1320
tccaactacg cccagaagta cctcttctcc atgaccgact cttccaacat ggcctttggc   1380
tacggtaagt acgcctgccc cggccgattc tacgcctcca cgagatgaa gctgactctg   1440
gccattctgc tcctccagtt tgagttcaag ctccccgacg gtaagggccg acccgaaac   1500
atcaccatcg actccgacat gatcccccgac cccgagctc gactctgtgt ccgaaagcga   1560
tctctgcgtg acgagtaa                                                 1578
```

<210> SEQ ID NO 24
<211> LENGTH: 2133
<212> TYPE: DNA
<213> ORGANISM: Artificial sequence
<220> FEATURE:
<223> OTHER INFORMATION: CPR_3 CpO for Yarrowia lipolitica

<400> SEQUENCE: 24

```
atgtcctcct cttcttcttc ttccacctcc atgattgatc tcatggctgc catcatcaag     60
ggtgagcccg tcattgtctc cgaccccgcc aacgcctccg cctacagagtc cgttgctgcc    120
gagctgtcct ccatgctcat cgagaaccga cagtttgcca tgatcgtcac cacctccatt    180
gctgttctca ttggctgcat tgtcatgctc gtctggcgac gatctggctc cggtaactcc    240
aagcgagtcg agcccctcaa gcccctggtc atcaagcccc gagaagagga gatcgacgac    300
ggccgaaaga aggtcaccat cttctttggc acccagaccg gtactgctga gggcttcgcc    360
aaggctctcg gtgaggaagc caaggctcga tacgaaaaga cccgattcaa gattgtcgac    420
ctcgatgatt acgctgccga tgacgacgag tacgaggaga agctcaagaa agaggacgtt    480
gccttcttct tcctcgccac ctacggtgac ggtgagccca ccgacaacgc tgcccgattc    540
tacaagtggt tcaccgaggg taacgaccga ggcgagtggc tcaagaacct caagtacggt    600
gttttcggtc tgggcaaccg acagtacgag cacttcaaca aggttgccaa ggttgtcgac    660
gacatcctcg tcgagcaggg tgcccagcga ctcgtccagg tcggcctcgg tgatgatgac    720
cagtgcatcg aggacgactt cactgcctgg cgagaggctc tgtggcccga gctcgacacc    780
attctgcgag aggaaggtga caccgccgtt gccaccccct acaccgccgc cgtcctcgag    840
taccgagtct ccatccacga ctccgaggat gccaagttca cgacatcaa catggccaac    900
ggtaacggct acaccgtctt tgacgcccag caccccctaca aggccaacgt cgccgtcaag    960
cgagagctcc acacccccga gtccgaccga tcttgtatcc acctcgagtt tgacattgct   1020
ggttccggtc tgacctacga gactggtgac acgttggtg tcctctgtga caacctgtcc   1080
gagactgtcg acgaggctct gcgactcctc gacatgtccc ccgacactta cttctctctg   1140
```

-continued

| | |
|---|---|
| cacgccgaga aagaggacgg tactcccatc tcttcttctc tgcccccctcc cttccctccc | 1200 |
| tgcaacctgc gaaccgctct gacccgatac gcctgcctcc tctcttctcc caagaagtct | 1260 |
| gctctcgttg ctctggccgc ccacgcctcc gacccaccg aggctgagcg actcaagcac | 1320 |
| ctcgcctctc ccgctggcaa ggacgagtac tccaagtggg ttgtcgagtc ccagcgatct | 1380 |
| ctgctcgagg tcatggccga gttccctcc gccaagcccc ctctcggtgt tttcttcgcc | 1440 |
| ggtgttgctc cccgactcca gccccgattc tactccatct cctcttcccc caagatcgcc | 1500 |
| gagactcgaa tccacgttac ctgtgctctg gtctacgaga agatgcccac cggccgaatc | 1560 |
| cacaagggtg tctgctccac ctggatgaag aacgccgttc cctacgagaa gtccgagaac | 1620 |
| tgttcctctg ctcccatctt tgtccgacag tccaacttca agctcccctc cgactccaag | 1680 |
| gtccccatca tcatgattgg ccccggtacc ggcctcgccc ccttccgagg cttcctgcag | 1740 |
| gagcgactcg ccctcgtcga gtccggtgtc gagctcggcc cctccgtcct cttctttggc | 1800 |
| tgccgaaacc gacgaatgga cttcatctac aagaggagc tccagcgatt cgtcgagtcc | 1860 |
| ggtgctctcg ccgagctctc cgttgccttc tcccgagagg gtcccaccaa ggagtacgtc | 1920 |
| cagcacaaga tgatggacaa ggcctccgac atctggaaca tgatctccca gggcgcctac | 1980 |
| ctctacgtct gcggtgacgc caagggtatg gcccgagatg tccaccgatc tctgcacacc | 2040 |
| attgcccagg agcagggctc catggactcc accaaggccg agggtttcgt caagaacctc | 2100 |
| cagacctccg gccgatacct ccgagatgtc tgg | 2133 |

<210> SEQ ID NO 25
<211> LENGTH: 1419
<212> TYPE: DNA
<213> ORGANISM: Artificial sequence
<220> FEATURE:
<223> OTHER INFORMATION: UGT2_10b CpO for Y. lipolitica

<400> SEQUENCE: 25

| | |
|---|---|
| atggccacct ccgactccat tgttgacgac cgaaagaagc tccacattgt catgttcccc | 60 |
| tggctcgcct ttggccacat catccccctat ctcgagcttt ccaagctcat tgcccagaag | 120 |
| ggccacaagg tttccttcct ctccaccacc aagaacattg accgactctc ctcccacatc | 180 |
| tctcccctca tcaactttgt caagctcacc ctcccccgag tccaggagct gcccgaggac | 240 |
| gccgaggcca ccactgatgt ccaccccgag gatatcccct acctcaagaa ggcctccgac | 300 |
| ggcctccagc ccgaggtcac tgagttcctc gagcagcact ctcccgactg gatcatctac | 360 |
| gactacaccc actactggct ccccgagatt gccaagtctc tcggtgtctc tcgagcccac | 420 |
| ttctccgtca ccaccccctg ggccattgct tacatgggtc ccactgccga tgccatgatc | 480 |
| aacggttccg actaccgaac cgagcttgag gacttcaccg tccctcccaa gtggttcccc | 540 |
| ttccccacca ccgtctgctg gcgaaagcac gatctggccc gactcgtccc ctacaaggct | 600 |
| cccggtatct ccgacggtta ccgaatgggc ctcgtcatca agggctgcga ctgtctgctc | 660 |
| tccaagacct accacgagtt cggtactcag tggctccgac ttctcgagga gctgcaccga | 720 |
| gtccccgtca tccccgttgg tctgctccct ccctccatcc ccggctctga caaggacgac | 780 |
| tcttgggttt tccatcaagga gtggctcgac ggccaggaga agggctccgt tgtctacgtt | 840 |
| gctctcggtt ccgaggttct cgtcacccag gaagaggttg tcgagcttgc tcacggtctg | 900 |
| gagctgtccg gtctgccctt cttctggggc taccgaaagc caagggtcc cgccaagtcc | 960 |
| gactccgtca gcttcccga tggtttcgtc gagcgagtcc gagatcgagg tctggtctgg | 1020 |
| acctcttggg ctccccagct ccgaatcctc tcccacgagt ccgttgctgg tttcctcacc | 1080 |

```
cactgcggtt ccggctccat tgtcgagggc ctcatgttcg gccaccctct catcatgctc    1140
cccatcttcg gtgaccagcc cctcaacgcc cgactccttg aggacaagca ggtcggtatc    1200
gagatccccc gaaacgagga agatggttct tcacccgag  actctgttgc cgagtctctg    1260
cgactcgtca tggtcgagga agagggtaag atctaccgag agaaggccaa ggagatgtcc    1320
aagctctttg gcgacaagga cctccaggac cagtacgtcg acgactttgt cgagtacctc    1380
cagaagcacc gacgagctgt tgccattgac cacgaaagc                           1419

<210> SEQ ID NO 26
<211> LENGTH: 1758
<212> TYPE: DNA
<213> ORGANISM: Yarrowia lipolytica

<400> SEQUENCE: 26
atggaatgga tttcacatct ggagaacgat gacgatgtgc tggaaatcga ggactacaag      60
gtgcgcaagg acgcgctgct gatcgccatt caagtaaccc agaacgccat taacaacgga     120
actcttcata aggccttgga ggcagccttc gatgctgtga ctgacagaat cgtcatatcg     180
ccgcaagatt acaccggcgt tatgctgttc ggtgcctcca tgcagtctga ggacgacggt     240
gacgagttcg atgatgagtc agatacacat ttcattctca agctgggcct tcctaccgct     300
gctcagatca aacgactcaa acgactggca gaggaccctg atctgggtga gggttcaag     360 gtgcaggaag agcctcacct gatggacgtg tttttcgaca tgaaccgcca ttttatcaac     420
atggcaccca acttcgcgtc cagacgaatc atctatatca cagacgacga tacccccacg     480
acgaatgagg acgatatcaa caagacacga gttcgaattg aggatctaag ccatctcaag     540
gtgaaggtcg agcctctttt gatcaaccct tcggaagaca agacgttcga ctcctccaaa     600
ttctacgctc ttgtgttcaa cgaagacaca tctgtggagc cggttgaggc gatcgatttg     660
aagcagttta tcaacaaaag aaacgtgctc aatcgatcac tgttcaatgt caaaatggaa     720
atcggagaag gtcttgttgt cggagtaaga ggataccttc tttatgcgga acaaaaggct     780
acttcaacaa cccgaaaggc ctgggtttac actggaggtg agaaacccga gattgccaaa     840
ttagaatcgc aggccgtcac tattgaaagt ggcagaagcg tggacaaggc agatctgaga     900
aagactttca gtttggaaaa tgactatgtt cctttcacag aagaacagct gacgcaaatc     960
cggtactttg gagagccaat tattcgaatt ctcggcttcc acaattcctc ggacttctcc    1020
gagctcttca tccacagtgt ccgatcgtca atgttcctat atcccactga tgagaagctt    1080
gtgggttcga ttcgagccct tcagcactc tatcagagtc tcaagaacaa ggataagatg    1140
gctctggcct gggttattgt ccgcaagggc gccaaaccta ttctggctct tcttattcct    1200
tcaactaagg agatcgaagg tcttcatatg gtcttcttgc cttttacaga tgatattcga    1260
caagaaccaa agactgaact tgtgtctgcc gccccctgagc tcgtggacgc aaccaagaat    1320
attttcactc gtctacgcat gcctggcgga tttgagtcgc aaagataccc caaccccgt    1380 ctacagtggc attaccgagt tgtacgagcc atggcccttc aggaggaggt tcccaaggta    1440
cccgaagaca agacgacacc aaagtatcgg tctattgata ctcgagttgg tgatgccatc    1500
gaggaatgga acaaggtgtt gcagagcagc tccaagcgac ctgcggagga tatctgtaag    1560
gctgagaaga agtcaagag ttctgacgcg ggccctccgt ccaacgagca aatgcaaaat    1620
atggttgaga atgacattgt cggcaagctg accgtcgcag aactcagggc ttggggtgct    1680
gctaacaatg ttgagcccaa tggtagcaag ttgaagaagg actgggttga ggtggtcaaa    1740
```
aagtactatg ggaagtga                                                  1758

<210> SEQ ID NO 27
<211> LENGTH: 4245
<212> TYPE: DNA
<213> ORGANISM: Yarrowia lipolytica

<400> SEQUENCE: 27

```
atgggtaaaa ccgaagtgac acaggagagt ctagaatgcg ggtcggtcac gtcctcgctg     60
gggaaaaagc ccttctccat catcacactc ttcaccggca gacgcattcc tccggtacct    120
actgaaaaac cagattcggc cgaagaacgg gccgggattc tgtcaaaatt gacctggcaa    180
tggcttagtc cattgttgaa aactggttac ttacgaaaca ttgaacgtga ggatctgtat    240
aaagtgagag agagaaactc ggcggctgtg atccagcagc gacttgaatc caatctcgaa    300
aaacaatacg ccaagtacca cgccaaactg ctcaagaaag gactctcgga gcaagaggcg    360
catctcaagc tgcaagattc agccaaaccc ctcgtcttgg ctcttaacca gacgtttttt    420
tggaagttct ggctagccgg actgtttgcc ctagtcaagg acctctgtgg aatcgcctca    480
gctatggtgt cacgtgttct gatcgaatac attcaagaca gatatctcta caggggaca    540
gaccgggaac ctaaggtcgg ccgaggagtc ggcccctcga taggcctatt tctactggcc    600
gtaggagtca ctttcttctt caaccacatg ttctacaatg tcaagatggt tggagctcag    660
gctcgtgcag ctctggtggc cgtcatctac agcaagagta cccgtttgag cgccaagggc    720
cgagctcaat acaccacagg caagatcaca aacttggcag ctattgacgc acatcgagtt    780
gatctcagtt gtgaatcttt ccactacatt actatctttt tgcctgttgt gggttgtgcc    840
attgctgtac tcgtggtcaa cctcaaggtc gcagctctag ttggaattgc gaccatgatt    900
gtcttgatct ttgtcgtcgc aggcatcacc atcttctcta tgaagctgcg agccatcatt    960
gtcaagctca cggataagcg agtcacgtat atccgagaag ctctgcagtc gattagaatc   1020
atcaagtact acggctggga ggttccttac tgtgacaaga tcaagaaggt gcgtcttgac   1080
gagacccgta actacgccaa gatgggctcg attcgaggaa cagccattgg tatgtttcag   1140
gcactcccta ttttggcagg agcgttgtct ttcatcacct acgctgctct aggtcatgga   1200
actgatcctg ctcgaatgtt ctcttctctg acgcttttca atttactcct gcctgctctt   1260
gctgttcttc cccaggccct ccaggctgct ggagacgctc gagtggctct cagacgtatc   1320
cagcggttcc ttggggccga ggagtcgact cccactacag tttttgacgc tactcttgaa   1380
tctactgatg acgctgtgat tgtggaagac gcctcttca tctggccaga agttgtcgat   1440
gataagagcg acaaagagaa ggctaaagat gcaagaagg aggaaaagga taagaagaag   1500
gccgagaaga aggccaagaa ggcggccaag aaggcggcca aggagatcgc ggtggttgtg   1560
gaagaggagg tggaacacga aaagaccgag ggatccagtg agtctgaaaa gggtactctt   1620
aagtcgactt tcaagggctt caacaacctg tctttcaaaa tcaagcgggg tgaatttgtc   1680
gttgttaccg gtcccattgg ttctggaaag tcgtctcttc ttgctgccat cactggatct   1740
atggttttga caggcggttc cgtgcgagtg tcgtccacag agtggattgg atgtctggag   1800
ccgtggattc aaaacgccac agttcgagat aacattgtgt ttgggcgaaa attcgactct   1860
gaatggtata gaactgtggt tactgcctgt cagctgagcc aggatctcaa aataatgact   1920
cacggagaca ataccatgat tggagagcga ggcatcacag tttcgggcgg tcaaaaagct   1980
cgaatcaacc tcgcacgtgc tatatatgga aaccccgaga ttctcatcat ggacgacgtc   2040
ctgtcggctg tggacgctcg agtaggtgct ggtattgtgg acgattgtct tcgaggctta   2100
```

```
gccaagaact ccactcgaat tctggccacc catcagctgt ctgtgctgcc taaggctgat    2160
catgtgattt tcatggatgc cgaaggccag tttcatattg gtacgtacca agagctggag    2220
gctgacaatg agcagttcaa ggctcttttg gcggctggtt ccatgtccaa ggaggaggtg    2280
gttgctgtcg acgagactga ggttgttatt gaaggcgatc ttgaagacga ctgcgataac    2340
aaggaggagt atgaggatgc agctgagacc atttccattt tggcagatgc cactcaagag    2400
ctgcaaaagg tgaccactac agtctcggca tttgaggaga cgataacat gatggaggaa    2460 gaagagcgaa tgagagatgc agttggtttg catgtgtact ggcagtattt tcgtcaggcc    2520
aaccccagta gggtcaaggt aatgatgttc attggcatga tcttcatttc catgattgtg    2580
attgcctttc tgtttgtctt cacatctgta tggctctcgt tctggacagg tgaccgtttc    2640
catgcctcca gaaacttcta caccggaatt tacatcatgc tgggtattct tctgcttctt    2700
gctgtggcag atacatgat tgtcaatgag atcaactctg ccatggcagc aagaaatcta    2760
cacaatcatg ctttggactc ggtgttcgct gcacgaactt cttcttcga taccactcct    2820 cagggtcgta tcatcaaccg gttcacccga cacacagact ctctggataa cgagctggct    2880
atgcgattga ctatgttgtt cttggcgtc tccgcattct tctccaactt cctgcttact    2940
tgtgtctacg ttccttatgt gactcttgtg cttgtccctg tcggttttgt cttctacgtt    3000
tctctaggtt actaccgaaa gtcagctcgt gaagtcaagc gaattgactc cattgaacgg    3060
tcgcacatga tgagtgtctt caacgagtcc atttccggta tgcccgtcat catcatgtac    3120
aaggcccagc atcggctcat gaacaagctt caggctactc tcgatgatat ggacagtgcc    3180
tacttcctca ctgctgcaaa ccagcgatgg ctgtctctcc gtctggatgg tctgggttct    3240
ttggtcgttc tggtgccac tattcttgtt gctgtcggag tctttgatct cacccttcc    3300 aacatgggtc tgatcatttc cgcggcctcc tttatccccg aagtcatgtc tatggttgcc    3360
caggccgttg ctgaactcga aaactgcatg aacgccacag agcgaattct ttactacaag    3420
gacaacattc ctgctgaggc tgctcgagaa gtggacggta cagagctcga ccagcgaccc    3480
aactggcctg agcagggagc catcagcttc aacaatgtgt ccatgaagta ccgagatgga    3540
cttccttacg tgctcaagtc attgtctgtc gactttcagg aggacacaa ggtgggtatc    3600 tgtggacgaa caggagccgg taagagtacc atcttgcaga ctctgtatcg aattgtggag    3660
cttgctgagg gttctattac tattgatggt gttgacattt cgactattgg actgcatcag    3720
cttcggtctc agttgtccat cattccccag gagccagttt tgttcctggg caccatccgg    3780
tctaatttgg atcctctgga gcaatactct gatgctgagc tatggggttc tctacgacgg    3840
tctggacttc tcgatgaagg agagactgag ggtaagtttc atctggatca aaaggtggag    3900
gctgacggca gcaacttctc tctaggtgag cgacagctgc tgactctagc ccgagcactg    3960
cttagaaaca ccaaaatttt ggtgctggac gaagccacat caaatgtcga ctacaagacg    4020
gacaagctgg ttcaggagac catttcacgg gagtttggcc actgcacgat tctgtgtatc    4080
gcccatcgac tgcgaaccat tgccaagtat gatcgtattt tggtgcttga gtccggcgag    4140
atcaaccagt acgacacgcc ctggaacttg tacaacgaca aggagggtat tttccgaggt    4200
atgtgtgaca cctccgggtt gaacgaggta gacttcaaca agtaa                  4245
```

<210> SEQ ID NO 28
<211> LENGTH: 4245
<212> TYPE: DNA
<213> ORGANISM: Artificial sequence
<220> FEATURE:

<223> OTHER INFORMATION: YALI0E25201g CpO for Y. lipolitica

<400> SEQUENCE: 28

```
atgggtaaga ccgaggtcac tcaggagtct ctcgagtgcg gttccgtcac ctcctctctc      60
ggcaagaagc ccttctccat catcactctc ttcaccggcc gacggatccc tcccgtcccc     120
actgagaagc ccgactccgc tgaggagcga gccggcatcc tctccaagct gacctggcag     180
tggctctctc ctctgctcaa gaccggttac ctccgaaaca tcgagcgaga ggatctgtac     240
aaggtccgag agcgaaactc cgctgccgtt atccagcagc gacttgagtc caacctggag     300
aagcagtacg ccaagtacca cgccaagctc ctcaagaagg gtctgtctga gcaagaggcc     360
cacctcaagc tgcaggactc tgccaagccc cttgtcctgg ccctcaacca gaccttcttc     420
tggaagttct ggctcgctgg tctgttcgcc ctcgtcaagg acctctgtgg cattgcttcc     480
gccatggttt cccgagttct cattgagtac atccaggacc gataccctct accgaggtacc    540
gaccgagagc ccaaggtcgg ccgaggtgtc ggtccctcca tcggactctt cctgctggcc     600
gttggtgtca ctttcttctt caaccacatg ttctacaacg tcaagatggt tggtgcccag     660
gcccgagctg ccctcgtcgc tgtcatctac tccaagtcca cccgactgtc cgccaagggt     720
cgagcccagt acaccaccgg caagatcacc aacctcgccg ccattgatgc caccgagtc      780
gatctgtctt gcgagtcttt tcactacatc actatcttcc ttcccgtcgt cggctgcgcc     840
attgccgtcc tcgttgtcaa cctcaaggtt gctgctctcg tcggtattgc cactatgatt     900
gtcctcatct ttgtcgttgc tggtatcacc atcttctcca tgaagctccg agccatcatc     960
gtcaagctca ccgacaagcg agtcacctac atccgagagg ctctccagtc catccgaatc    1020
atcaagtact acggctggga ggttccctac tgcgacaaga ttaagaaggt ccgactcgac    1080
gagactcgaa actacgccaa gatgggctcc attcgaggaa ccgctattgg tatgttccag    1140
gctctcccca tcctcgccgg cgctctgtct tttatcacct acgccgccct cggtcacggc    1200
accgaccccg cccgaatgtt ctcttctctc accctcttca acctgctgct cccgctctt     1260
gccgttctcc cccaggccct ccaggccgct ggtgacgccc gagtcgccct gcgacgaatc    1320
cagcgattcc tcggtgctga ggagtccacc cccaccactg tcttcgatgc tactcttgag    1380
tctaccgacg acgccgtcat cgtcgaggac gcctccttca tttggcccga ggtcgttgac    1440
gacaagtccg acaaggagaa ggccaaggat gctaagaaag aggagaagga caagaagaag    1500
gctgagaaga agccaagaa ggccgctaag aaggcagcca aggagatcgc cgttgttgtt    1560
gaggaagagg tcgagcacga gaagaccgaa ggctcctccg agtccgagaa aggtaccctc    1620
aagtccacgt tcaagggttt caacaacctg tctttcaaga tcaagcgagg tgagttcgtt    1680
gtcgtcactg gtcccatcgg ctccggtaag tcctctctgc tcgctgccat taccggttcc    1740
atggttctga ccggtggttc tgtccgagtc tcttccaccg agtggatcgg ttgcctcgag    1800
ccttggatcc agaacgccac cgtccgagac aacattgtct tcggccgtaa gtttgactcc    1860
gagtggtacc gaaccgttgt caccgcctgc cagctctccc caggacctcaa gatcatgacc    1920
cacggcgata caccatgat tggtgagcga ggtatcactg tctccggtgg tcagaaggcc     1980
cgaatcaacc tggcccgcgc gatctacggt aaccccgaga ttctcatcat ggacgacgtc    2040
ctctccgccg tcgacgccag ggtcggagcc ggtatcgtcg atgactgtct gagaggcctc    2100
gccaagaact ctacccgaat cctcgccacc accagctct ctgttctccc caaggccgac    2160
cacgtcatct ttatggacgc cgagggtcag ttccacattg gcacctacca agagctcgag    2220
gctgataacg agcagttcaa ggctctcctc gctgccggct ctatgtccaa agaggaagtc    2280
```

-continued

```
gttgccgttg acgagactga ggttgtcatt gagggtgacc tcgaggacga ctgtgacaac    2340
aaggaagagt acgaggatgc tgccgagact atctccattc tcgccgacgc cacccaggag    2400
ctccagaagg ttaccaccac cgtttctgct tttgaggaga cgacaacat gatggaggaa     2460
gaagaacgaa tgcgagatgc cgtcggtctg cacgtctact ggcagtactt ccgacaggcc    2520
aaccccctctc gagtcaaggt catgatgttc attggtatga ttttcatctc catgattgtc   2580
attgccttcc tcttcgtctt cacctccgtc tggctctcct tttggaccgg tgaccgattc    2640
cacgcttccc gaaacttcta caccggcatc tacatcatgc tcggtatcct ccttctgctc    2700
gccgtcgccg gttacatgat cgtcaatgag atcaactctg ccatggccgc cgaaacctg    2760
cacaaccacg ccctcgactc cgtcttcgcc gctcgaactt ctttcttcga caccactccc    2820
cagggccgaa tcattaaccg attcaccccgg gacaccgact ccctcgataa cgaactggcc   2880
atgcgactca ccatgctctt tttcggtgtt ccgccttttt ctccaacttt cctcctcacc    2940
tgtgtctacg ttccctacgt caccctggtt cttgtcccccg ttggtttcgt cttctacgtt    3000
tccctcggtt actaccgaaa gtccgcccga gaggtcaagc gaatcgactc cattgagcga    3060
tcccacatga tgtccgtctt caacgagtcc atctccggta tgcccgttat catcatgtac    3120
aaggcccagc accgactcat gaacaagctc caggccaccc tcgacgacat ggactccgcc    3180
tacttcctga ccgctgccaa ccagcgatgg ctctccctcc gactggacgg tcttggctct    3240
cttgttgtcc tcgtcgccac cattcttgtc gccgtcggtg tctttgacct cacccccctcc    3300
aacatgggcc tcatcatctc tgctgcctct ttcatcccccg aggtcatgtc catggtcgcc    3360
caggccgttg ctgagctcga gaactgcatg aacgctaccg agcgaatcct ctactacaag    3420
gacaacatcc ccgccgaggc tgctcgagag gtcgacggta ccgagcttga tcagcgaccc    3480
aactggcccg agcagggcgc catctccttc aacaacgtgt ccatgaagta ccgagatggt    3540
ctgccctacg tcctcaagtc tctctccgtc gacttccagg gcggccacaa ggtcggtatc    3600
tgcggacgaa ccggtgccgg caagtccact atcctccaga ccctgtaccg aatcgtcgag    3660
ctggccgagg gctccatcac cattgatggt gtcgacatct ccaccattgg cctgcaccag    3720
ctccgatccc agctgtccat catcccccag gagcccgttc tgttccttgg caccatccga    3780
tccaacctcg atccccctcga gcagtactcc gacgccgagc tctggggttc tctccgacga    3840
tccggccttc tggacgaggg tgaaaccgag ggtaagttcc acctcgacca gaaggtcgag    3900
gccgatggtt ccaacttctc tctgggtgag cgacagctcc tcaccctcgc ccgagcccctt   3960
ctgcgaaaca ccaagattct tgttctcgac gaggctaccc caacgtcga ctacaagacc     4020
gataagctcg tccaggagac aatctcccga gagttcggtc actgcaccat tctctgtatc    4080
gcccaccgac tgcgaaccat cgctaagtac gaccgaattc tcgttctcga gtccggcgag    4140
atcaaccagt acgacacccc ctggaacctc tacaacgaca aggaaggtat cttccgaggc    4200
atgtgcgaca cctccggcct caacgaggtc gactttaata aataa                    4245
```

<210> SEQ ID NO 29
<211> LENGTH: 1414
<212> TYPE: PRT
<213> ORGANISM: Yarrowia lipolytica

<400> SEQUENCE: 29

Met Gly Lys Thr Glu Val Thr Gln Glu Ser Leu Glu Cys Gly Ser Val
1               5                   10                  15

Thr Ser Ser Leu Gly Lys Lys Pro Phe Ser Ile Ile Thr Leu Phe Thr

```
                    20                  25                  30
Gly Arg Arg Ile Pro Pro Val Pro Thr Glu Lys Pro Asp Ser Ala Glu
                35                  40                  45
Glu Arg Ala Gly Ile Leu Ser Lys Leu Thr Trp Gln Trp Leu Ser Pro
 50                  55                  60
Leu Leu Lys Thr Gly Tyr Leu Arg Asn Ile Glu Arg Glu Asp Leu Tyr
 65                  70                  75                  80
Lys Val Arg Glu Arg Asn Ser Ala Ala Val Ile Gln Gln Arg Leu Glu
                85                  90                  95
Ser Asn Leu Glu Lys Gln Tyr Ala Lys Tyr His Ala Lys Leu Leu Lys
                100                 105                 110
Lys Gly Leu Ser Glu Gln Glu Ala His Leu Lys Leu Gln Asp Ser Ala
                115                 120                 125
Lys Pro Leu Val Leu Ala Leu Asn Gln Thr Phe Phe Trp Lys Phe Trp
                130                 135                 140
Leu Ala Gly Leu Phe Ala Leu Val Lys Asp Leu Cys Gly Ile Ala Ser
145                 150                 155                 160
Ala Met Val Ser Arg Val Leu Ile Glu Tyr Ile Gln Asp Arg Tyr Leu
                165                 170                 175
Tyr Arg Gly Thr Asp Arg Glu Pro Lys Val Gly Arg Gly Val Gly Pro
                180                 185                 190
Ser Ile Gly Leu Phe Leu Leu Ala Val Gly Val Thr Phe Phe Phe Asn
                195                 200                 205
His Met Phe Tyr Asn Val Lys Met Val Gly Ala Gln Ala Arg Ala Ala
                210                 215                 220
Leu Val Ala Val Ile Tyr Ser Lys Ser Thr Arg Leu Ser Ala Lys Gly
225                 230                 235                 240
Arg Ala Gln Tyr Thr Thr Gly Lys Ile Thr Asn Leu Ala Ala Ile Asp
                245                 250                 255
Ala His Arg Val Asp Leu Ser Cys Glu Ser Phe His Tyr Ile Thr Ile
                260                 265                 270
Phe Leu Pro Val Val Gly Cys Ala Ile Ala Val Leu Val Val Asn Leu
                275                 280                 285
Lys Val Ala Ala Leu Val Gly Ile Ala Thr Met Ile Val Leu Ile Phe
                290                 295                 300
Val Val Ala Gly Ile Thr Ile Phe Ser Met Lys Leu Arg Ala Ile Ile
305                 310                 315                 320
Val Lys Leu Thr Asp Lys Arg Val Thr Tyr Ile Arg Glu Ala Leu Gln
                325                 330                 335
Ser Ile Arg Ile Ile Lys Tyr Tyr Gly Trp Glu Val Pro Tyr Cys Asp
                340                 345                 350
Lys Ile Lys Lys Val Arg Leu Asp Glu Thr Arg Asn Tyr Ala Lys Met
                355                 360                 365
Gly Ser Ile Arg Gly Thr Ala Ile Gly Met Phe Gln Ala Leu Pro Ile
                370                 375                 380
Leu Ala Gly Ala Leu Ser Phe Ile Thr Tyr Ala Ala Leu Gly His Gly
385                 390                 395                 400
Thr Asp Pro Ala Arg Met Phe Ser Ser Leu Thr Leu Phe Asn Leu Leu
                405                 410                 415
Leu Pro Ala Leu Ala Val Leu Pro Gln Ala Leu Gln Ala Ala Gly Asp
                420                 425                 430
Ala Arg Val Ala Leu Arg Arg Ile Gln Arg Phe Leu Gly Ala Glu Glu
                435                 440                 445
```

```
Ser Thr Pro Thr Thr Val Phe Asp Ala Thr Leu Glu Ser Thr Asp Asp
    450                 455                 460

Ala Val Ile Val Glu Asp Ala Ser Phe Ile Trp Pro Glu Val Val Asp
465                 470                 475                 480

Asp Lys Ser Asp Lys Glu Lys Ala Lys Asp Ala Lys Lys Glu Lys
                485                 490                 495

Asp Lys Lys Lys Ala Glu Lys Ala Lys Lys Ala Lys Lys Ala
            500                 505                 510

Ala Lys Glu Ile Ala Val Val Glu Glu Val Glu His Glu Lys
        515                 520                 525

Thr Glu Gly Ser Ser Glu Ser Glu Lys Gly Thr Leu Lys Ser Thr Phe
    530                 535                 540

Lys Gly Phe Asn Asn Leu Ser Phe Lys Ile Lys Arg Gly Glu Phe Val
545                 550                 555                 560

Val Val Thr Gly Pro Ile Gly Ser Gly Lys Ser Ser Leu Leu Ala Ala
                565                 570                 575

Ile Thr Gly Ser Met Val Leu Thr Gly Gly Ser Val Arg Val Ser Ser
                580                 585                 590

Thr Glu Trp Ile Gly Cys Leu Glu Pro Trp Ile Gln Asn Ala Thr Val
    595                 600                 605

Arg Asp Asn Ile Val Phe Gly Arg Lys Phe Asp Ser Glu Trp Tyr Arg
610                 615                 620

Thr Val Val Thr Ala Cys Gln Leu Ser Gln Asp Leu Lys Ile Met Thr
625                 630                 635                 640

His Gly Asp Asn Thr Met Ile Gly Glu Arg Gly Ile Thr Val Ser Gly
                645                 650                 655

Gly Gln Lys Ala Arg Ile Asn Leu Ala Arg Ala Ile Tyr Gly Asn Pro
            660                 665                 670

Glu Ile Leu Ile Met Asp Asp Val Leu Ser Ala Val Asp Ala Arg Val
        675                 680                 685

Gly Ala Gly Ile Val Asp Asp Cys Leu Arg Gly Leu Ala Lys Asn Ser
        690                 695                 700

Thr Arg Ile Leu Ala Thr His Gln Leu Ser Val Leu Pro Lys Ala Asp
705                 710                 715                 720

His Val Ile Phe Met Asp Ala Glu Gly Gln Phe His Ile Gly Thr Tyr
                725                 730                 735

Gln Glu Leu Glu Ala Asp Asn Glu Gln Phe Lys Ala Leu Leu Ala Ala
                740                 745                 750

Gly Ser Met Ser Lys Glu Glu Val Ala Val Asp Glu Thr Glu Val
        755                 760                 765

Val Ile Glu Gly Asp Leu Glu Asp Asp Cys Asp Asn Lys Glu Glu Tyr
770                 775                 780

Glu Asp Ala Ala Glu Thr Ile Ser Ile Leu Ala Asp Ala Thr Gln Glu
785                 790                 795                 800

Leu Gln Lys Val Thr Thr Val Ser Ala Phe Glu Glu Asn Asp Asn
                805                 810                 815

Met Met Glu Glu Glu Arg Met Arg Asp Ala Val Gly Leu His Val
            820                 825                 830

Tyr Trp Gln Tyr Phe Arg Gln Ala Asn Pro Ser Arg Val Lys Val Met
        835                 840                 845

Met Phe Ile Gly Met Ile Phe Ile Ser Met Ile Val Ile Ala Phe Leu
    850                 855                 860
```

-continued

Phe Val Phe Thr Ser Val Trp Leu Ser Phe Trp Thr Gly Asp Arg Phe
865                 870                 875                 880

His Ala Ser Arg Asn Phe Tyr Thr Gly Ile Tyr Ile Met Leu Gly Ile
            885                 890                 895

Leu Leu Leu Leu Ala Val Ala Gly Tyr Met Ile Val Asn Glu Ile Asn
            900                 905                 910

Ser Ala Met Ala Ala Arg Asn Leu His Asn His Ala Leu Asp Ser Val
            915                 920                 925

Phe Ala Ala Arg Thr Ser Phe Phe Asp Thr Thr Pro Gln Gly Arg Ile
930                 935                 940

Ile Asn Arg Phe Thr Arg Asp Thr Asp Ser Leu Asp Asn Glu Leu Ala
945                 950                 955                 960

Met Arg Leu Thr Met Leu Phe Phe Gly Val Ser Ala Phe Phe Ser Asn
            965                 970                 975

Phe Leu Leu Thr Cys Val Tyr Val Pro Tyr Val Thr Leu Val Leu Val
            980                 985                 990

Pro Val Gly Phe Val Phe Tyr Val Ser Leu Gly Tyr Tyr Arg Lys Ser
            995                 1000                1005

Ala Arg Glu Val Lys Arg Ile Asp Ser Ile Glu Arg Ser His Met
    1010                1015                1020

Met Ser Val Phe Asn Glu Ser Ile Ser Gly Met Pro Val Ile Ile
    1025                1030                1035

Met Tyr Lys Ala Gln His Arg Leu Met Asn Lys Leu Gln Ala Thr
    1040                1045                1050

Leu Asp Asp Met Asp Ser Ala Tyr Phe Leu Thr Ala Ala Asn Gln
    1055                1060                1065

Arg Trp Leu Ser Leu Arg Leu Asp Gly Leu Gly Ser Leu Val Val
    1070                1075                1080

Leu Val Ala Thr Ile Leu Val Ala Val Gly Val Phe Asp Leu Thr
    1085                1090                1095

Pro Ser Asn Met Gly Leu Ile Ile Ser Ala Ala Ser Phe Ile Pro
    1100                1105                1110

Glu Val Met Ser Met Val Ala Gln Ala Val Ala Glu Leu Glu Asn
    1115                1120                1125

Cys Met Asn Ala Thr Glu Arg Ile Leu Tyr Tyr Lys Asp Asn Ile
    1130                1135                1140

Pro Ala Glu Ala Ala Arg Glu Val Asp Gly Thr Glu Leu Asp Gln
    1145                1150                1155

Arg Pro Asn Trp Pro Glu Gln Gly Ala Ile Ser Phe Asn Asn Val
    1160                1165                1170

Ser Met Lys Tyr Arg Asp Gly Leu Pro Tyr Val Leu Lys Ser Leu
    1175                1180                1185

Ser Val Asp Phe Gln Gly Gly His Lys Val Gly Ile Cys Gly Arg
    1190                1195                1200

Thr Gly Ala Gly Lys Ser Thr Ile Leu Gln Thr Leu Tyr Arg Ile
    1205                1210                1215

Val Glu Leu Ala Glu Gly Ser Ile Thr Ile Asp Gly Val Asp Ile
    1220                1225                1230

Ser Thr Ile Gly Leu His Gln Leu Arg Ser Gln Leu Ser Ile Ile
    1235                1240                1245

Pro Gln Glu Pro Val Leu Phe Leu Gly Thr Ile Arg Ser Asn Leu
    1250                1255                1260

Asp Pro Leu Glu Gln Tyr Ser Asp Ala Glu Leu Trp Gly Ser Leu

```
                1265                1270                1275
Arg Arg Ser Gly Leu Leu Asp Glu Gly Glu Thr Glu Gly Lys Phe
        1280                1285                1290

His Leu Asp Gln Lys Val Glu Ala Asp Gly Ser Asn Phe Ser Leu
        1295                1300                1305

Gly Glu Arg Gln Leu Leu Thr Leu Ala Arg Ala Leu Leu Arg Asn
        1310                1315                1320

Thr Lys Ile Leu Val Leu Asp Glu Ala Thr Ser Asn Val Asp Tyr
        1325                1330                1335

Lys Thr Asp Lys Leu Val Gln Glu Thr Ile Ser Arg Glu Phe Gly
        1340                1345                1350

His Cys Thr Ile Leu Cys Ile Ala His Arg Leu Arg Thr Ile Ala
        1355                1360                1365

Lys Tyr Asp Arg Ile Leu Val Leu Glu Ser Gly Glu Ile Asn Gln
        1370                1375                1380

Tyr Asp Thr Pro Trp Asn Leu Tyr Asn Asp Lys Glu Gly Ile Phe
        1385                1390                1395

Arg Gly Met Cys Asp Thr Ser Gly Leu Asn Glu Val Asp Phe Asn
        1400                1405                1410

Lys

<210> SEQ ID NO 30
<211> LENGTH: 1000
<212> TYPE: DNA
<213> ORGANISM: Yarrowia lipolytica

<400> SEQUENCE: 30
cggttgagag ttcaagaaca cgaccaagta accccgagaa agtgtcgatg gatacagaga      60
aaacaatatc gcagatattg acaacaaact tgcaacgaga gccctctaca tgctccaata     120
ttcttcttcc agacctaccc gttcacacaa ctacaagttg ccgccttaaa caacaacgtg     180
gtcaactccg gagttaacag aagcataata atgtgatgga atttggaggt tggggagaga     240
cagtttggac cggagacacg ccacggggaa atcatcataa acattggtaa atgccaaaa      300
aaaatttata catggtagca aaagcatcct ggagaactcc taagtatgtc agggtcccaa     360
aaacctcgtt aatggaggcc tgcggacttc ttccgtgaca ttgtgaacca ttaatacaac     420
ctgaaaagac catctgcaaa acaccagtga tagtggttcc aacgcaactt cgtgcacact     480
caacgctacc actgctagac ctaccgccgt tagacctatt gtatcgccgc caccgttctt     540
aaatgcagat gaagtaaaca ctgccgttcg gtccaataat taatgttgct ccgccatgct     600
cagttttttt tcttttcttt cggcaaaata accttcgcag tcatgtgaga tatcgcacga     660
caagatgtga ctaacatgcc aacggcggct gcccccaagg tgtatatgag taccaaatta     720
gggcatgata caagaatacc tttcgaaaag ccggaacaag ataaagcagc caacccctta     780
taacggccag ctagcgccaa acttgctcgc cccgagcccc accgcttcct catccgtacg     840
ccatttcgtg ccacgtatcc agaaagttct actcccagca cagggttagg ggtgttgcca     900
ttctgggtca ctccccacca ccacagcatg tttttttcctc tctcccgaca accacaactc     960
tctagtttac actaaccaca cacgacacca attttaaaaa                          1000

<210> SEQ ID NO 31
<211> LENGTH: 300
<212> TYPE: DNA
<213> ORGANISM: Yarrowia lipolytica
```

<400> SEQUENCE: 31

```
atgcaaacca agtaatttat tgtgtagtct aggattgaca tttgattacc gtgtacatta      60
aatgaatgat tgtaaattga agaggaagt gtagcaatgg ttgaatgggg agtaatgggt     120
tactgtaatt gcatgtccca ccttctttgc accgttcttg ttgtatacag tacaatacat    180
acataccta tgtatgtttt ttgtgaatat gatgagtcta ctactacagt aaatcagctt     240
tgatccctgc cagaatgtgt gtacacagta tgggactctc atccctgta caatataata    300
```

<210> SEQ ID NO 32
<211> LENGTH: 912
<212> TYPE: DNA
<213> ORGANISM: Artificial sequence
<220> FEATURE:
<223> OTHER INFORMATION: carG nucleic acid sequence codon optimized for Y. lipolitica

<400> SEQUENCE: 32

```
atgctcaact ctcacaaccg aaccgaggag cgatccaccg aggatattat tctcgagcct    60
tacacctacc tcatttctca gcccggaaag gacattcgag ctaagctcat ttctgccttt   120
gacctctggc tgcacgttcc taaggatgtt ctttgcgtca tcaacaagat tatcggtatg   180
ctgcacaacg cctctcttat gattgacgat gttcaggacg actctgatct ccgacgagga   240
gtccccgttg ctcaccacat ttacggtgtc cctcagacta ttaacaccgc taactacgtg   300
attttcctcg cccttcagga ggttatgaag ctgaacatcc cttctatgat gcaggtgtgt   360
accgaggagc ttattaacct ccaccgaggt cagggaattg agctgtactg gcagagattcc   420
ctcacttgtc ccactgagga ggagtacatt gatatggtta acaacaagac ctctggcctc   480
cttcgacttg ccgtccgact gatgcaggct gcttctgagt ccgacatcga ctacacccct   540
ctcgtcaaca ttatcggaat tcacttccag gttcgagatg actacatgaa cctccagtcc   600
acctcttaca ctaacaacaa gggcttttgc gaggacctga ccgagggaaa gttctccttc   660
cctattattc acgctattcg aaaggacccc tctaaccgac agctcctgaa cattatctct   720
cagaagccca cctccattga ggttaagaag tacgctcttg aggtgatccg aaaggctgga   780
tcttttgagt acgttcgaga gttccttcga cagaaggagg ctgagtccct gaaggagatc   840
aagcgacttg gcggcaaccc tctcctcgag aagtacattg agactattcg agtcgaggct   900
actaacgact aa                                                        912
```

<210> SEQ ID NO 33
<211> LENGTH: 1419
<212> TYPE: DNA
<213> ORGANISM: Artificial sequence
<220> FEATURE:
<223> OTHER INFORMATION: UGT2_6b CpO for Y. lipolitica

<400> SEQUENCE: 33

```
atggctactt ccgactccat tgtcgacgac cgaaagaagc tccacattgt catgttcccc    60
tggctcgcct ttggccacat cattccctac ctcgagcttt ccaagctcat gcccagaag   120
ggccacaagg tttctttcct ctccaccacc aagaacattg accgactctc ctcccacatc   180
tctcctctca tcaacgttgt ccagctcacc ctcccccgag tccaggagct gcccgaggac   240
gccgaggcca ccaccgatgt ccaccccgag atatcccct acctcaagaa ggcctccgac   300
ggtctgcagc ccgaggtcac cgagttcctc gagcagcact ctcccgactg gatcatctac   360
gactacaccc actactggct cccctccatt gccaccaagc acggtgtctc tcgagcccac   420
```

```
ttctccgtca ccaccccctg ggccattgcc tacatgggcc ccactgctga cgccatgatc      480
aacggttccg atggccgaac caccccgag gacttcactg tccctcccaa gtggttcccc       540
ttccccacca aggtctgctg gcgaaagcac gatctggccc gactcgttcc ctacaaggcc      600
cccggtatct ccgacggcta ccgaatgggt ctggtcatca agggctgcga ctgtctgctc      660
tccaagacct accacgagtt tggcacccag tggctccgac tcctcgagac tctccaccga      720
aagcccgtca tccccgtcgg tctgctccct ccctccatcc ccggctccga caaggacgac      780
tcttgggttt ccatcaagga gtggctcgac ggccaggaga agggctctgt tgtctacgtt      840
gctctcggtt ccgaggttct cgtcacccag gacgaggttg ttgagctggc ccacggtctg      900
gagctgtccg gcctcccctt cgtctgggct taccgaaacc ccaagggtcc cgccaagtcc      960
gactccgtcg agcttcccga tggtttcgtc gagcgagtcc gagatcgagg tctggtctgg     1020
acctcttggg ctccccagct ccgaatcctc tcccacgagt ccgtctgtgg tttcctcacc     1080
cactgcggtt ccggctccat cgtcgagggt ctgatgttcg ccaccccct catcatgctc      1140 cccatcttcg gtgaccagcc cctcaacgcc cgactccttg aggacaagca ggtcggtatc     1200
gagatccccc gaaacgaaga ggacggttcc ttcacccgag actctgttgc tgagtctctc     1260
cgactcgtca tggtcgagga gagggtaag atctaccgag agaaggccaa ggagatgtcc      1320
aagctgttcg gtgacaagga tctccaggac cagtacgtcg acgactttgt cgagtacctc     1380
cagaagcacc gacgagctgt tgccattgac cacgagtct                            1419
```

<210> SEQ ID NO 34
<211> LENGTH: 1341
<212> TYPE: DNA
<213> ORGANISM: Artificial sequence
<220> FEATURE:
<223> OTHER INFORMATION: RT18 nucleic acid sequence CpO for Y.
      lipolitica

<400> SEQUENCE: 34

```
atgtccacca ccctcaaggt cctcatgttc cccttcctcg cttacggcca catctctccc       60
tacctcaacg ttgccaagaa gctcgccgac cgaggcttcc tcatctacct ctgttccacc      120
cccatcaacc tcaagtccac catcaacaag atccccgaga gtacgccga ctccatccag       180 ctcatcgaac tccatctccc cgagcttccc gagctgcctc cccactacca caccaccaac     240
ggtctgcctc ccaacctcaa ccacatcctc cgacgagccc tcaagatgtc caagcccaac     300
ttctccaaga tcatgcagaa cctgaagccc gatctgctca tctacgacat tctccagcag     360
tgggccgagg atgtcgccac cgagcttaac atccccgccg tcaagctgct cacctctggt     420
gttgctgttt tctcttactt cttcaacctc accaagaagc ccgaggtcga gttcccctac      480
cccgctatct acctccgaaa gatcgagctg tccgatggt gcgagactct gtccaagcac       540
aacaaggaag gtgaggagca cgacgacggc ctcgcctacg gcaacatgca gatcatgctc     600
atgtccactt ccaagatcct cgaggccaag tacattgact actgcattga gctgaccaac     660
tggaaggtcg tccccgtcgg ctctctcgtc caggactcca tcaccaacga cgccgctgac     720
gacgacatgg aactcattga ctggctcggt actaaggacg agaactccac cgtctttgtc     780
tcttttggct ccgagtactt cctctccaaa gaggacgttg aagaggttgc cttcggtctg     840
gagctgtcca acgtcaactt catctggggtt gtccgattcc caagggtga ggagaagaac    900 ctcgaggacg ttctgcccaa gggcttcttc gagcgaatcg gtgagcgagg ccgagtcctc     960
gacaagtttg ctccccagcc ccgaattctc aaccaccct ctaccggtgg tttcatctct     1020
```

```
cactgtggct ggaactccgc catggagtcc attgactttg gtgtccccat tgtcgccatg    1080
cccatgcagc tcgaccagcc catgaacgcc cgactcattg tcgagcttgg tgttgccgtc    1140
gagattgtcc gagatgatga tggtaagatc taccgaggtg agattgctga gactctcaag    1200
ggtgtcatca ccggcgagat tggtgagatc ctccgagcca aggtccgaga catctccaag    1260
aacctcaagg ccatcaagga cgaggagatg gacgttgctg cccaggagct gatccagctc    1320
tgccgaaact ccaataaata a                                              1341
```

STEVIOL GLYCOSIDE TRANSPORT

CROSS-REFERENCE TO RELATED APPLICATIONS

This application is a divisional of U.S. application Ser. No. 15/751,674, filed on 9 Feb. 2018, which is a 371 National Stage Application of PCT/EP2016/069356, filed 15 Aug. 2016, and claims benefit to U.S. Provisional Application No. 62/204,702, filed 13 Aug. 2015.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2919208-344002_ST25.txt" created on 21 Oct. 2021, and 72,901 bytes in size) is submitted concurrently with the instant application, and the entire contents of the Sequence Listing are incorporated herein by reference.

FIELD OF THE INVENTION

The present invention relates to a recombinant host capable of producing a steviol glycoside. The invention also relates to a process for the preparation of a steviol glycoside using such a recombinant host. The invention also relates to a fermentation broth comprising a steviol glycoside, a steviol glycoside and to a composition comprising two or more steviol glycosides. The invention further relates to a foodstuff, feed or beverage which comprises a steviol glycoside or a composition comprising two or more steviol glycosides.

DESCRIPTION OF RELATED ART

The leaves of the perennial herb, *Stevia rebaudiana* Bert., accumulate quantities of intensely sweet compounds known as steviol glycosides. Whilst the biological function of these compounds is unclear, they have commercial significance as alternative high potency sweeteners.

These sweet steviol glycosides have functional and sensory properties that appear to be superior to those of many high potency sweeteners. In addition, studies suggest that stevioside can reduce blood glucose levels in Type II diabetics and can reduce blood pressure in mildly hypertensive patients.

Steviol glycosides accumulate in Stevia leaves where they may comprise from 10 to 20% of the leaf dry weight. Stevioside and rebaudioside A are both heat and pH stable and suitable for use in carbonated beverages and many other foods. Stevioside is between 110 and 270 times sweeter than sucrose, rebaudioside A between 150 and 320 times sweeter than sucrose. In addition, rebaudioside D is also a high-potency diterpene glycoside sweetener which accumulates in Stevia leaves. It may be about 200 times sweeter than sucrose. Rebaudioside M is a further high-potency diterpene glycoside sweetener. It is present in trace amounts in certain stevia variety leaves, but has been suggested to have a superior taste profile.

Steviol glycosides have traditionally been extracted from the Stevia plant. In Stevia, (−)-kaurenoic acid, an intermediate in gibberellic acid (GA) biosynthesis, is converted into the tetracyclic diterpene steviol, which then proceeds through a multi-step glycosylation pathway to form the various steviol glycosides. However, yields may be variable and affected by agriculture and environmental conditions. Also, Stevia cultivation requires substantial land area, a long time prior to harvest, intensive labour and additional costs for the extraction and purification of the glycosides.

More recently, interest has grown in producing steviol glycosides using fermentative processes. WO2013/110673 and WO2015/007748 describe microorganisms that may be used to produce at least the steviol glycosides rebaudioside A, rebaudioside D and rebaudioside M.

Further improvement of such microorganisms is desirable in order that higher amounts of steviol glycosides may be produced and/or additional or new steviol glycosides and/or higher amounts of specific steviol glycosides and/or mixtures of steviol glycosides having desired ratios of different steviol glycosides.

SUMMARY OF THE INVENTION

The present invention is based on the identification of a protein which is capable of mediating steviol glycoside transport.

Accordingly, the protein may be overexpressed in a recombinant host (such as a microbial cell) in order to increase steviol glycoside transport out of the host. Alternatively, a host (such as a microbial cell) may be modified so as to express less of the protein than a corresponding non-modified version of the host. In this case, more steviol glycoside may be retained within the host which is then glycosylated to a steviol glycoside comprising a higher number of sugar moieties.

Thus, the invention relates to a recombinant host, for example a cell such as a microbial cell, which produces steviol glycoside outside the host to a greater degree than a corresponding host not overexpressing the protein. This may facilitate easier recovery of steviol glycosides. The invention also relates to a recombinant host capable of producing a steviol glycoside which overexpresses a heterologous polypeptide which mediates steviol glycoside transport.

Accordingly, the invention relates to a recombinant host capable of producing a steviol glycoside which overexpresses a polypeptide which mediates steviol glycoside transport and which polypeptide comprises the amino acid sequence set forth in SEQ ID NO: 29 or an amino acid sequence having at least about 50% sequence identity thereto.

The invention also relates to a recombinant host capable of producing a steviol glycoside which has been modified, preferably in its genome, to result in a deficiency in the production of a polypeptide which mediates steviol glycoside transport and which polypeptide comprises the amino acid sequence set forth in SEQ ID NO: 29 or an amino acid sequence having at least about 50% sequence identity thereto.

The invention also relates to a recombinant host which comprises steviol glycosides (inside and/or outside the host) having a higher or lower average glycosylation number than a corresponding host not modified according to the invention.

The invention also relates to:
a process for the preparation of a steviol glycoside which comprises fermenting a recombinant host according to any one of the preceding claims in a suitable fermentation medium and, optionally, recovering the steviol glycoside;
a fermentation broth comprising a steviol glycoside obtainable by a process of the invention;

a steviol glycoside obtained by a process or a fermentation broth of the invention;

a composition comprising two or more steviol glycosides of the invention or obtainable by a process of the invention;

a foodstuff, feed or beverage which comprises a steviol glycoside or a composition of the invention.

DESCRIPTION OF THE SEQUENCE LISTING

Figure 1:
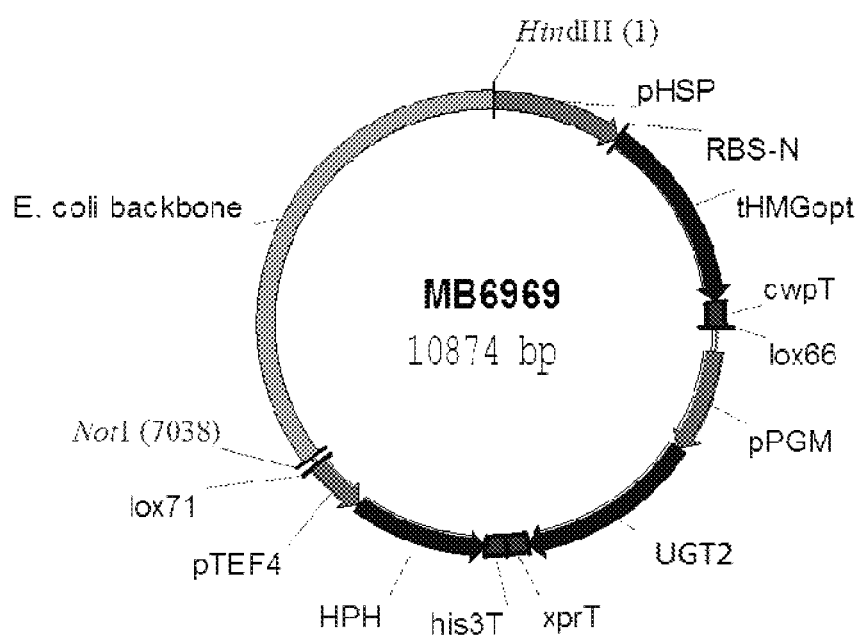
FIG. 1 sets out a schematic representation of the plasmid MB6969, encoding tHMG, UGT2_1a, HPH.

A description of the sequences is set out in Table 14. Sequences described herein may be defined with reference to the sequence listing or with reference to the database accession numbers also set out in Table 14.

DETAILED DESCRIPTION OF THE INVENTION

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The invention relates to the identification of a polypeptide which is capable of mediating steviol glycoside transport. Such a polypeptide may directly mediate steviol glycoside transport, i.e.

may be a transporter protein, or may indirectly mediate steviol glycoside transport. Such a polypeptide may be capable of mediating transport of one or more steviol glycoside.

The invention relates to a recombinant host either overexpressing or having reduced expression of such a polypeptide. The terms recombinant host or recombinant cell may, depending on the context, be used interchangeably.

Such a polypeptide as described herein may be overexpressed in a recombinant host, such as a recombinant host cell, capable of producing one or more steviol glycosides. Such a cell may be capable of producing more of one or more steviol glycosides external to the cell than a corresponding cell which does not overexpress the polypeptide. That is to say, a recombinant cell according to the invention may have increased or decreased steviol glycoside transport in a comparison with a corresponding non-recombinant cell.

Accordingly, the invention provides a recombinant host capable of producing a steviol glycoside which overexpresses a polypeptide, the polypeptide being one which is capable of mediating steviol glycoside transport and which polypeptide comprises the amino acid sequence set forth in SEQ ID NO: 29 or an amino acid sequence having at least about 50% sequence identity thereto.

The expression of such a polypeptide may also be modified in a host, such as a recombinant host cell, such that it is reduced compared to a corresponding cell which has not been similarly modified. In this way, the amount of one or more steviol glycosides outside the cell may be reduced in comparison with a corresponding cell which has not been similarly modified.

This may allow for increased glycosylation of one or more steviol glycosides within the cell compared with a corresponding cell which has not been similarly modified. Such a host may thus comprise steviol glycosides having a higher average glycosylation number compared with a corresponding cell which has not been similarly modified.

Accordingly, the invention provides a recombinant host capable of producing a steviol glycoside which has been modified, preferably in its genome, to result in a deficiency in the production of a polypeptide, the polypeptide being one which is capable of mediating steviol glycoside transport and which polypeptide comprises the amino acid sequence set forth in SEQ ID NO: 29 or an amino acid sequence having at least about 50% sequence identity thereto.

A host cell of the invention is a recombinant host cell. "Recombinant" in this sense means that the host cell is a non-naturally occurring host cell, for example modified by introduction of one or more nucleic acids using recombinant techniques. A nucleic acid used to modify a host cell to arrive at a recombinant host cell of the invention may be a naturally-occurring nucleic acid or a non-naturally occurring nucleic acid.

Thus, when used in reference to a host of the invention, "recombinant" indicates that a cell has been modified by the introduction of one or more heterologous nucleic acid or protein or the alteration of a native nucleic acid or protein, or that the cell is derived from a cell so modified. The term "heterologous" as used herein refers to nucleic acid or amino acid sequences not naturally occurring in a host cell. In other words, the nucleic acid or amino acid sequence is not identical to that naturally found in the host cell.

The invention relates to a recombinant host capable of producing a steviol glycoside which overexpresses a heterologous polypeptide which mediates steviol glycoside transport. Such a heterologous polypeptide may be obtained from or derived from a genus or species other than that of the host. Accordingly, if the recombinant host is a yeast, the heterologous polypeptide which mediates steviol glycoside transport may be obtained from or derived from a different genus or species of yeast.

For example, if the host cell is a *Saccharomyces* (e.g., *S. cerevisiae, S. bayanus, S. pastorianus, S. carlsbergensis*), the heterologous polypeptide which mediates steviol glycoside transport may be obtained from or derived from a *Candida* (e.g., *C. krusei, C. revkaufi, C. pulcherrima, C. tropicalis, C. utilis*), an *Issatchenkia* (eg. *I. orientalis*) or a *Yarrowia* (e.g., *Y. lipolytica* (formerly classified as *Candida lipolytica*)).

For example, if the host cell is a *Candida* (e.g., *C. krusei, C. revkaufi, C. pulcherrima, C. tropicalis, C. utilis*), the heterologous polypeptide which mediates steviol glycoside transport may be obtained from or derived from a *Saccharomyces* (e.g., *S. cerevisiae, S. bayanus, S. pastorianus, S. carlsbergensis*), an *Issatchenkia* (eg. *I. orientalis*) or a *Yarrowia* (e.g., *Y. lipolytica* (formerly classified as *Candida lipolytica*)).

For example, if the host cell is an *Issatchenkia* (eg. *I. orientalis*), the heterologous polypeptide which mediates steviol glycoside transport may be obtained or derived from a *Saccharomyces* (e.g., *S. cerevisiae, S. bayanus, S. pastorianus, S. carlsbergensis*), a *Candida* (e.g., *C. krusei, C. revkaufi, C. pulcherrima, C. tropicalis, C. utilis*) or a *Yarrowia* (e.g., *Y. lipolytica* (formerly classified as *Candida lipolytica*)).

For example, if the host cell is a *Yarrowia* (e.g., *Y. lipolytica* (formerly classified as *Candida* lipolytica)), the heterologous polypeptide which mediates steviol glycoside transport may be obtained from or derived from a *Saccharomyces* (e.g., *S. cerevisiae, S. bayanus, S. pastorianus, S. carlsbergensis*). a *Candida* (e.g., *C. krusei, C. revkaufi, C. pulcherrima, C. tropicalis, C. utilis*) or an *Issatchenkia* (eg. *I. orientalis*).

If the host cell is *Saccharomyces cerevisiae*, the heterologous polypeptide which mediates steviol glycoside transport may be obtained from or derived from *Yarrowia lipolytica* (formerly classified as *Candida lipolytica*)), *Candida krusei* or *Issatchenkia orientalis*.

If the host cell is *Yarrowia lipolytica*, the heterologous polypeptide which mediates steviol glycoside transport may be obtained from or derived from *Saccharomyces cerevisiae*, *Yarrowia lipolytica* (formerly classified as *Candida lipolytica*)) or *Candida krusei* or *Issatchenkia orientalis*.

If the host cell is *Candida krusei* or *Issatchenkia orientalis*, the heterologous polypeptide which mediates steviol glycoside transport may be obtained from or derived from *Saccharomyces cerevisiae* or *Yarrowia lipolytica*.

The term "derived from" also includes the terms "originated from," "obtained from," "obtainable from," "isolated from," and "created from," and generally indicates that one specified material find its origin in another specified material or has features that can be described with reference to the another specified material. As used herein, a substance (e.g., a nucleic acid molecule or polypeptide) "derived from" a microorganism may indicate that the substance is native to that microorganism or is a substance native to that microorganism, but may also indicate a substance that has been altered from a native version.

Thus, for example, a recombinant cell may express a polypeptide as defined herein not found within the native (non-recombinant) form of the cell. Alternatively, a recombinant cell may be modified so as to express a native gene encoding a polypeptide as defined herein to a greater degree than takes place within the native "non-recombinant" form of the cell.

Alternatively, a recombinant cell may be modified so as to express a native gene encoding a polypeptide as defined herein to a lesser degree than takes place within the native "non-recombinant" form of the cell.

In a cell of the invention, a polypeptide as defined herein may be overexpressed. Herein, "overexpressed", "overexpression" or the like implies that the recombinant host cell expresses more of the polypeptide than a corresponding cell which does not overexpress the polypeptide or, alternatively, that the polypeptide is expressed in a cell which would not typically express that protein. Alternatively, overexpression may be achieved by expressing a variant polypeptide having a higher specific activity.

A recombinant cell of the invention cell may be modified, preferably in its genome, to result in a deficiency in the production of a polypeptide as defined herein.

Such a cell may be from a parent host cell and be modified, preferably in its genome, if compared to the parent host cell to obtain a different genotype and/or a different phenotype if compared to the parent host cell from which it is derived.

Such a cell which has been modified, preferably in its genome, to result in a deficiency in the production of a polypeptide as defined herein, is a mutant host cell which has been modified, preferably in its genome, to result in a phenotypic feature wherein the cell: a) produces less of the product or produces substantially no product and/or b) produces a product having a decreased activity or decreased specific activity or a product having no activity or no specific activity and combinations of one or more of these possibilities as compared to the parent microbial host cell that has not been modified, when analyzed under the same conditions.

The term "recombinant" is synonymous with "genetically modified".

Such a recombinant host may be a full or partial knockout of a nucleic acid sequence encoding a polypeptide as described herein.

The invention thus concerns recombinant hosts overexpressing or deficient in a polypeptide identified as having steviol glycoside transport mediating activity: typically, the host is one which may be used for the production of steviol glycosides. The ability of a given recombinant host to produce a steviol glycoside may be a property of the host in non-recombinant form or may be a result of the introduction of one or more recombinant nucleic acid sequences (i.e. encoding enzymes leading to the production of a steviol glycoside).

For the purpose of this invention, a polypeptide having steviol glycoside transport mediating activity (i.e. a polypeptide which mediates steviol glycoside transport) is one which has an effect on transport of one or more steviol glycosides across a cell membrane. The effect may be direct, i.e. the polypeptide may be a transporter protein or comprise a functional transporter region. Alternatively, the effect may be indirect, i.e. the polypeptide is not a transporter protein, but its activity nevertheless has an effect on steviol glycoside transport.

Typically, the effect will be such that increasing the level of expression of the polypeptide increases the amount of transport of one or more steviol glycosides across the membrane of a cell (in comparison with a corresponding cell having a lower level of expression of the polypeptide). Conversely, decreasing the level of expression of the polypeptide may decrease the amount of transport of one or more steviol glycosides across the membrane of a cell (in comparison with a corresponding cell having a higher level of expression of the polypeptide).

Typically, a recombinant host of the invention is capable of producing a steviol glycoside. For example, a recombinant host of the invention may be capable of producing one or more of, for example but not limited to, steviol-13-monoside, steviol-19-monoside, 13-[(β-D-Glucopyranosyl) oxy)kaur-16-en-18-oic acid 2-O-β-D-glucopyranosyl-β-D-glucopyranosyl ester, rubusoside, stevioside, steviol-19-diside, steviolbioside, rebA, rebB, rebC, rebD, rebE or rebM. A recombinant host of the invention may be capable of producing one or more of the steviol glycosides set out in Ceunen and Geuns, Journal of Natural Products 76(6), 1201-1228, 2013.

Thus, a cell of the invention may be one in which the amount of total amount of steviol glycosides outside the cell as compared with inside the cell is greater or less than compared with a corresponding cell which either does not overexpress or does not have a reduced level of expression of a cell of the invention.

Alternatively, a cell of the invention may have the same total amount of steviol glycosides outside the cell as compared with inside the cell compared with a corresponding cell which either does not overexpress or does not have a reduced level of expression of a cell of the invention, but may have an altered distribution of steviol glycosides inside and outside the cell.

Thus, a recombinant host of the invention is capable of producing a steviol glycoside. For example, a recombinant host of the invention may be capable of producing one or more of, for example, steviol-13-monoside, steviol-19-monoside, 13-[(β-D-Glucopyranosyl)oxy)kaur-16-en-18-oic acid 2-O-β-D-glucopyranosyl-β-D-glucopyranosyl ester, rubusoside, stevioside, steviol-19-diside, steviolbioside, rebA, rebB, rebC, rebD, rebE or rebM.

Thus, a recombinant host of the invention may be one in which at least about 10%, at least about 20%, at least about 30%, at least about 40%, at least about 50% of the rebA produced by the cell is outside the cell.

Thus, a recombinant host of the invention may be one in which at least about 10%, at least about 20%, at least about 30%, at least about 40%, at least about 50% of the rebD produced by the cell is outside the cell.

Thus, a recombinant host of the invention may be one in which at least about 10%, at least about 20%, at least about 30%, at least about 40%, at least about 50% of the rebM produced by the cell is outside the cell.

A recombinant cell of the invention may be one in which no more than about 50%, no more than about 40%, no more than about 30%, no more than about 20%, no more than about 10% of the rebA produced by the cell is outside the cell.

A recombinant cell of the invention may be one in which no more than about 50%, no more than about 40%, no more than about 30%, no more than about 20%, no more than about 10% of the rebD produced by the cell is outside the cell.

A recombinant cell of the invention may be one in which no more than about 50%, no more than about 40%, no more than about 30%, no more than about 20%, no more than about 10% of the rebM produced by the cell is outside the cell.

A recombinant cell of the invention may be one where the average glycosylation number of the steviol glycosides is at least 3, at least 4, at least 5, at least 6 or more. The average glycosylation number may be increased or decreased in comparison with a corresponding cell not modified according to the invention. For example, average glycosylation may decrease when a polypeptide as described herein is overexpressed. For example, average glycosylation may increase (in particular in a cell itself) when expression of a polypeptide of the invention is reduced.

The average glycosylation may refer to that in the supernatant of a recombinant cell of the invention or to the average glycosylation in the broth (pellet+supernatant).

The invention thus provides a recombinant cell capable of producing a steviol glycoside either overexpressing or deficient in the expression of a polypeptide comprising the amino acid sequence set forth in SEQ ID NO: 29 or an amino acid sequence having at least about 50% sequence identity thereto. Such an amino acid sequence has an effect of steviol glycoside transport, i.e. is a mediator of steviol glycoside transport.

The polypeptide may also be defined as one comprising the following amino acid sequence (or an amino acid sequence having at least about 45% sequence identity thereto):

```
                                          (SEQ ID NO: 29)
MGKTEVTQESLECGSVTSSLGKKPFSIITLFTGRRIPPVPTEKPDSAEER

AGILSKLTWQWLSPLLKTGYLRNIEREDLYKVRERNSAAVIQQRLESNLE

KQYAKYHAKLLKKGLSEQEAHLKLQDSAKPLVLALNQTFFWKFWLAGLFA

LVKDLCGIASAMVSRVLIEYIQDRYLYRGTDREPKVGRGVGPSIGLFLLA

VGVTFFFNHMFYNVKMVGAQARAALVAVIYSKSTRLSAKGRAQYTTGKIT

NLAAIDAHRVDLSCESFHYITIFLPVVGCAIAVLVVNLKVAALVGIATMI

VLIFVVAGITIFSMKLRAIIVKLTDKRVTYIREALQSIRIIKYYGWEVPY

CDKIKKVRLDETRNYAKMGSIRGTAIGMFQALPILAGALSFITYAALGHG

TDPARMFSSLTLFNLLLPALAVLPQALQAAGDARVALRRIQRFLGAEEST

PTTVFDATLESTDDAVIVEDASFIWPEVVDDKSDKEKAKDAKKEEKDKKK

AEKKAKKAAKKAAKEIAVVVEEEVEHEKTEGSSESEKGTLKSTFKGFNNL

SFKIKRGEFVVVTGPIGSGKSSLLAAITGSMVLTGGSVRVSSTEWIGCLE

PWIQNATVRDNIVFGRKFDSEWYRTVVTACQLSQDLKIMTHGDNTMIGER
```

-continued

GITVSGGQKARINLARAIYGNPEILIMDDVLSAVDARVGAGIVDDCLRGL

AKNSTRILATHQLSVLPKADHVIFMDAEGQPHIGTYQELEADNEQFKALL

AAGSMSKEEVVAVDETEVVIEGDLEDDCDNKEEYEDAAETISILADATQE

LQKVTTTVSAFEENDNMMEEEERMRDAVGLHVYWQYFRQANPSRVKVMMF

IGMIFISMIVIAFLFVFTSVWLSFWTGDRFHASRNFYTGIYIMLGILLLL

AVAGYMIVNEINSAMAARNLHNHALDSVFAARTSFFDTTPQGRIINRFTR

DTDSLDNELAMRLTMLFFGVSAFFSNFLLTCVYVPYVTLVLVPVGFVFYV

SLGYYRKSAREVKRIDSIERSHMMSVFNESISGMPVIIMYKAQHRLMNKL

QATLDDMDSAYFLTAANQRWLSLRLDGLGSLVVLVATILVAVGVFDLTPS

NMGLIISAASFIPEVMSMVAQAVAELENCMNATERILYYKDNIPAEAARE

VDGTELDQRPNWPEQGAISFNNVSMKYRDGLPYVLKSLSVDFQGGHKVGI

CGRTGAGKSTILQTLYRIVELAEGSITIDGVDISTIGLHQLRSQLSIIPQ

EPVLFLGTIRSNLDPLEQYSDAELWGSLRRSGLLDEGETEGKFHLDQKVE

ADGSNFSLGERQLLTLARALLRNTKILVLDEATSNVDYKTDKLVQETISR

EFGHCTILCIAHRLRTIAKYDRILVLESGEINQYDTPWNLYNDKEGIFRG

MCDTSGLNEVDFNK.

A polypeptide, typically having steviol glycoside transport mediating activity, may comprise an amino acid sequence having at least about 50%, at least about 55%, at least about 60%, at least about 65%, at least about 70%, at least about 75%, at least about 80%, at least about 85%, at least about, 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% sequence identity to SEQ ID NO: 29.

A polypeptide, typically having steviol glycoside transport mediating activity, encoded by a recombinant nucleic acid present in a recombinant host of the invention may comprise an amino acid sequence which is a fragment of an amino acid sequence described herein, for example a truncated version of such an amino acid sequence.

That is to say, the invention also a recombinant host overexpressing a biologically active fragment of a polypeptide having steviol glycoside transport mediating activity as described herein.

Biologically active fragments of a polypeptide of the invention include polypeptides comprising amino acid sequences sufficiently identical to or derived from the amino acid sequence of SEQ ID NO: 29 which include fewer amino acids than the full-length polypeptide as given in SEQ ID NO: 29, but which exhibit at least one biological activity of the corresponding full-length polypeptide.

Typically, biologically active fragments comprise a domain or motif with at least one activity of the polypeptide of the invention. A biologically active fragment of a polypeptide of the invention can be a polypeptide which is, for example, about 10, about 25, about 50, about 100 or more amino acids in length or at least about 100 amino acids, at least 150, 200, 250, 300, 350, 400, 600, 1000 amino acids in length, or of a length up to the total number of amino acids of the polypeptide of the invention. Moreover, other biologically active portions, in which other regions of the polypeptide are deleted, can be prepared by recombinant techniques and evaluated for one or more of the biological activities of the native form of a polypeptide of the invention. The invention also features nucleic acid fragments which encode the above biologically active fragments of the polypeptide of the invention.

A recombinant host of the invention may overexpress or be deficient in such a polypeptide.

A recombinant host of the invention may comprise recombinant nucleic acid sequences encoding more than one such polypeptide, for example two, three, four or more such polypeptides. The polypeptides thus encoded may be the same or different.

A recombinant cell of the invention may be modified so as to reduce the expression level of more than one such polypeptide, for example two, three, four or more such polypeptides.

An overexpressed polypeptide encoded by a recombinant nucleic acid present in a recombinant host may be one which is obtainable from or derived from or found in an organism of the genus *Yarrowia*, for example one which is obtainable from or derived from or found in a *Yarrowia lipolytica*.

As used herein, the term "polypeptide" refers to a molecule comprising amino acid residues linked by peptide bonds and containing more than five amino acid residues. The amino acids are identified by either the single-letter or three-letter designations. The term "protein" as used herein is synonymous with the term "polypeptide" and may also refer to two or more polypeptides. Thus, the terms "protein", "peptide" and "polypeptide" can be used interchangeably.

Polypeptides may optionally be modified (e.g., glycosylated, phosphorylated, acylated, farnesylated, prenylated, sulfonated, and the like) to add functionality. Polypeptides exhibiting activity may be referred to as enzymes. It will be understood that, as a result of the degeneracy of the genetic code, a multitude of nucleotide sequences encoding a given polypeptide may be produced.

A polypeptide encoded by a recombinant nucleic acid for use in a recombinant host of the invention may comprise a signal peptide and/or a propeptide sequence. In the event that a polypeptide of the invention comprises a signal peptide and/or a propeptide, sequence identity may be calculated over the mature polypeptide sequence.

A recombinant nucleic acid sequence for use in a recombinant host of the invention may be provided in the form of a nucleic acid construct. The term "nucleic acid construct" refers to a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence, wherein said control sequences are operably linked to said coding sequence.

A recombinant nucleic acid sequence for use in a recombinant host of the invention may be provided in the form of an expression vector, wherein the polynucleotide sequence is operably linked to at least one control sequence for the expression of the polynucleotide sequence in a recombinant host cell.

The term "operably linked" as used herein refers to two or more nucleic acid sequence elements that are physically linked and are in a functional relationship with each other. For instance, a promoter is operably linked to a coding sequence if the promoter is able to initiate or regulate the transcription or expression of a coding sequence, in which case the coding sequence should be understood as being "under the control of" the promoter. Generally, when two nucleic acid sequences are operably linked, they will be in the same orientation and usually also in the same reading frame. They usually will be essentially contiguous, although this may not be required.

An expression vector comprises a polynucleotide coding for a polypeptide as described herein, operably linked to the appropriate control sequences (such as a promoter, and transcriptional and translational stop signals) for expression and/or translation in vitro, or in the host cell of the polynucleotide.

The expression vector may be any vector (e.g., a plasmid or virus), which can be conveniently subjected to recombinant DNA procedures and can bring about the expression of the polynucleotide. The choice of the vector will typically depend on the compatibility of the vector with the cell into which the vector is to be introduced. The vectors may be linear or closed circular plasmids. The vector may be an autonomously replicating vector, i.e., a vector, which exists as an extra-chromosomal entity, the replication of which is independent of chromosomal replication, e.g., a plasmid, an extra-chromosomal element, a mini-chromosome, or an artificial chromosome.

Alternatively, the vector may be one which, when introduced into the host cell, is integrated into the genome and replicated together with the chromosome(s) into which it has been integrated. The integrative cloning vector may integrate at random or at a predetermined target locus in the chromosomes of the host cell. A vector may comprise one or more selectable markers, which permit easy selection of transformed cells.

A recombinant host capable of producing a steviol glycoside which has been modified, preferably in its genome, to result in a deficiency in the production of a polypeptide described herein may be generated according to methods well known to those skilled in the art. A sequence encoding a polypeptide as described herein may be modified such that less or no expression of the polypeptide takes place. A sequence encoding a polypeptide as described herein may be partially or entirely deleted, for example.

A recombinant host of the invention may comprise any polypeptide as described herein. A recombinant host of the invention may overexpress or be deficient in any polypeptide described herein. Typically, a recombinant host of the invention is capable of producing a steviol glycoside. For example, a recombinant host of the invention may be capable of producing one or more of, for example, steviol-13-monoside, steviol-19-monoside, 13-[(β-D-Glucopyranosyl)oxy)kaur-16-en-18-oic acid 2-O-β-D-glucopyranosyl-β-D-glucopyranosyl ester, rubusoside, stevioside, steviol-19-diside, steviolbioside, rebA, rebE, rebD or rebM.

A recombinant host of the invention may comprise one or more recombinant nucleic acid sequences encoding one or more polypeptides having UDP-glycosyltransferase (UGT) activity.

For the purposes of this invention, a polypeptide having UGT activity is one which has glycosyltransferase activity (EC 2.4), i.e. that can act as a catalyst for the transfer of a monosaccharide unit from an activated nucleotide sugar (also known as the "glycosyl donor") to a glycosyl acceptor molecule, usually an alcohol. The glycosyl donor for a UGT is typically the nucleotide sugar uridine diphosphate glucose (uracil-diphosphate glucose, UDP-glucose).

Figure 21:
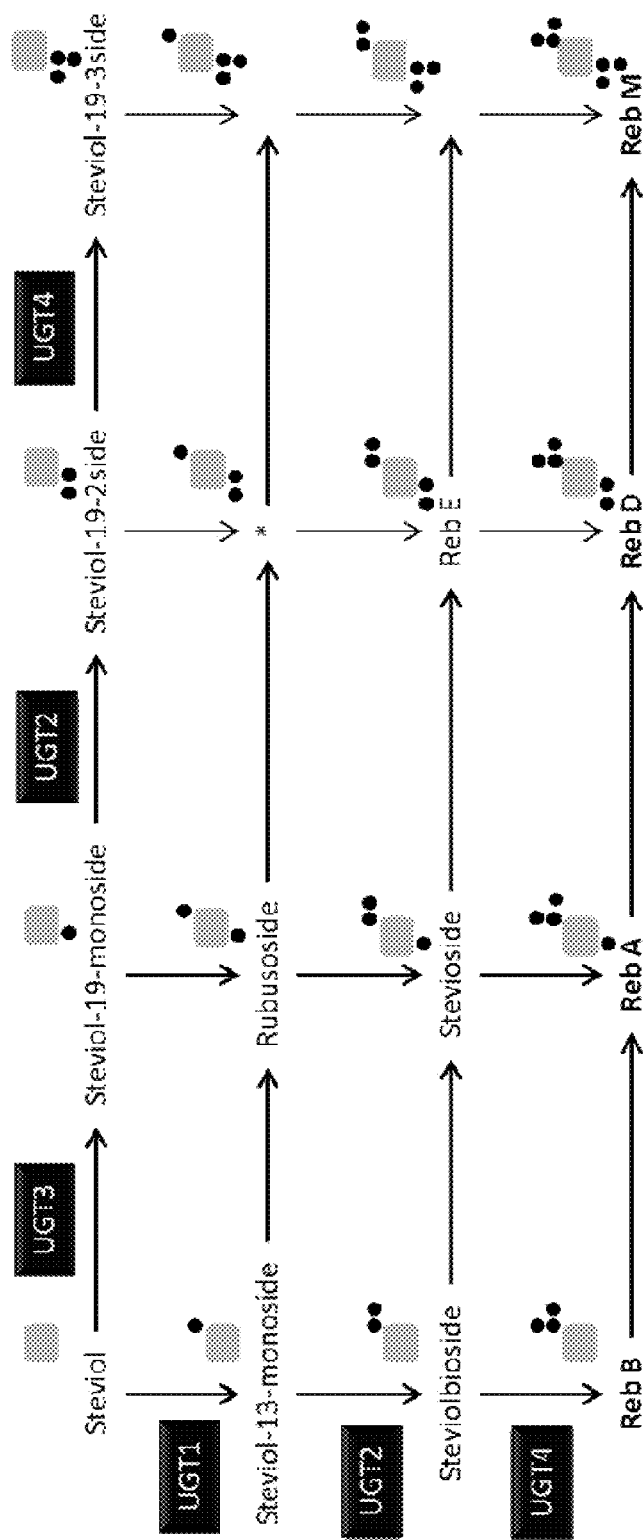
FIG. 21 sets out a schematic diagram of the potential pathways leading to biosynthesis of steviol glycosides. The compound shown with an asterisk is 13-[(β-D-Glucopyranosyl)oxy)kaur-16-en-18-oic acid 2-O-β-D-glucopyranosyl-β-D-glucopyranosyl ester.

Such additional UGTs may be selected so as to produce a desired steviol glycoside. Schematic diagrams of steviol glycoside formation are set out in Humphrey et al., Plant Molecular Biology (2006) 61: 47-62 and Mohamed et al., J. Plant Physiology 168 (2011) 1136-1141. In addition, FIG. 21 sets out a schematic diagram of steviol glycoside formation.

A recombinant host of the invention may thus comprise one or more recombinant nucleic acid sequences encoding one or more of:

(i) a polypeptide having UGT74G1 activity;
(ii) a polypeptide having UGT2 activity;
(iii) a polypeptide having UGT85C2 activity; and
(iv) a polypeptide having UGT76G1 activity.

A recombinant yeast suitable for use in the invention may comprise a nucleotide sequence encoding a polypeptide capable of catalyzing the addition of a C-13-glucose to steviol. That is to say, a recombinant yeast suitable for use in a method of the invention may comprise a UGT which is capable of catalyzing a reaction in which steviol is converted to steviolmonoside.

Such a recombinant yeast suitable for use in a method of the invention may comprise a nucleotide sequence encoding a polypeptide having the activity shown by UDP-glycosyltransferase (UGT) UGT85C2, whereby the nucleotide sequence upon transformation of the yeast confers on that yeast the ability to convert steviol to steviolmonoside.

UGT85C2 activity is transfer of a glucose unit to the 13-OH of steviol. Thus, a suitable UGT85C2 may function as a uridine 5'-diphospho glucosyl: steviol 13-OH transferase, and a uridine 5'-diphospho glucosyl: steviol-19-0-glucoside 13-OH transferase. A functional UGT85C2 polypeptides may also catalyze glucosyl transferase reactions that utilize steviol glycoside substrates other than steviol and steviol-19-O-glucoside. Such sequences may be referred to as UGT1 sequences herein.

A recombinant yeast suitable for use in the invention may comprise a nucleotide sequence encoding a polypeptide which has UGT2 activity.

A polypeptide having UGT2 activity is one which functions as a uridine 5'-diphospho glucosyl: steviol-13-O-glucoside transferase (also referred to as a steviol-13-monoglucoside 1,2-glucosylase), transferring a glucose moiety to the C-2' of the 13-0-glucose of the acceptor molecule, steviol-13-O-glucoside. Typically, a suitable UGT2 polypeptide also functions as a uridine 5'-diphospho glucosyl: rubusoside transferase transferring a glucose moiety to the C-2' of the 13-O-glucose of the acceptor molecule, rubusoside.

A polypeptide having UGT2 activity may also catalyze reactions that utilize steviol glycoside substrates other than steviol-13-O-glucoside and rubusoside, e.g., functional UGT2 polypeptides may utilize stevioside as a substrate, transferring a glucose moiety to the C-2' of the 19-O-glucose residue to produce rebaudioside E. A functional UGT2 polypeptides may also utilize rebaudioside A as a substrate, transferring a glucose moiety to the C-2' of the 19-O-glucose residue to produce rebaudioside D. However, a functional UGT2 polypeptide may be one which does not transfer a glucose moiety to steviol compounds having a 1,3-bound glucose at the C-13 position, i.e., transfer of a glucose moiety to steviol 1,3-bioside and 1,3-stevioside typically does not occur.

A polypeptide having UGT2 activity may also transfer sugar moieties from donors other than uridine diphosphate glucose. For example, a polypeptide having UGT2 activity act as a uridine 5'-diphospho D-xylosyl: steviol-13-O-glucoside transferase, transferring a xylose moiety to the C-2' of the 13-O-glucose of the acceptor molecule, steviol-13-O-glucoside. As another example, a polypeptide having UGT2 activity may act as a uridine 5'-diphospho L-rhamnosyl:

steviol-13-0-glucoside transferase, transferring a rhamnose moiety to the C-2' of the 13-O-glucose of the acceptor molecule, steviol.

A recombinant yeast suitable for use in the method of the invention may comprise a nucleotide sequence encoding a polypeptide having UGT activity may comprise a nucleotide sequence encoding a polypeptide capable of catalyzing the addition of a C-19-glucose to steviolbioside. That is to say, a recombinant yeast of the invention may comprise a UGT which is capable of catalyzing a reaction in which steviolbioside is converted to stevioside. Accordingly, such a recombinant yeast may be capable of converting steviolbioside to stevioside. Expression of such a nucleotide sequence may confer on the recombinant yeast the ability to produce at least stevioside.

A recombinant yeast suitable for use in a method of the invention may thus also comprise a nucleotide sequence encoding a polypeptide having the activity shown by UDP-glycosyltransferase (UGT) UGT74G1, whereby the nucleotide sequence upon transformation of the yeast confers on the cell the ability to convert steviolbioside to stevioside.

Suitable UGT74G1 polypeptides may be capable of transferring a glucose unit to the 13-OH and/or the 19-000H of steviol. A suitable UGT74G1 polypeptide may function as a uridine 5'-diphospho glucosyl: steviol 19-000H transferase and/or a uridine 5'-diphospho glucosyl: steviol-13-0-glucoside 19-000H transferase. Functional UGT74G1 polypeptides also may catalyze glycosyl transferase reactions that utilize steviol glycoside substrates other than steviol and steviol-13-O-glucoside, or that transfer sugar moieties from donors other than uridine diphosphate glucose. Such sequences may be referred to herein as UGT3 sequences.

A recombinant yeast suitable for use in a method the invention may comprise a nucleotide sequence encoding a polypeptide capable of catalyzing glucosylation of the C-3' of the glucose at the C-13 position of stevioside. That is to say, a recombinant yeast suitable for use in a method of the invention may comprise a UGT which is capable of catalyzing a reaction in which stevioside is converted to rebaudioside A. Accordingly, such a recombinant yeast may be capable of converting stevioside to rebaudioside A. Expression of such a nucleotide sequence may confer on the yeast the ability to produce at least rebaudioside A.

A recombinant yeast suitable for use in a method of the invention may thus also comprise a nucleotide sequence encoding a polypeptide having the activity shown by UDP-glycosyltransferase (UGT) UGT76G1, whereby the nucleotide sequence upon transformation of a yeast confers on that yeast the ability to convert stevioside to rebaudioside A.

A suitable UGT76G1 adds a glucose moiety to the C-3' of the C-13-O-glucose of the acceptor molecule, a steviol 1,2 glycoside. Thus, UGT76G1 functions, for example, as a uridine 5'-diphospho glucosyl: steviol 13-0-1,2 glucoside C-3 ' glucosyl transferase and a uridine 5'-diphospho glucosyl: steviol-19-O-glucose, 13-0-1,2 bioside C-3' glucosyl transferase. Functional UGT76G1 polypeptides may also catalyze glucosyl transferase reactions that utilize steviol glycoside substrates that contain sugars other than glucose, e.g., steviol rhamnosides and steviol xylosides. Such sequences may be referred to herein as UGT4 sequences. A UGT4 may alternatively or in addition be capable of converting RebD to RebM.

A recombinant yeast suitable for use in a method of the invention typically comprises nucleotide sequences encoding at least one polypeptide having UGT1 activity, at least one polypeptide having UGT2 activity, least one polypeptide having UGT3 activity and at least one polypeptide having UGT4 activity. One or more of these nucleic acid sequences may be recombinant. A given nucleic acid may encode a polypeptide having one or more of the above activities. For example, a nucleic acid encode for a polypeptide which has two, three or four of the activities set out above. Preferably, a recombinant yeast for use in the method of the invention comprises UGT1, UGT2 and UGT3 and UGT4 activity. Suitable UGT1, UGT2, UGT3 and UGT4 sequences are described in Table 1 of WO2015/007748.

A recombinant host of the invention may comprise two or more nucleic acid sequences encoding a polypeptide having any one UGT activity, for example UGT1, 2, 3 or 4, activity. Where a recombinant host of the invention comprises two or more nucleic acid sequence encoding a polypeptide having any one UGT activity, those nucleic acid sequences may be the same or different and/or may encode the same or different polypeptides. In particular, a recombinant host of the invention may comprise a nucleic acid sequence encoding a two different UGT2 polypeptides.

A recombinant host according to the invention may comprise one or more recombinant nucleotide sequence(s) encoding one of more of:
 a polypeptide having ent-copalyl pyrophosphate synthase activity;
 a polypeptide having ent-Kaurene synthase activity;
 a polypeptide having ent-Kaurene oxidase activity; and
 a polypeptide having kaurenoic acid 13-hydroxylase activity.

For the purposes of this invention, a polypeptide having ent-copalyl pyrophosphate synthase (EC 5.5.1.13) is capable of catalyzing the chemical reaction:

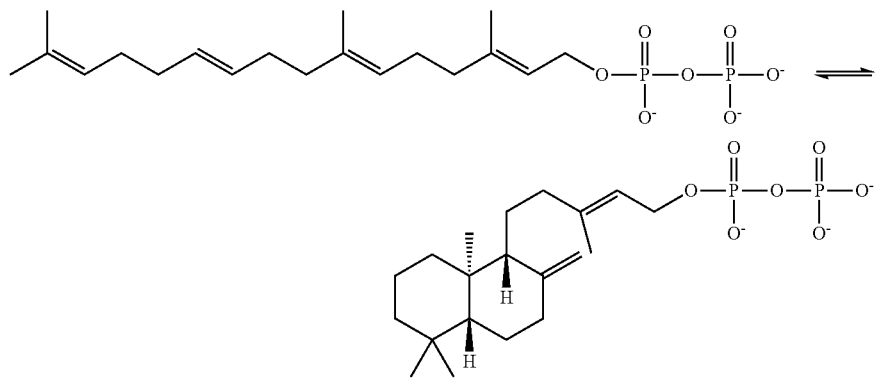

This enzyme has one substrate, geranylgeranyl pyrophosphate, and one product, ent-copalyl pyrophosphate. This enzyme participates in gibberellin biosynthesis. This enzyme belongs to the family of isomerase, specifically the class of intramolecular lyases. The systematic name of this enzyme class is ent-copalyl-diphosphate lyase (decyclizing). Other names in common use include having ent-copalyl pyrophosphate synthase, ent-kaurene synthase A, and ent-kaurene synthetase A.

Suitable nucleic acid sequences encoding an ent-copalyl pyrophosphate synthase may for instance comprise a sequence as set out in SEQ ID. NO: 1, 3, 5, 7, 17, 19, 59, 61, 141, 142, 151, 152, 153, 154, 159, 160, 182 or 184 of WO2015/007748.

For the purposes of this invention, a polypeptide having ent-kaurene synthase activity (EC 4.2.3.19) is a polypeptide that is capable of catalyzing the chemical reaction:

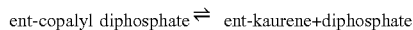

Hence, this enzyme has one substrate, ent-copalyl diphosphate, and two products, ent-kaurene and diphosphate.

This enzyme belongs to the family of lyases, specifically those carbon-oxygen lyases acting on phosphates. The systematic name of this enzyme class is ent-copalyl-diphosphate diphosphate-lyase (cyclizing, ent-kaurene-forming). Other names in common use include ent-kaurene synthase B, ent-kaurene synthetase B, ent-copalyl-diphosphate diphosphate-lyase, and (cyclizing). This enzyme participates in diterpenoid biosynthesis.

Suitable nucleic acid sequences encoding an ent-Kaurene synthase may for instance comprise a sequence as set out in SEQ ID. NO: 9, 11, 13, 15, 17, 19, 63, 65, 143, 144, 155, 156, 157, 158, 159, 160, 183 or 184 of WO2015/007748.

ent-copalyl diphosphate synthases may also have a distinct ent-kaurene synthase activity associated with the same protein molecule. The reaction catalyzed by ent-kaurene synthase is the next step in the biosynthetic pathway to gibberellins. The two types of enzymic activity are distinct, and site-directed mutagenesis to suppress the ent-kaurene synthase activity of the protein leads to build up of ent-copalyl pyrophosphate.

Accordingly, a single nucleotide sequence used in a recombinant host of the invention may encode a polypeptide having ent-copalyl pyrophosphate synthase activity and ent-kaurene synthase activity. Alternatively, the two activities may be encoded two distinct, separate nucleotide sequences.

For the purposes of this invention, a polypeptide having ent-kaurene oxidase activity (EC 1.14.13.78) is a polypeptide which is capable of catalysing three successive oxidations of the 4-methyl group of ent-kaurene to give kaurenoic acid. Such activity typically requires the presence of a cytochrome P450.

Suitable nucleic acid sequences encoding an ent-Kaurene oxidase may for instance comprise a sequence as set out in SEQ ID. NO: 21, 23, 25, 67, 85, 145, 161, 162, 163, 180 or 186 of WO2015/007748.

For the purposes of the invention, a polypeptide having kaurenoic acid 13-hydroxylase activity (EC 1.14.13) is one which is capable of catalyzing the formation of steviol (ent-kaur-16-en-13-ol-19-oic acid) using NADPH and $O_2$. Such activity may also be referred to as ent-ka 13-hydroxylase activity.

Suitable nucleic acid sequences encoding a kaurenoic acid 13-hydroxylase may for instance comprise a sequence as set out in SEQ ID. NO: 27, 29, 31, 33, 69, 89, 91, 93, 95, 97, 146, 164, 165, 166, 167 or 185 of WO2015/007748.

A recombinant host of the invention may comprise a recombinant nucleic acid sequence encoding a polypeptide having NADPH-cytochrome p450 reductase activity. That is to say, a recombinant host of the invention may be capable of expressing a nucleotide sequence encoding a polypeptide having NADPH-cytochrome p450 reductase activity. For the purposes of the invention, a polypeptide having NADPH-Cytochrome P450 reductase activity (EC 1.6.2.4; also known as NADPH:ferrihemoprotein oxidoreductase, NADPH:hemoprotein oxidoreductase, NADPH:P450 oxidoreductase, P450 reductase, POR, CPR, CYPOR) is typically one which is a membrane-bound enzyme allowing electron transfer to cytochrome P450 in the microsome of the eukaryotic cell from a FAD- and FMN-containing enzyme NADPH:cytochrome P450 reductase (POR; EC 1.6.2.4).

In a recombinant host of the invention, the ability of the host to produce geranylgeranyl diphosphate (GGPP) may be upregulated. Upregulated in the context of this invention implies that the recombinant host produces more GGPP than an equivalent non-recombinant host.

Accordingly, a recombinant host of the invention may comprise one or more nucleotide sequence(s) encoding hydroxymethylglutaryl-CoA reductase, farnesyl-pyrophosphate synthetase and geranylgeranyl diphosphate synthase, whereby the nucleotide sequence(s) upon transformation of a host confer(s) on that host the ability to produce elevated levels of GGPP. Thus, a recombinant host according to the invention may comprise one or more recombinant nucleic acid sequence(s) encoding one or more of hydroxymethyl-glutaryl-CoA reductase, farnesyl-pyrophosphate synthetase and geranylgeranyl diphosphate synthase.

Accordingly, a recombinant host of the invention may comprise nucleic acid sequences encoding one or more of:
a polypeptide having hydroxymethylglutaryl-CoA reductase activity;
a polypeptide having farnesyl-pyrophosphate synthetase activity; and A recombinant host of the invention may be, for example, an multicellular organism or a cell thereof or a unicellular organism. A host of the invention may be a prokaryotic, archaebacterial or eukaryotic host cell.

A prokaryotic host cell may, but is not limited to, a bacterial host cell. An eukaryotic host cell may be, but is not limited to, a yeast, a fungus, an amoeba, an algae, an animal, an insect host cell.

An eukaryotic host cell may be a fungal host cell. "Fungi" include all species of the subdivision Eumycotina (Alexopoulos, C. J., 1962, In: Introductory Mycology, John Wiley & Sons, Inc., New York). The term fungus thus includes among others filamentous fungi and yeast.

"Filamentous fungi" are herein defined as eukaryotic microorganisms that include all filamentous forms of the subdivision *Eumycotina* and *Oomycota* (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligatory aerobic. Filamentous fungal strains include, but are not limited to, strains of *Acremonium, Aspergillus, Agaricus, Aureobasidium, Cryptococcus, Corynascus, Chrysosporium, Filibasidium, Fusarium, Humicola, Magnaporthe, Monascus, Mucor, Myceliophthora, Mortierella, Neocallimastix, Neurospora, Paecilomyces, Penicillium, Piromyces, Phanerochaete Podospora, Pycnoporus, Rhizopus, Schizophyllum, Sordaria, Talaromyces, Rasmsonia, Thermoascus, Thielavia, Tolypocladium, Trametes* and

*Trichoderma*. Preferred filamentous fungal strains that may serve as host cells belong to the species *Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora thermophyla*. Reference host cells for the comparison of fermentation characteristics of transformed and untransformed cells, include e.g. *Aspergillus niger* CBS120.49, CBS 513.88, *Aspergillus oryzae* ATCC16868, ATCC 20423, IFO 4177, ATCC 1011, ATCC 9576, ATCC14488-14491, ATCC 11601, ATCC12892, *Aspergillus fumigatus* AF293 (CBS101355), *P. chrysogenum* CBS 455.95, *Penicillium citrinum* ATCC 38065, *Penicillium chrysogenum* P2, *Acremonium chrysogenum* ATCC 36225, ATCC 48272, *Trichoderma reesei* ATCC 26921, ATCC 56765, ATCC 26921, *Aspergillus sojae* ATCC11906, *Chrysosporium lucknowense* ATCC44006 and derivatives of all of these strains. Particularly preferred as filamentous fungal host cell are *Aspergillus niger* CBS 513.88 and derivatives thereof.

An eukaryotic host cell may be a yeast cell. Preferred yeast host cells may be selected from the genera: *Saccharomyces* (e.g., *S. cerevisiae, S. bayanus, S. pastorianus, S. carlsbergensis*), Brettanomyces, *Kluyveromyces*, *Candida* (e.g., *C. krusei, C. revkaufi, C. pulcherrima, C. tropicalis, C. utilis*), *Issatchenkia* (eg. *I. orientalis*) *Pichia* (e.g., *P. pastoris* and P. kudriavzevii), *Schizosaccharomyces, Hansenula, Kloeckera, Pachysolen, Schwanniomyces, Trichosporon, Yarrowia* (e.g., *Y. lipolytica* (formerly classified as *Candida lipolytica*)), *Yamadazyma*.

Prokaryotic host cells may be bacterial host cells. Bacterial host cell may be Gram negative or Gram positive bacteria. Examples of bacteria include, but are not limited to, bacteria belonging to the genus *Bacillus* (e.g., *B. subtilis, B. amyloliquefaciens, B. licheniformis, B. puntis, B. megaterium, B. halodurans, B. pumilus,*), *Acinetobacter, Nocardia, Xanthobacter, Escherichia* (e.g., *E. coli* (e.g., strains DH 1 OB, Stbl2, DH5-alpha, DB3, DB3.1), DB4, DB5, JDP682 and ccdA-over (e.g., U.S. application Ser. No. 09/518, 188))), *Streptomyces, Erwinia, Klebsiella, Serratia* (e.g., S. marcessans), *Pseudomonas* (e.g., *P. aeruginosa*), *Salmonella* (e.g., *S. typhimurium, S. typhi*). Bacteria also include, but are not limited to, photosynthetic bacteria (e.g., green non-sulfur bacteria (e.g., *Choroflexus* bacteria (e.g., *C. aurantiacus*), *Chloronema* (e.g., *C. gigateum*)), green sulfur bacteria (e.g., *Chlorobium* bacteria (e.g., *C. limicola*), *Pelodictyon* (e.g., *P. luteolum*), purple sulfur bacteria (e.g., *Chromatium* (e.g., *C. okenii*)), and purple non-sulfur bacteria (e.g., *Rhodospirillum* (e.g., *R. rubrum*), *Rhodobacter* (e.g. *R. sphaeroides, R. capsulatus*), and Rhodomicrobium bacteria (e.g., *R. vanellii*)).

Host Cells may be host cells from non-microbial organisms. Examples of such cells, include, but are not limited to, insect cells (e.g., *Drosophila* (e.g., *D. melanogaster*), *Spodoptera* (e.g., *S. frugiperda* Sf9 or Sf21 cells) and *Trichoplusa* (e.g., High-Five cells); nematode cells (e.g., *C. elegans* cells); avian cells; amphibian cells (e.g., *Xenopus laevis* cells); reptilian cells; and mammalian cells (e.g., NIH3T3, 293, CHO, COS, VERO, C127, BHK, Per-C6, Bowes melanoma and HeLa cells).

A recombinant host according to the present invention may be able to grow on any suitable carbon source known in the art and convert it to a steviol glycoside. The recombinant host may be able to convert directly plant biomass, celluloses, hemicelluloses, pectines, rhamnose, galactose, fucose, maltose, maltodextrines, ribose, ribulose, or starch, starch derivatives, sucrose, lactose and glycerol. Hence, a preferred host expresses enzymes such as cellulases (endocellulases and exocellulases) and hemicellulases (e.g. endo- and exo-xylanases, arabinases) necessary for the conversion of cellulose into glucose monomers and hemicellulose into xylose and arabinose monomers, pectinases able to convert pectines into glucuronic acid and galacturonic acid or amylases to convert starch into glucose monomers. Preferably, the host is able to convert a carbon source selected from the group consisting of glucose, xylose, arabinose, sucrose, lactose and glycerol. The host cell may for instance be a eukaryotic host cell as described in WO03/062430, WO06/009434, EP1499708B1, WO2006096130 or WO04/099381.

Thus, in a further aspect, the invention also provides a process for the preparation of a steviol glycoside which comprises fermenting a recombinant host of the invention which is capable of producing at least one steviol glycoside in a suitable fermentation medium, and optionally recovering the steviol glycoside.

The fermentation medium used in the process for the production of a steviol glycoside may be any suitable fermentation medium which allows growth of a particular eukaryotic host cell. The essential elements of the fermentation medium are known to the person skilled in the art and may be adapted to the host cell selected.

Preferably, the fermentation medium comprises a carbon source selected from the group consisting of plant biomass, celluloses, hemicelluloses, pectines, rhamnose, galactose, fucose, fructose, maltose, maltodextrines, ribose, ribulose, or starch, starch derivatives, sucrose, lactose, fatty acids, triglycerides and glycerol. Preferably, the fermentation medium also comprises a nitrogen source such as ureum, or an ammonium salt such as ammonium sulphate, ammonium chloride, ammoniumnitrate or ammonium phosphate.

The fermentation process according to the present invention may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. A SSF process may be particularly attractive if starch, cellulose, hemicelluose or pectin is used as a carbon source in the fermentation process, where it may be necessary to add hydrolytic enzymes, such as cellulases, hemicellulases or pectinases to hydrolyse the substrate.

The recombinant host used in the process for the preparation of a steviol glycoside may be any suitable recombinant host as defined herein above. It may be advantageous to use a recombinant eukaryotic recombinant host according to the invention in the process since most eukaryotic cells do not require sterile conditions for propagation and are insensitive to bacteriophage infections. In addition, eukaryotic host cells may be grown at low pH to prevent bacterial contamination.

The recombinant host according to the present invention may be a facultative anaerobic microorganism. A facultative anaerobic recombinant host can be propagated aerobically to a high cell concentration. This anaerobic phase can then be carried out at high cell density which reduces the fermentation volume required substantially, and may minimize the risk of contamination with aerobic microorganisms.

The fermentation process for the production of a steviol glycoside according to the present invention may be an aerobic or an anaerobic fermentation process.

An anaerobic fermentation process may be herein defined as a fermentation process run in the absence of oxygen or in which substantially no oxygen is consumed, preferably less than 5, 2.5 or 1 mmol/L/h, and wherein organic molecules serve as both electron donor and electron acceptors. The fermentation process according to the present invention may also first be run under aerobic conditions and subsequently under anaerobic conditions.

The fermentation process may also be run under oxygen-limited, or micro-aerobical, conditions. Alternatively, the fermentation process may first be run under aerobic conditions and subsequently under oxygen-limited conditions. An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used.

The production of a steviol glycoside in the process according to the present invention may occur during the growth phase of the host cell, during the stationary (steady state) phase or during both phases. It may be possible to run the fermentation process at different temperatures.

The process for the production of a steviol glycoside may be run at a temperature which is optimal for the recombinant host. The optimum growth temperature may differ for each transformed recombinant host and is known to the person skilled in the art. The optimum temperature might be higher than optimal for wild type organisms to grow the organism efficiently under non-sterile conditions under minimal infection sensitivity and lowest cooling cost. Alternatively, the process may be carried out at a temperature which is not optimal for growth of the recombinant host.

The process for the production of a steviol glycoside according to the present invention may be carried out at any suitable pH value. If the recombinant host is a yeast, the pH in the fermentation medium preferably has a value of below 6, preferably below 5,5, preferably below 5, preferably below 4,5, preferably below 4, preferably below pH 3,5 or below pH 3,0, or below pH 2,5, preferably above pH 2. An advantage of carrying out the fermentation at these low pH values is that growth of contaminant bacteria in the fermentation medium may be prevented.

Such a process may be carried out on an industrial scale. The product of such a process is one or more steviol glycosides.

Recovery of steivol glycoside(s) from the fermentation medium may be performed by known methods in the art, for instance by distillation, vacuum extraction, solvent extraction, or evaporation.

In the process for the production of a steviol glycoside according to the invention, it may be possible to achieve a concentration of above 5 mg/l fermentation broth, preferably above 10 mg/l, preferably above 20 mg/l, preferably above 30 mg/l fermentation broth, preferably above 40 mg/l, more preferably above 50 mg/l, preferably above 60 mg/l, preferably above 70, preferably above 80 mg/l, preferably above 100 mg/l, preferably above 1 g/l, preferably above 5 g/l, preferably above 10 g/l, for example at least about 15 g/L, such as at least about 20 g/l.

The invention further provides a fermentation broth comprising a steviol glycoside obtainable by the process of the invention for the preparation of a steivol glycoside.

In the event that one or more steviol glycosides is expressed within a recombinant host of the invention, such cells may need to be treated so as to release them. Preferentially, at least one steviol glycoside, for example rebA or rebM, is produced extracellularly The invention also provides a steviol glycoside obtained by a process according to the invention for the preparation of a steviol glycoside or obtainable from a fermentation broth of the invention. Such a steviol glycoside may be a non-naturally occurring steviol glycoside, that is to say one which is not produced in plants.

Also provided is a composition obtainable by a process of the invention (which typically comprises one or more steviol glycosides), Also provided is a composition comprising two or more steviol glycosides obtainable by a process of the invention for the preparation of a steviol glycoside or obtainable from a fermentation broth of the invention. In such a composition, one or more of the steviol glycosides may be a non-naturally occurring steviol glycoside, that is to say one which is not produced in plants. These are all compositions of the invention.

A composition of the invention may be used in any application known for such compounds. In particular, such a composition may for instance be used as a sweetener, for example in a food or a beverage. According to the invention therefore, there is provided a foodstuff, feed or beverage which comprises a composition of the invention.

For example a composition of the invention may be formulated in soft drinks, as a tabletop sweetener, chewing gum, dairy product such as yoghurt (eg. plain yoghurt), cake, cereal or cereal-based food, nutraceutical, pharmaceutical, edible gel, confectionery product, cosmetic, toothpastes or other oral cavity composition, etc. In addition, a composition of the invention can be used as a sweetener not only for drinks, foodstuffs, and other products dedicated for human consumption, but also in animal feed and fodder with improved characteristics.

Accordingly, the invention provides, inter alia, a foodstuff, feed or beverage which comprises a composition of the invention.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

A composition of the invention can be used in dry or liquid forms. It can be added before or after heat treatment of food products. The amount of the sweetener depends on the purpose of usage. It can be added alone or in the combination with other compounds.

A composition of the invention may be blended with one or more further non-caloric or caloric sweeteners. Such blending may be used to improve flavour or temporal profile or stability. A wide range of both non-caloric and caloric sweeteners may be suitable for blending with a composition of the invention. For example, non-caloric sweeteners such as mogroside, monatin, aspartame, acesulfame salts, cyclamate, sucralose, saccharin salts or erythritol. Caloric sweeteners suitable for blending with a steviol glycoside or a composition of the invention include sugar alcohols and carbohydrates such as sucrose, glucose, fructose and HFCS. Sweet tasting amino acids such as glycine, alanine or serine may also be used.

A composition of the invention can be used in the combination with a sweetener suppressor, such as a natural sweetener suppressor. It may be combined with an umami taste enhancer, such as an amino acid or a salt thereof.

A composition of the invention can be combined with a polyol or sugar alcohol, a carbohydrate, a physiologically active substance or functional ingredient (for example a carotenoid, dietary fiber, fatty acid, saponin, antioxidant, nutraceutical, flavonoid, isothiocyanate, phenol, plant sterol or stanol (phytosterols and phytostanols), a polyols, a prebiotic, a probiotic, a phytoestrogen, soy protein, sulfides/ thiols, amino acids, a protein, a vitamin, a mineral, and/or a substance classified based on a health benefits, such as cardiovascular, cholesterol-reducing or anti-inflammatory.

A composition of the invention may include a flavoring agent, an aroma component, a nucleotide, an organic acid, an organic acid salt, an inorganic acid, a bitter compound, a protein or protein hydrolyzate, a surfactant, a flavonoid, an astringent compound, a vitamin, a dietary fiber, an antioxidant, a fatty acid and/or a salt.

A composition of the invention may be applied as a high intensity sweetener to produce zero calorie, reduced calorie or diabetic beverages and food products with improved taste characteristics. Also it can be used in drinks, foodstuffs, pharmaceuticals, and other products in which sugar cannot be used.

In addition, a composition of the invention may be used as a sweetener not only for drinks, foodstuffs, and other products dedicated for human consumption, but also in animal feed and fodder with improved characteristics.

The examples of products where a composition of the invention can be used as a sweetening compound can be as alcoholic beverages such as vodka, wine, beer, liquor, sake, etc; natural juices, refreshing drinks, carbonated soft drinks, diet drinks, zero calorie drinks, reduced calorie drinks and foods, yogurt drinks, instant juices, instant coffee, powdered types of instant beverages, canned products, syrups, fermented soybean paste, soy sauce, vinegar, dressings, mayonnaise, ketchups, curry, soup, instant bouillon, powdered soy sauce, powdered vinegar, types of biscuits, rice biscuit, crackers, bread, chocolates, caramel, candy, chewing gum, jelly, pudding, preserved fruits and vegetables, fresh cream, jam, marmalade, flower paste, powdered milk, ice cream, sorbet, vegetables and fruits packed in bottles, canned and boiled beans, meat and foods boiled in sweetened sauce, agricultural vegetable food products, seafood, ham, sausage, fish ham, fish sausage, fish paste, deep fried fish products, dried seafood products, frozen food products, preserved seaweed, preserved meat, tobacco, medicinal products, and many others. In principal it can have unlimited applications.

The sweetened composition comprises a beverage, non-limiting examples of which include non-carbonated and carbonated beverages such as colas, ginger ales, root beers, ciders, fruit-flavored soft drinks (e.g., citrus-flavored soft drinks such as lemon-lime or orange), powdered soft drinks, and the like; fruit juices originating in fruits or vegetables, fruit juices including squeezed juices or the like, fruit juices containing fruit particles, fruit beverages, fruit juice beverages, beverages containing fruit juices, beverages with fruit flavorings, vegetable juices, juices containing vegetables, and mixed juices containing fruits and vegetables; sport drinks, energy drinks, near water and the like drinks (e.g., water with natural or synthetic flavorants); tea type or favorite type beverages such as coffee, cocoa, black tea, green tea, oolong tea and the like; beverages containing milk components such as milk beverages, coffee containing milk components, cafe au lait, milk tea, fruit milk beverages, drinkable yogurt, lactic acid bacteria beverages or the like; and dairy products.

Generally, the amount of sweetener present in a sweetened composition varies widely depending on the particular type of sweetened composition and its desired sweetness. Those of ordinary skill in the art can readily discern the appropriate amount of sweetener to put in the sweetened composition.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

Thus, compositions which incorporate a composition of the invention can be made by any method known to those skilled in the art that provide homogenous even or homogeneous mixtures of the ingredients. These methods include dry blending, spray drying, agglomeration, wet granulation, compaction, co-crystallization and the like.

In solid form a composition of the invention can be provided to consumers in any form suitable for delivery into the comestible to be sweetened, including sachets, packets, bulk bags or boxes, cubes, tablets, mists, or dissolvable strips. The composition can be delivered as a unit dose or in bulk form.

For liquid sweetener systems and compositions convenient ranges of fluid, semi-fluid, paste and cream forms, appropriate packing using appropriate packing material in any shape or form shall be invented which is convenient to carry or dispense or store or transport any combination containing any of the above sweetener products or combination of product produced above.

A composition of the invention may include various bulking agents, functional ingredients, colorants, flavors.

The terms "sequence homology" or "sequence identity" or "homology" or "identity" are used interchangeably herein. For the purpose of this invention, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss.bioinformatics.nl). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at www.ncbi.nlm.nih.gov.

Standard genetic techniques, such as overexpression of enzymes in the host cells, genetic modification of host cells, or hybridisation techniques, are known methods in the art, such as described in Sambrook and Russel (2001) "Molecular Cloning: A Laboratory Manual (3rd edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation, genetic modification etc of fungal host cells are known from e.g. EP-A-0 635 574, WO 98/46772, WO 99/60102 and WO 00/37671, WO90/14423, EP-A-0481008, EP-A-0635 574 and U.S. Pat. No. 6,265,186.

Embodiments of the Invention

1. A recombinant host capable of producing a steviol glycoside which overexpresses a polypeptide which mediates steviol glycoside transport and which polypeptide comprises the amino acid sequence set forth in SEQ ID NO: 29 or an amino acid sequence having at least about 50% sequence identity thereto.

2. A recombinant host capable of producing a steviol glycoside which has been modified, preferably in its genome, to result in a deficiency in the production of a polypeptide which mediates steviol glycoside transport and which polypeptide comprises the amino acid sequence set forth in SEQ ID NO: 29 or an amino acid sequence having at least about 50% sequence identity thereto.

3. A recombinant host according to claim 1, which comprises a recombinant nucleic acid encoding a polypeptide which comprises the amino acid sequence set forth in SEQ ID NO: 29 or an amino acid sequence having at least about 50% sequence identity thereto.

4. A recombinant host according to any one of the preceding embodiments which comprises one or more recombinant nucleotide sequence(s) encoding:
a polypeptide having ent-copalyl pyrophosphate synthase activity;
a polypeptide having ent-Kaurene synthase activity;
a polypeptide having ent-Kaurene oxidase activity; and
a polypeptide having kaurenoic acid 13-hydroxylase activity.

5. A recombinant host according to any one of the preceding embodiments, which comprises a recombinant nucleic acid sequence encoding a polypeptide having NADPH-cytochrome p450 reductase activity.

6. A recombinant host according to any one of the preceding embodiments which comprises a recombinant nucleic acid sequence encoding one or more of:
(i) a polypeptide having UGT74G1 activity;
(ii) a polypeptide having UGT2 activity;
(iii) a polypeptide having UGT85C2 activity; and
(iv) a polypeptide having UGT76G1 activity.

7. A recombinant host according to any one of the preceding embodiments, wherein the host belongs to one of the genera *Saccharomyces, Aspergillus, Pichia, Kluyveromyces, Candida, Hansenula, Humicola, Issatchenkia, Trichosporon, Brettanomyces, Pachysolen, Yarrowia, Yamadazyma* or *Escherichia*.

8. A recombinant host according to embodiment 7, wherein the recombinant host is a *Saccharomyces cerevisiae* cell, a *Yarrowia lipolytica* cell, a *Candida krusei* cell, an *Issatchenkia orientalis* cell or an *Escherichia coli* cell.

9. A recombinant host according to any one of the preceding embodiments, wherein the ability of the host to produce geranylgeranyl diphosphate (GGPP) is upregulated.

10. A recombinant host according to any one of the preceding embodiments which comprises a nucleic acid sequence encoding one or more of:
a polypeptide having hydroxymethylglutaryl-CoA reductase activity; or a polypeptide having farnesyl-pyrophosphate synthetase activity.

11. A recombinant host capable of producing a steviol glycoside which overexpresses a heterologous polypeptide which mediates steviol glycoside transport.

12. A process for the preparation of a steviol glycoside which comprises fermenting a recombinant host according to any one of the preceding embodiments in a suitable fermentation medium and, optionally, recovering the steviol glycoside.

13. A process according to embodiment 12 for the preparation of a steviol glyocisde, optionally wherein the process is carried out on an industrial scale.

14. A fermentation broth comprising a steviol glycoside obtainable by the process according to embodiment 12 or 13.

15. A steviol glycoside obtained by a process according to embodiment 12 or 13 or obtained from a fermentation broth according to embodiment 14.

16. A composition obtainable by a process according to embodiment 12 or 13, a composition comprising two or more steviol glycosides obtained by a process according to embodiment 12 or 13 or a composition obtained from a fermentation broth according to embodiment 14.

17. A foodstuff, feed or beverage which comprises a steviol glycoside according to claim 15 or a composition according to claim 16.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

EXAMPLES

General

Standard genetic techniques, such as overexpression of enzymes in the host cells, as well as for additional genetic modification of host cells, are known methods in the art, such as described in Sambrook and Russel (2001) "Molecular Cloning: A Laboratory Manual ($3^{rd}$ edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation and genetic modification of fungal host cells are known from e.g. EP-A-0 635 574, WO 98/46772, WO 99/60102 and WO 00/37671.

Example 1: Description of Steviol Glycoside Production Strain ML14094 (MAT-A Lineage)

Two *Yarrowia lipolytica* strains of mating types MATA and MATB were engineered for steviol glycoside production. These strains were mated, the diploid sporulated, and spores with steviol glycoside production were selected. One of these spores was further developed for the production of steviol glycosides, including the production of Rebaudioside A.

Step 1: Strain ML10371 (MAT-A, lys1-, ura3-, leu2-) was transformed with 5 defined DNA fragments. All transformations were carried out via a lithium acetate/PEG fungal transformation protocol method and transformants were selected on minimal medium, YPD+100 ug/ml nourseothricin or YPD+100 ug/ml hygromycin, as appropriate.

1) a 7.0 kb DNA fragment isolated by gel purification following Hindlll/NotI digestion of plasmid MB6969 (FIG. 1). This construct encodes a synthetic construct for the overexpression of UGT2_1a (SEQ ID NO: 1) linked to the pPGM promoter (SEQ ID NO: 2) and xprT terminator (SEQ ID NO: 9) and the HPH hygromycin resistance gene, together flanked by lox sites (Güldener et al, 1996, Lambert et al, 2007), and a synthetic construct for the overexpression of the codon optimized *Y. lipolytica* hydroxymethylglutaryl-coenzyme A reductase open reading frame lacking the 5' membrane anchor sequence (tHMGopt: SEQ ID NO: 15) linked to the pHSP promoter (SEQ ID NO: 3) and cwpT terminator (SEQ ID NO: 10).

Figure 2:
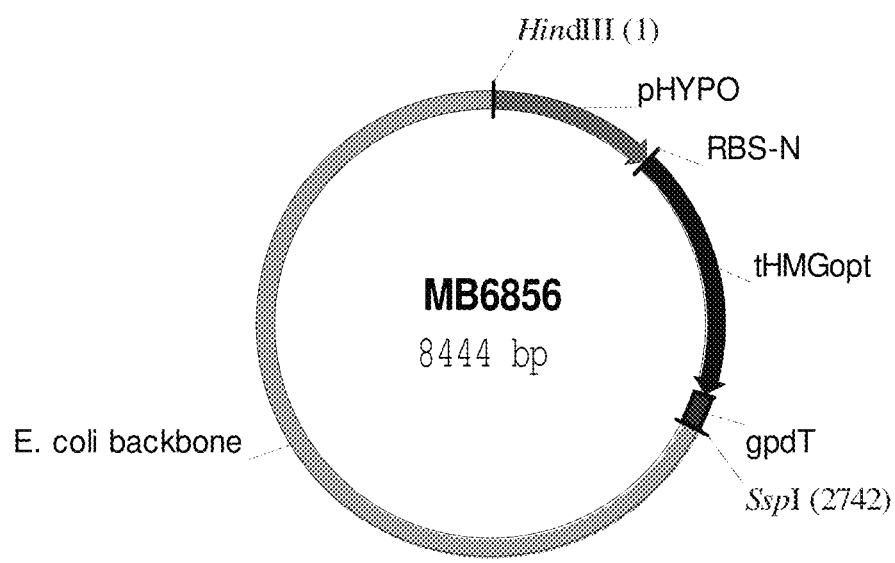
FIG. 2 sets out a schematic representation of the plasmid MB6856, encoding tHMG.

2) a 2.7 kb DNA fragment isolated by gel purification following Hindlll/SspI digestion of MB6856 (FIG. 2). This construct encodes tHMGopt (SEQ ID NO: 15) linked to the pHYPO promoter (SEQ ID NO: 4) and gpdT terminator (SEQ ID NO: 11).

Figure 3:
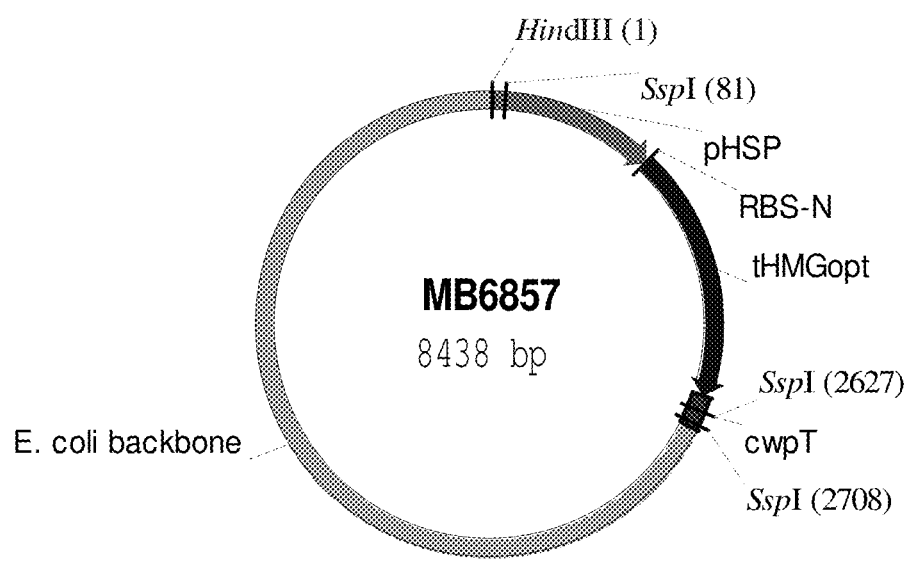
FIG. 3 sets out a schematic representation of the plasmid MB6857, encoding tHMG.

3) a 2.5 kb DNA fragment isolated by gel purification following SspI digestion of MB6857 (FIG. 3). This construct encodes tHMGopt (SEQ ID NO: 15) linked to the pHSP promoter (SEQ ID NO: 3) and cwpT terminator (SEQ ID NO: 10).

Figure 4:
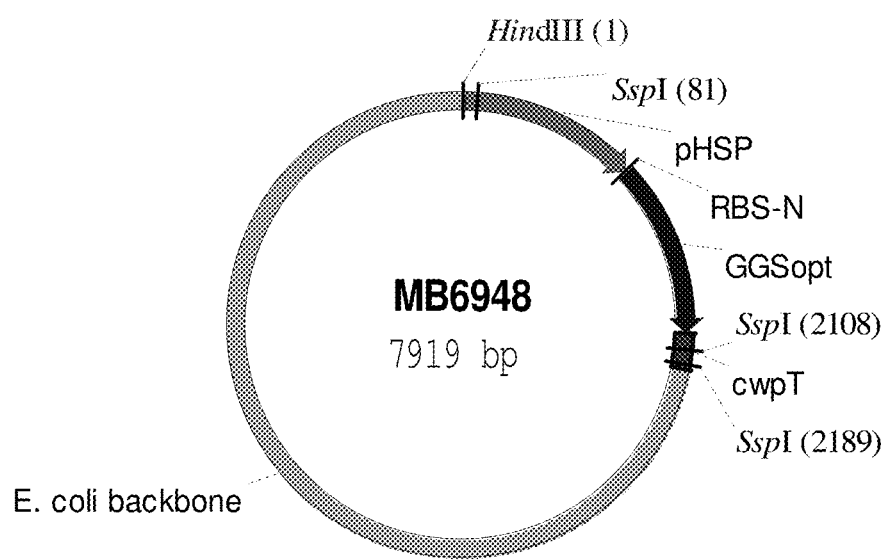
FIG. 4 sets out a schematic representation of the plasmid MB6948, encoding GGS.

4) a 2.0 kb DNA fragment isolated by gel purification following SspI digestion of MB6948 (FIG. 4). This construct encodes a synthetic construct for the overexpression of the codon optimized *Y. lipolytica* geranyl-geranyl-pyrophosphate synthetase (GGSopt: SEQ ID NO: 16) linked to the pHSP promoter (SEQ ID NO: 3) and cwpT terminator (SEQ ID NO: 10).

Figure 5:
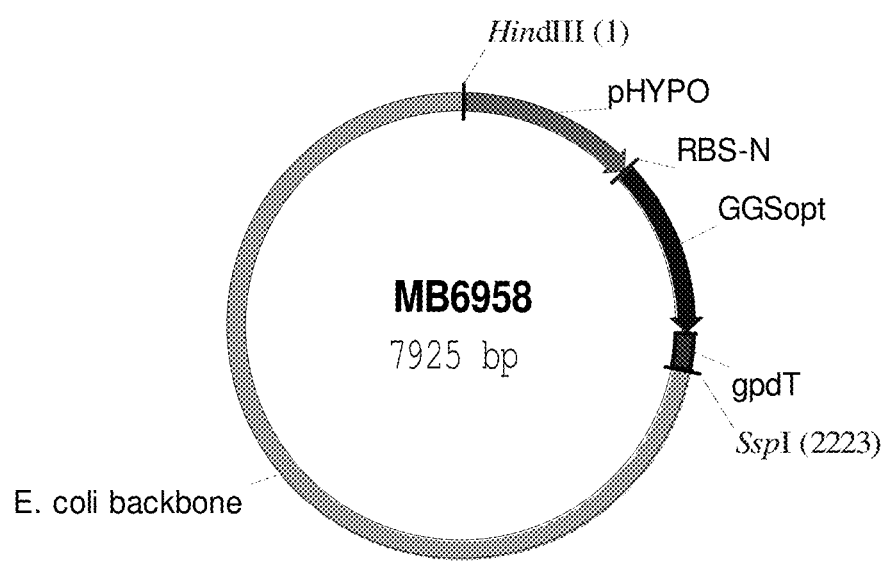
FIG. 5 sets out a schematic representation of the plasmid MB6958, encoding GGS.

5) a 2.2 kb DNA fragment isolated by gel purification following Hindlll/SspI digestion of MB6958 (FIG. 5). This construct encodes GGSopt (SEQ ID NO: 16) linked to the pHYPO promoter (SEQ ID NO: 4) and gpdT terminator (SEQ ID NO: 11). The resulting strain was denoted ML13462.

Figure 6:
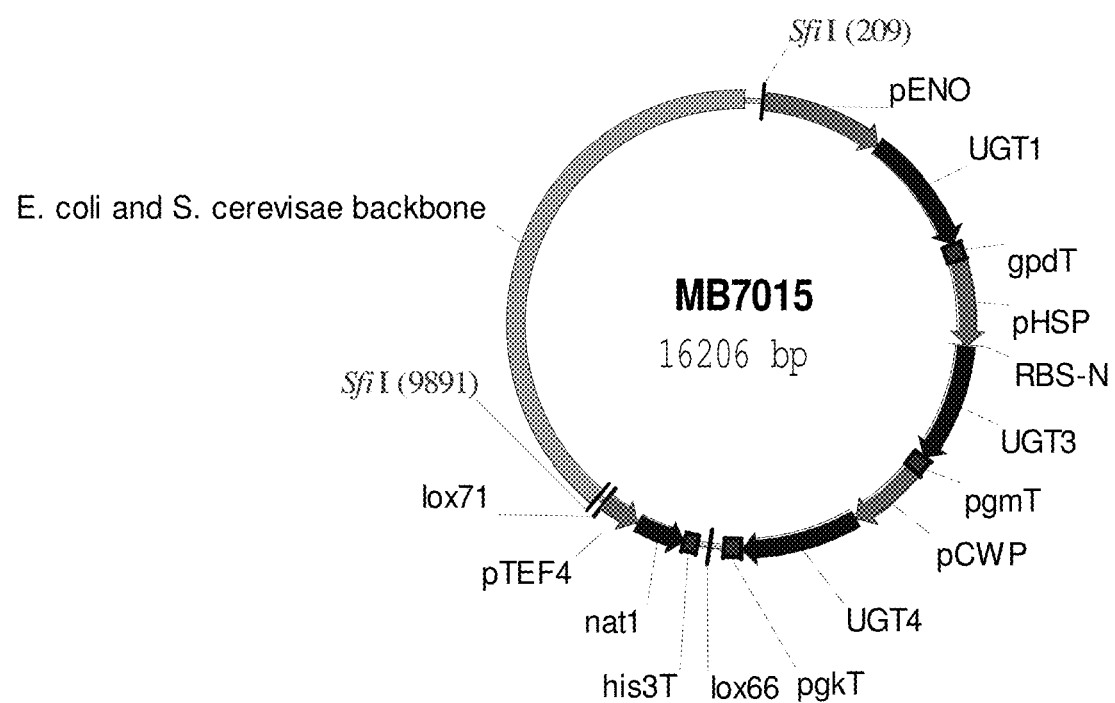
FIG. 6 sets out a schematic representation of the plasmid MB7015, encoding UGT1, UGT3, UGT4, NAT.

Step 2. Strain ML13462 was transformed with a 9.7 kb fragment isolated by gel purification following Sfil digestion of plasmid MB7015 (FIG. 6). This construct encodes a synthetic construct for the overexpression of UGT1 (SEQ ID NO: 17) linked to the pENO (SEQ ID NO: 5) promoter and gpdT terminator (SEQ ID NO: 11), UGT3 (SEQ ID NO: 18) linked to the pHSP promoter (SEQ ID NO: 3) and pgmT terminator (SEQ ID NO: 12), UGT4 (SEQ ID NO: 19) linked to the pCWP (SEQ NO: 6) promoter and pgkT terminator (SEQ ID NO: 13), and the lox-flanked nourseothricin resistance marker (NAT). Note that placement of lox sites allows for subsequent removal of nourseothricin resistance via CRE recombinase mediated recombination. A nourseothricin resistant isolate was denoted ML13500.

Figure 7:
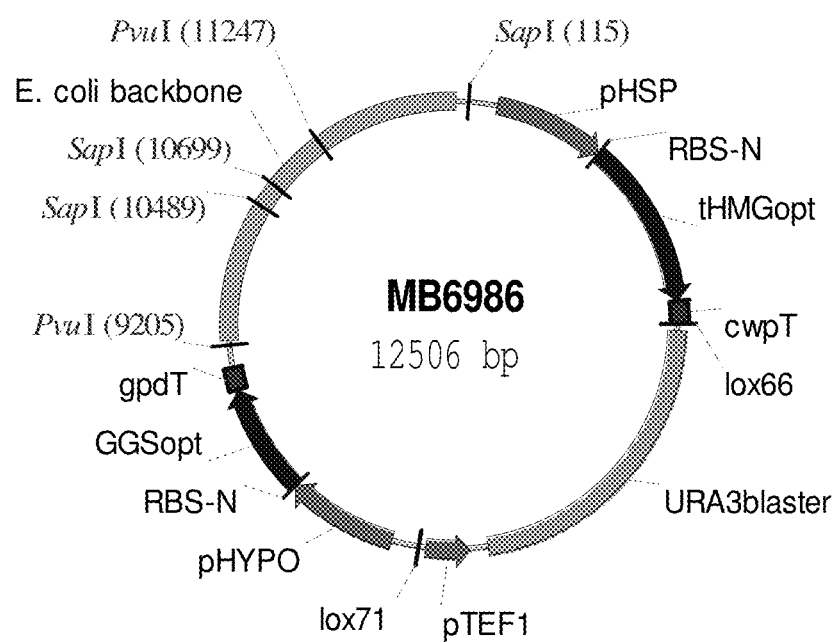
FIG. 7 sets out a schematic representation of the plasmid MB6986, encoding tHMG, URA3, GGS.

Step 3. Strain ML13500 was transformed with a 9.1 kb fragment isolated by gel purification following Pvul/SapI digestion of plasmid MB6986 (FIG. 7). This construct encodes tHMGopt (SEQ ID NO: 15) linked to the pHSP promoter (SEQ ID NO: 3) and cwpT terminator (SEQ ID NO: 10), the lox-flanked URA3blaster prototrophic marker, and GGSopt (SEQ ID NO: 16) linked to the pHYPO promoter (SEQ ID NO: 4) and gpdT terminator (SEQ ID NO: 11). Transformants were selected on minimal medium lacking uracil. One selected uracil prototroph was denoted ML13723.

Figure 8:
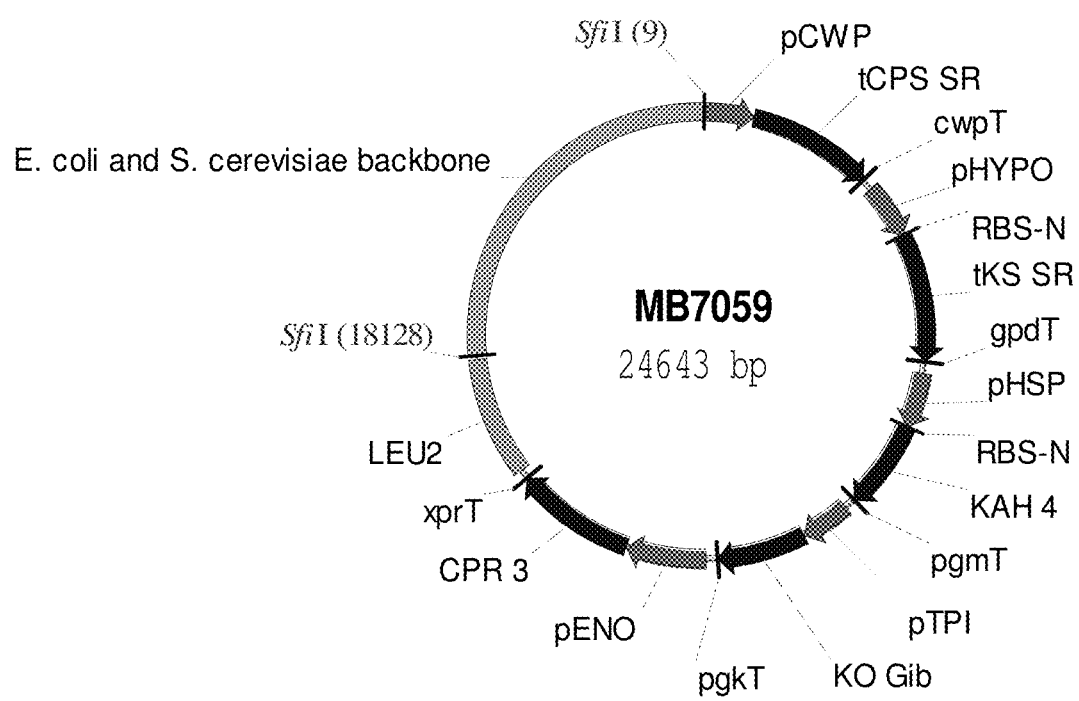
FIG. 8 sets out a schematic representation of the plasmid MB7059, encoding tCPS_SR, tKS_SR, KAH_4, KO_Gib, CPR_3, LEU2.

Step 4. Strain ML13723 was transformed with an 18.1 kb fragment isolated by gel purification following Sfil digestion of plasmid MB7059 (FIG. 8). MB7059 encodes the tCPS_SR (SEQ ID NO: 20) linked to pCWP promoter (SEQ ID NO: 6) and cwpT terminator (SEQ ID NO: 10), the tKS_SR (SEQ ID NO: 21) linked to the pHYPO promoter (SEQ ID NO: 4) and gpdT terminator (SEQ ID NO: 11), the KAH_4 (SEQ ID NO: 22) linked to the pHSP promoter (SEQ ID NO: 3) and pgmT terminator (SEQ ID NO: 12), the KO_Gib (SEQ ID NO: 23) linked to the pTPI promoter (SEQ ID NO: 7) and pgkT terminator (SEQ ID NO: 13), the CPR_3 (SEQ ID NO: 24) linked to the pENO promoter (SEQ ID NO: 5) and xprT terminator (SEQ ID NO: 9) and the native *Y. lipolytica* LEU2 locus. One selected rebaudioside A-producing transformant was denoted ML14032.

Step 5. Strain ML14032 was struck to YPD and grown overnight and then struck to 5-FOA plates to allow for recombination mediated loss of the URA3 marker introduced previously. One selected 5-FOA resistant transformant was denoted ML14093.

Figure 9:
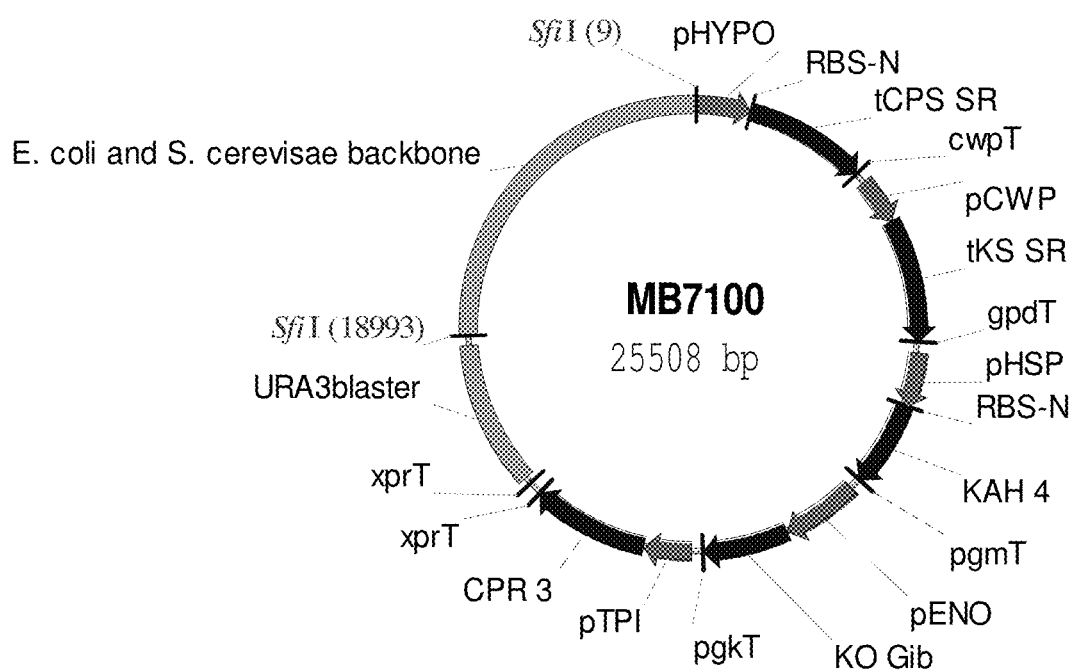
FIG. 9 sets out a schematic representation of the plasmid MB7100, encoding tCPS_SR, tKS_SR, KAH_4, KO_Gib, CPR_3, URA3.

Step 6. Strain ML14093 was transformed with a 19.0 kb fragment isolated by gel purification following Sfil digestion of plasmid MB7100 (FIG. 9). MB7100 encodes the tCPS_SR (SEQ ID NO: 20) linked to the pHYPO promoter (SEQ ID NO: 4) and cwpT terminator (SEQ ID NO: 10), the tKS_SR (SEQ ID NO: 21) linked to the pCWP promoter (SEQ ID NO: 6) and gpdT terminator (SEQ ID NO: 11), the KAH_4 (SEQ ID NO: 22) linked to the pHSP promoter (SEQ ID NO: 3) and pgmT terminator (SEQ ID NO: 12), the KO_Gib (SEQ ID NO: 23) linked to the pENO promoter (SEQ ID NO: 5) and pgkT terminator (SEQ ID NO: 13), the CPR_3 (SEQ ID NO: 24) linked to the pTPI promoter (SEQ ID NO: 7) and xprT terminator (SEQ ID NO: 9) and URA3blaster prototrophic marker. Transformants were selected on minimal medium lacking uracil. One selected rebaudioside A producing uracil prototroph was denoted ML14094.

Example 2. Description of Steviol Glycoside Production Strain ML14087 (MAT-B Lineage)

Step 1. Strain ML13206 (MAT-B, ade1-, ure2-, leu2-) was transformed with 5 defined DNA fragments. All transformations were carried out via a lithium acetate/PEG fungal transformation protocol method and transformants were selected on minimal medium, YPD+100 ug/ml nourseothricin or YPD+100 ug/ml hygromycin, as appropriate.

1) a 7.0 kb DNA fragment isolated by gel purification following Hindlll/Notl digestion of plasmid MB6969 (FIG. 1). This construct encodes a synthetic construct for the overexpression of the codon pair optimized (CpO) ORF of UGT2_1a (SEQ ID NO: 1) linked to the pPGM (SEQ ID NO: 2) promoter and xprT terminator (SEQ ID NO: 9) and the HPH hygromycin resistance gene, together flanked by lox sites (Güldener et al, 1996, Lambert et al, 2007), and a synthetic construct for the overexpression of the codon optimized *Y. lipolytica* hydroxymethylglutaryl-coenzyme A reductase open reading frame lacking the 5' membrane anchor sequence (tHMGopt: SEQ ID NO: 15) linked to the pHSP promoter (SEQ ID NO: 3) and cwpT terminator (SEQ ID NO: 10).

2) a 2.7 kb DNA fragment isolated by gel purification following Hindlll/Sspl digestion of MB6856 (FIG. 2). This construct encodes tHMGopt (SEQ ID NO: 15) linked to the pHYPO promoter (SEQ ID NO: 4) and gpdT terminator (SEQ ID NO: 11).

3) a 2.5 kb DNA fragment isolated by gel purification following Sspl digestion of MB6857 (FIG. 3). This construct encodes tHMGopt (SEQ ID NO: 15) linked to the pHSP promoter (SEQ ID NO: 3) and cwpT terminator (SEQ ID NO: 10).

4) a 2.0 kb DNA fragment isolated by gel purification following Sspl digestion of MB6948 (FIG. 4). This construct encodes a synthetic construct for the overexpression of the codon optimized *Y. lipolytica* geranyl-geranyl-pyrophosphate synthetase (GGSopt: SEQ ID NO: 16) linked to the pHSP promoter (SEQ ID NO: 3) and cwpT terminator (SEQ ID NO: 10).

5) a 2.2 kb DNA fragment isolated by gel purification following Hindlll/Sspl digestion of MB6958 (FIG. 5). This construct encodes GGSopt (SEQ ID NO: 16) linked to the pHYPO (SEQ ID NO: 4) promoter and gpdT terminator (SEQ ID NO: 11). The resulting strain was denoted ML13465.

Step 2. Strain ML13465 was Transformed with 2 Defined DNA Fragments:

1). a 9.7 kb fragment isolated by gel purification following Sfil digestion of plasmid MB7015 (FIG. 6). This construct encodes a synthetic construct for the overexpression of UGT1 (SEQ ID NO: 17) linked to the pENO promoter (SEQ ID NO: 5) and gpdT (SEQ ID NO: 11) terminator, UGT3 (SEQ ID NO: 18) linked to the pHSP promoter (SEQ ID NO: 3) and pgmT terminator (SEQ ID NO: 12), UGT4 (SEQ ID NO: 19) linked to the pCWP promoter (SEQ ID NO: 6) and pgkT terminator (SEQ ID NO: 13), and the lox-flanked nourseothricin resistance marker (NAT). Note that placement of lox sites allows for subsequent removal of nourseothricin resistance via CRE recombinase mediated recombination.

Figure 10:
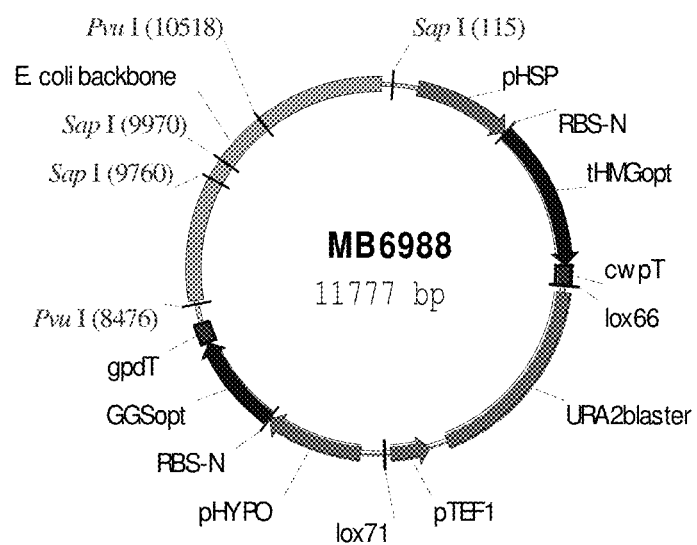
FIG. 10 sets out a schematic representation of the plasmid MB6988, encoding tHMG, URA2, GGS.

2). a 9.1 kb fragment isolated by gel purification following Pvul/Sapl digestion of plasmid MB6988 (FIG. 10). This construct encodes tHMGopt (SEQ ID NO: 15) linked to the pHSP promoter (SEQ ID NO: 3) and cwpT terminator (SEQ ID NO: 10), the lox-flanked URA2blaster prototrophic marker, and GGSopt (SEQ ID NO: 16) linked to the pHYPO promoter (SEQ ID NO: 4) and gpdT terminator (SEQ ID NO: 11). Strains were selected on YPD+100 ug/ml nourseothricin and replica plated to minimal medium lacking uracil. A nourseothricin resistant, uracil prototrophic isolate was denoted ML13490

Step 3. Strain ML13490 was struck to YPD and grown overnight and then struck to 5-FOA plates to allow for recombination mediated loss of the URA2 marker introduced previously. One selected 5-FOA resistant transformant was denoted ML13501.

Step 4. Strain ML13501 was transformed with a 9.1 kb fragment isolated by gel purification following Pvul/Sapl digestion of plasmid MB6988 (FIG. 10). Transformants were selected on minimal medium lacking uracil. One selected uracil prototroph was denoted ML13724.

Figure 11:
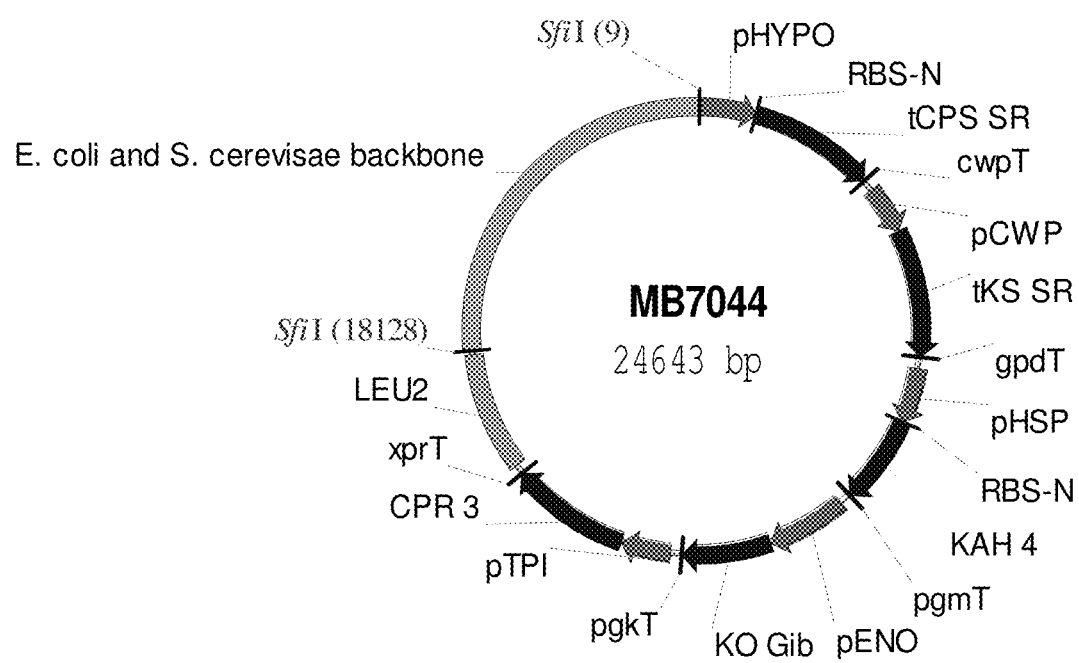
FIG. 11 sets out a schematic representation of the plasmid MB7044, encoding tCPS_SR, tKS_SR, KAH_4, KO_Gib, CPR_3, LEU2.

Step 5. Strain ML13724 was transformed with an 18.1 kb fragment isolated by gel purification following Sfil digestion of plasmid MB7044 (FIG. 11). MB7044 encodes the tCPS_SR (SEQ ID NO: 20) linked to the pHYPO promoter (SEQ ID NO: 4) and cwpT terminator (SEQ ID NO: 10), the tKS_SR (SEQ ID NO: 21) linked to the pCWP promoter (SEQ ID NO: 6) and gpdT terminator (SEQ ID NO: 11), the KAH_4 (SEQ ID NO: 22) linked to the pHSP promoter (SEQ ID NO: 3) and pgmT terminator (SEQ ID NO: 12), the KO_Gib (SEQ ID NO: 23) linked to the pENO promoter (SEQ ID NO: 5) and pgkT terminator (SEQ ID NO: 13), the CPR_3 (SEQ ID NO: 24) linked to the pTPI promoter (SEQ ID NO: 7) and xprT terminator (SEQ ID NO: 9) and the LEU2 locus. One selected rebaudioside A-producing transformant was denoted ML14044.

Step 6. Strain ML14044 was struck to YPD and grown overnight and then struck to 5-FOA plates to allow for recombination mediated loss of the URA2 marker introduced previously. One selected 5'-FOA resistant transformant was denoted ML14076.

Figure 12:
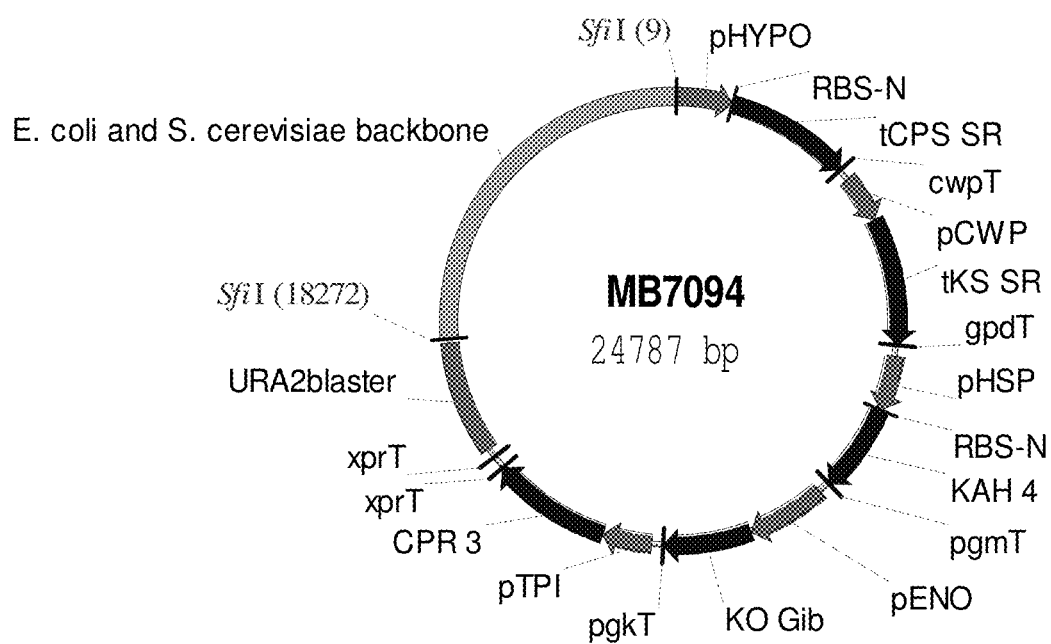
FIG. 12 sets out a schematic representation of the plasmid MB7094, encoding tCPS_SR, tKS_SR, KAH_4, KO_Gib, CPR_3, URA2.

Step 7. Strain ML14076 was transformed with a 19.0 kb fragment isolated by gel purification following Sfil digestion of plasmid MB7094 (FIG. 12). MB7094 encodes the tCPS_SR (SEQ ID NO: 20) linked to the pHYPO promoter (SEQ ID NO: 4) and cwpT terminator (SEQ ID NO: 10), the tKS_SR (SEQ ID NO: 21) linked to the pCWP promoter (SEQ ID NO: 6) and gpdT terminator (SEQ ID NO: 11), the KAH_4 (SEQ ID NO: 22) linked to the pHSP promoter (SEQ ID NO: 3) and pgmT terminator (SEQ ID NO: 12), the KO_Gib (SEQ ID NO: 23) linked to the pENO promoter (SEQ ID NO: 5) and pgkT terminator (SEQ ID NO: 13), the CPR_3 (SEQ ID NO: 24) linked to the pTPI promoter (SEQ ID NO: 7) and xprT terminator (SEQ ID NO: 9) and URA2blaster prototrophic marker. Transformants were selected on minimal medium lacking uracil. One selected rebaudioside A producing uracil prototroph was denoted ML14087.

Example 3. Mating MATA and MATB Lineage and Selecting Steviol Glycoside-Producing Progeny Strains of opposite mating types (ML14094 and ML14087) with complementary nutritional deficiencies (ADE1+ lys1- and ade1- LYS1+) were allowed to mate and then plated on selective media that would allow only diploids to grow (minimal media lacking both adenine and lysine). Diploid cells (ML14143) were then induced to undergo meiosis and sporulation by starvation, and the resulting haploid progenies were replica-plated to identify prototrophic isolates with hygromycin and nourseothricin resistance. One selected rebaudioside A-producing strain was denoted ML14737

Example 4. Making the Strain UGT2 1a-Free

Figure 13:
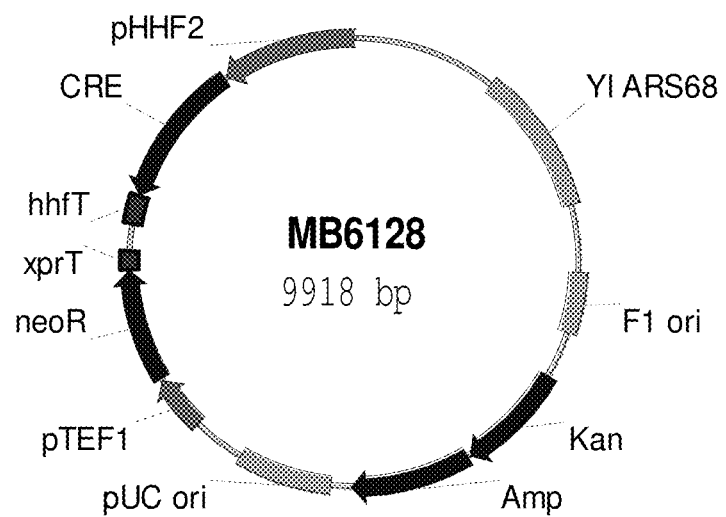
FIG. 13 sets out a schematic representation of the plasmid MB6128, encoding CRE, neoR.

The hygromycin antibiotic marker and the nourseothricin antibiotic marker were removed from strain ML14737 after transformation with MB6128 (FIG. 13) which encodes a construct for constitutive overexpression of the CRE recombinase. CRE recombinase deletes the antibiotics markers by recombination over the Lox66 and Lox71 sites. An inactive Lox72 site is left in the genome (Güldener et al, 1996, Lambert et al, 2007). Plasmid MB6128 is a CEN plasmid which replicates episomally in *Yarrowia lipolytica* and which contains the CRE recombinase coding region under control of the native *Yarrowia lipolytica* pHHF promoter and hhfT terminator, and a neoR (encoding for G418 resistance) under the control of the native *Yarrowia lipolytica* pTEF1 promoter and xprT terminator. After selection of MB6128 transformants on YPD+G418 and screening for transformants that lost hygromycin and nourseothricin resistance by successful Cre-Lox recombination, the sensitive colonies were grown on non-selective medium to remove the MB6128 CEN plasmid (spontaneous loss of the CEN plasmid). The resulting antibiotic marker-free variant is denoted ML14869. This strain no longer produces rebaudioside A due to the loss of UGT2_1a along with the hygromycin resistance and produces the intermediate rubusoside instead.

Example 5. Introduction of UGT2 10b

ML14869 was transformed with a 4.2 kb DNA fragment produced by PCR and purified following gel electrophoresis. The fragment encoded a sequence optimized variant of UGT2_10 b (SEQ ID NO: 25) and hygromycin resistance. The DNA fragment was generated by fusion PCR as follows. UGT2_10 b was codon pair optimized for expression in *Y. lipolytica* and synthesized by DNA2.0, linked to the native *Yarrowia lipolytica* pHSP promoter and gpdT terminator and flanked by connector sequences. This 1.4 kb DNA fragment was amplified using appropriate oligos and purified by gel electrophoresis. The HPH marker was flanked by lox sites, and linked to the *Ashbya gossypii* pTEF1 promoter and tef1T terminator and flanked by connector sequences. This 1.8 kb DNA fragment was amplified using appropriate oligos and purified by gel electrophoresis. A 4.2 kb DNA fragment was obtained by PCR using these two DNA fragments with followed by gel electrophoresis and purification. Transformation of ML14869 with this defined DNA fragment and selection on YPD+100 ug/ml hygromycin yielded the rebaudioside A producing strain ML14937.

Example 6. Making Strain ML14937 Marker-Free

The hygromycin antibiotic marker was removed from strain ML14937 after transformation with MB6128 (FIG. 13) which encodes a construct for constitutive overexpression of the CRE recombinase. CRE recombinase deletes the antibiotics markers by recombination over the Lox66 and Lox71 sites. An inactive Lox72 site is left in the genome (Güldener et al, 1996, Lambert et al, 2007). Plasmid MB6128 is a CEN plasmid which replicates episomally in *Yarrowia lipolytica* and which contains the CRE recombinase coding region under control of the native *Yarrowia lipolytica* pHHF promoter and hhfT terminator and a neoR (encoding for G418 resistance) under the control of the native *Yarrowia lipolytica* pTEF1 promoter and xprT terminator. After selection of MB6128 transformants on YPD+G418 and screening for transformants that lost hygromycin and nourseothricin resistance by successful Cre-Lox recombination, the sensitive colonies were grown on non-selective medium to remove the MB6128 CEN plasmid (spontaneous loss of the CEN plasmid). The resulting antibiotic marker-free variant is denoted ML14958.

Example 7. Transformation with Extra Gene Copies

Figure 14:
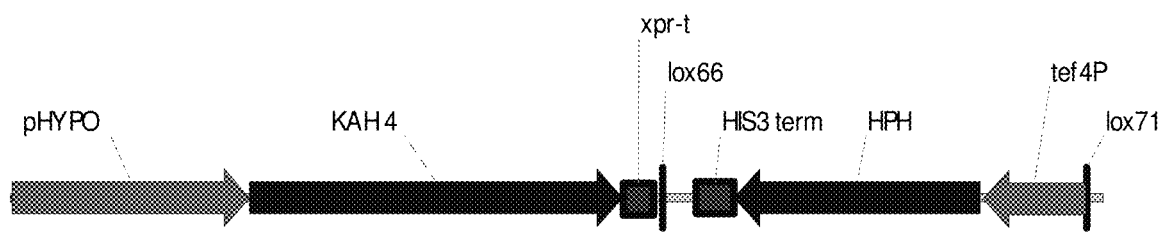
FIG. 14 sets out a schematic representation of the construct containing KAH and HPH.

Strain ML14958 was struck to YPD and grown overnight and then struck to 5-FOA plates to allow for recombination-mediated loss of the URA2 marker. One selected 5'-FOA resistant transformant was denoted ML15075. Strain ML15075 was transformed with 3 defined DNA fragments and selected for transformation on YPD with 100 ug/ml hygromycin. The three fragments were as follows:

1) a 4.6 kb DNA fragment encoding the KAH open reading frame linked to the native *Y. lipolytica* pHYPO promoter and the xprT terminator and also encoding the HPH hygromycin resistance gene flanked by lox sites, produced by PCR and purified following gel electrophoresis. Sequences were assembled in *Saccharomyces cerevisiae*, and DNA from this *S. cerevisiae* strain was used as template for PCR yielding the 4.6 kb DNA fragment (see FIG. 14) used to transform ML15075.

Figure 15:
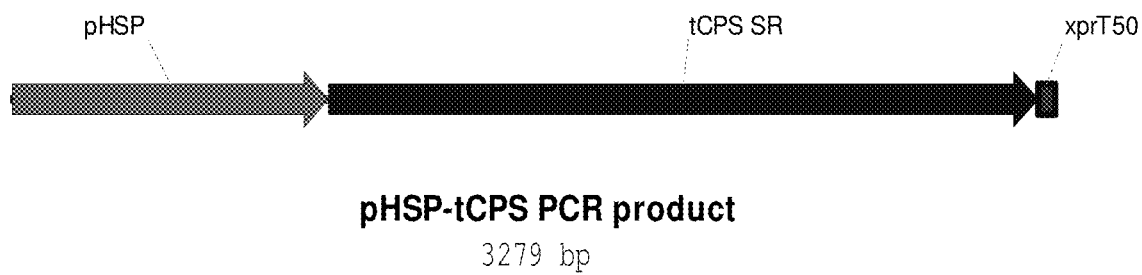
FIG. 15 sets out a schematic representation of the construct containing tCPS_SR.

2) a 3.3 kb DNA fragment encoding the tCPS open reading frame linked to the native *Y. lipolytica* pHSP promoter and xprT terminator, produced by PCR and purified following gel electrophoresis. Sequences were assembled in *Saccharomyces cerevisiae*, and DNA from this *S. cerevisiae* strain was used as template for PCR yielding the 3.3 kb DNA fragment (FIG. 15) used to transform ML15075.

Figure 16:
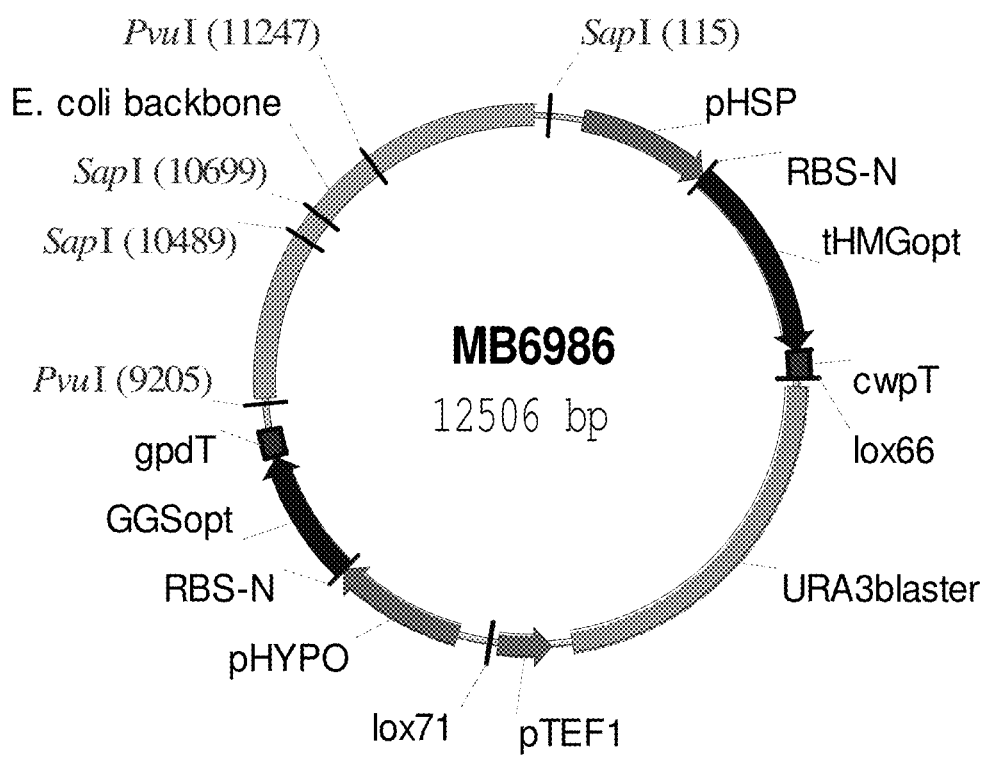
FIG. 16 sets out a schematic representation of the plasmid MB6986, encoding tHMG, URA3, GGS.

3) a 9.1 kb fragment isolated by gel purification following Pvul/Sapl digestion of plasmid MB6986 (FIG. 16). This construct encodes tHMG linked to the native *Y. lipolytica* HSP promoter and CWP terminator, the lox-flanked URA3blaster prototrophic marker, and GGS1 linked to the native *Y. lipolytica* HYPO promoter and GPD terminator. ML15075 is auxotrophic due to a mutation in ura2, so this fragment was not selected for.

One selected hygromycin-resistant transformant was denoted ML15085.

Example 8. Transformation of Extra Copies of tHMG and GGS

Strain ML15085 was transformed with a 8.4 kb fragment isolated by gel purification following Pvul/Sapl digestion of plasmid MB6988 (FIG. 10). This construct encodes tHMGopt linked to the native *Y. lipolytica* pHSP promoter and cwpT terminator, the lox-flanked URA2blaster prototrophic marker, and GGSopt linked to the native *Y. lipolytica* pHYPO promoter and gpdT terminator. Transformants were selected on minimal medium lacking uracil. One selected uracil prototroph was denoted ML15086.

Example 9. Making Strain ML15086 Marker-Free

The hygromycin antibiotic marker was removed from strain ML15086 after transformation with MB6128 (FIG. 13) which encodes a construct for constitutive overexpression of the CRE recombinase. CRE recombinase deletes the antibiotics markers by recombination over the Lox66 and Lox71 sites. An inactive Lox72 site is left in the genome (G üldener et al, 1996, Lambert et al, 2007). Plasmid MB6128 is a CEN plasmid which replicates episomally in *Yarrowia lipolytica* and which contains the CRE recombinase coding region under control of the native *Yarrowia lipolytica* pHHF promoter and hhfT terminator and a neoR (encoding for G418 resistance) under the control of the native *Yarrowia lipolytica* pTEF1 promoter and xprT terminator.

After selection of MB6128 transformants on YPD+G418 and screening for transformants that lost hygromycin and nourseothricin resistance by successful Cre-Lox recombination, the sensitive colonies were grown on non-selective medium to remove the MB6128 CEN plasmid (spontaneous loss of the CEN plasmid). One prototrophic, antibiotic marker-free variant is denoted ML15087.

Example 10. Disruption of YALI0C08701 in *Y. lipolytica* ML15087

To increase the efficiency of targeted transporter disruptions and avoid integration events at other loci in the genome than targeted for, YALI0C08701 (SEQ ID NO: 26), an important factor in non-homologous end joining, was disrupted. Disruption constructs were designed based on single cross-over integration using internal homologous fragments to target the disruption construct to the YALI0C08701 ORF. The internal homologous fragments used to assemble the disruption constructs were PCR amplified from *Y. lipolytica* genomic DNA using suitable primers which were elongated with appropriate connector sequences. The total length of the PCR fragments was 600 bp. 500 bp of these fragments are homologous to the targeted YALI0C08701 and 50 bp to the vector backbone and KanMX marker cassette. The KanMX marker cassette was PCR amplified with suitable primers. For both flanks and marker cassette six 50 µl PCR reactions were performed using Phusion polymerase (New England Biolabs) according to suppliers' instructions. The PCR products were purified and concentrated using Nucleo-Spin Gel and PCR Clean-up Kit (Machery Nagel).

Figure 17:
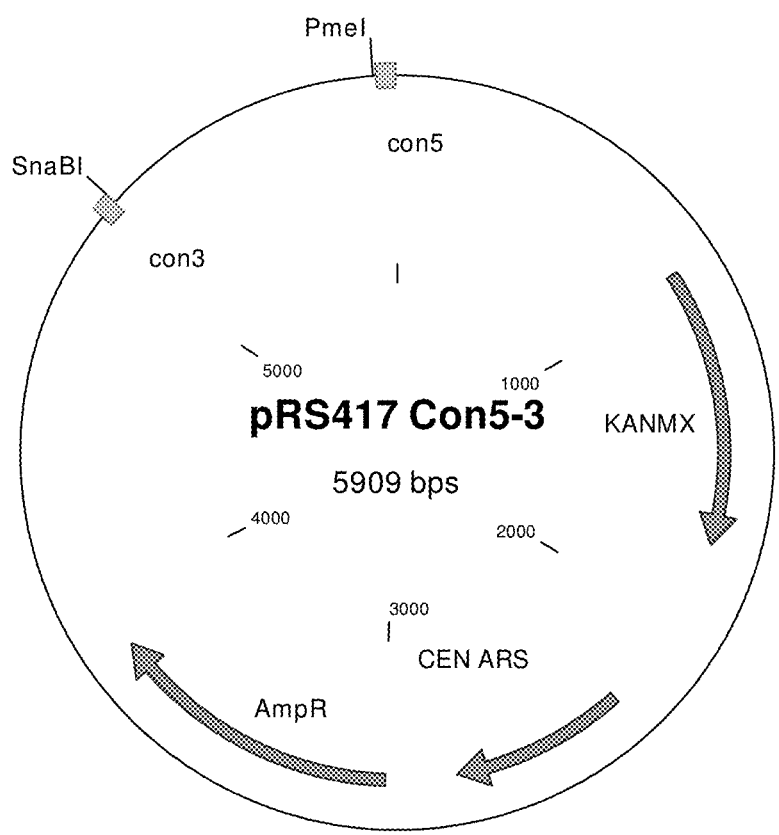
FIG. 17 sets out a schematic representation of the plasmid pRS417 Con5-3.

The flanks and marker were assembled in the SnaBl/PmeI digested pRS417 5_3 (FIG. 17) shuttle vector backbone in-vivo by transforming both flanks, the KanMX fragment and the linear pRS417 5_3 shuttle vector to *S. cerevisiae* CEN.PK113-7D. After transformation and recovery for 2 hours in YEPhD at 30° C. the cells were plated on YEPhD agar with 200 µg/ml G418 (Invitrogen). The plates were incubated at 30° C. for 2 days. Transformants were cultured in YEPD+200 µg/ml G418 at 30° C. Plasmid DNA was isolated and purified.

Correct assembly of the disruption cassettes was established with diagnostic PCR. The expression cassettes were PCR amplified in six 50 µl PCR reactions. The PCR product was purified and concentrated using NucleoSpin Gel and PCR Clean-up Kit (Machery Nagel). 1 µg of the PCR amplified disruption cassette was transformed to *Y. lipolytica* strain ML15087. After transformation and recovery for 2 hours in YEPhD at 30° C. the cells were plated on YEPhD agar with 400 µg/ml G418. The plates were incubated at 30° C. for 2 days. Transformants were purified by re-streaking them on YEPhD agar with 400 µg/ml G418. One of the transformants was named STV2049. Correct integration was established with diagnostic PCR using appropriate oligo's.

Example 11. Disruption of Transporter YALI0E25201 in *Y. lipolytica* STV2049

Figure 18:
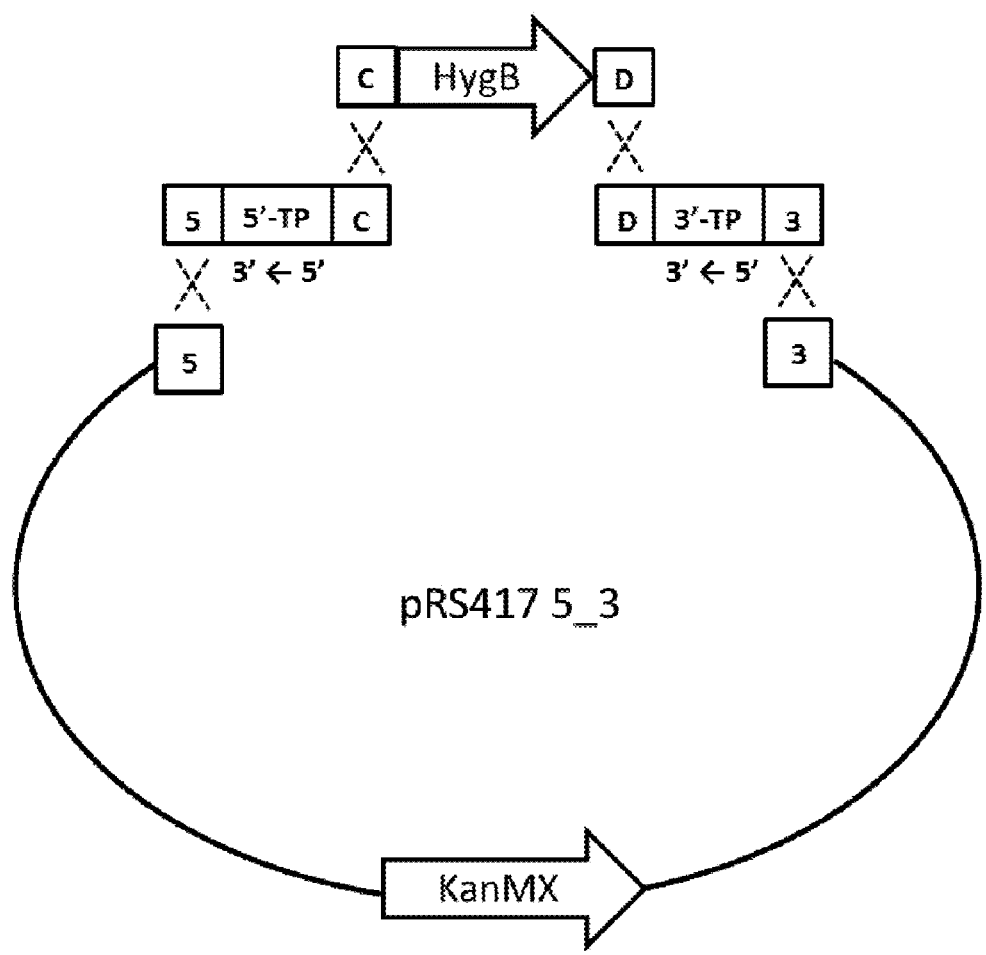
FIG. 18 sets out a schematic representation of the assembly of the HygB marker with the transporter internal fragments in plasmid pRS417 5-3.

Disruption constructs were designed based on single cross-over integration using internal homologues fragments to target the disruption construct to the YALI0E25201 ORF (SEQ ID NO: 27). The internal homologous fragments used to assemble the disruption constructs were ordered as synthetic DNA in the form of gBlocks (IDT) with a total length of 700 bp. 600 bp of these fragments are homologous to the targeted transporter YALI0E25201 and 50 bp to the vector backbone (5 and 3 connector sequence, FIG. 18) and HygB marker cassette (c and d connector sequence, FIG. 18). The HygB marker cassette was PCR amplified with suitable primers using Phusion polymerase (New England Biolabs) according to suppliers' instructions. The PCR product was purified and concentrated using NucleoSpin Gel and PCR Clean-up Kit (Machery Nagel).

The flanks and marker were assembled in the SnaBl/PmeI digested pRS417 5_3 shuttle vector backbone in-vivo by transforming both flanks, the HygB fragment and the linear pRS417 5_3 shuttle vector to *S. cerevisiae* CEN-PK-7D. See FIG. 18.

After transformation and recovery for 2 hours in YEPhD at 30° C. the cells were plated on YEPhD agar with 200 µg/ml G418 (Invitrogen). The plates were incubated at 30° C. for 2 days. Transformants were cultured in YEPD+200 µg/ml G418 at 30° C., 550 rpm and 80% humidity. Plasmid DNA was isolated and purified. Correct assembly of the disruption cassettes was established with diagnostic PCR.

Figure 19:
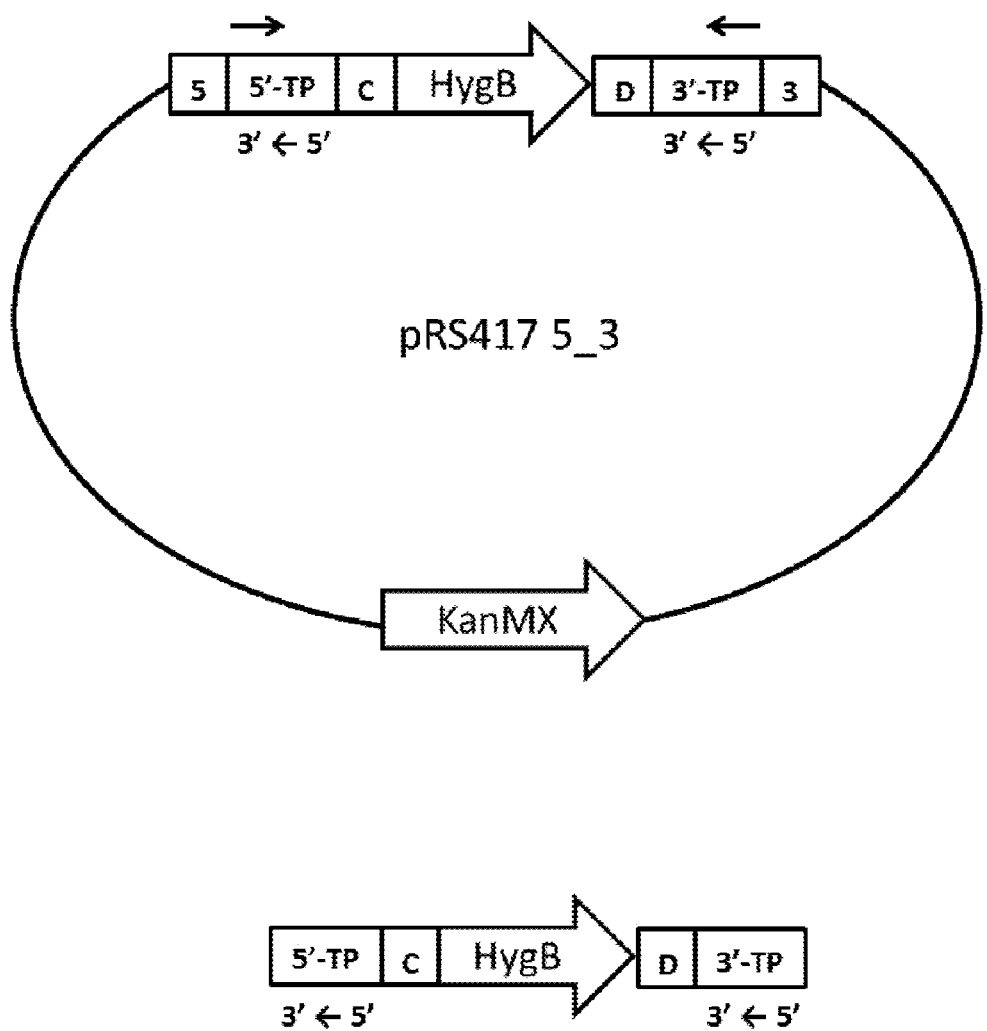
FIG. 19 sets out a schematic representation of the PCR amplification of the transporter disruption constructs off plasmid pRS417 5-3 containing the HYG marker and transporter internal fragments.
Figure 20:
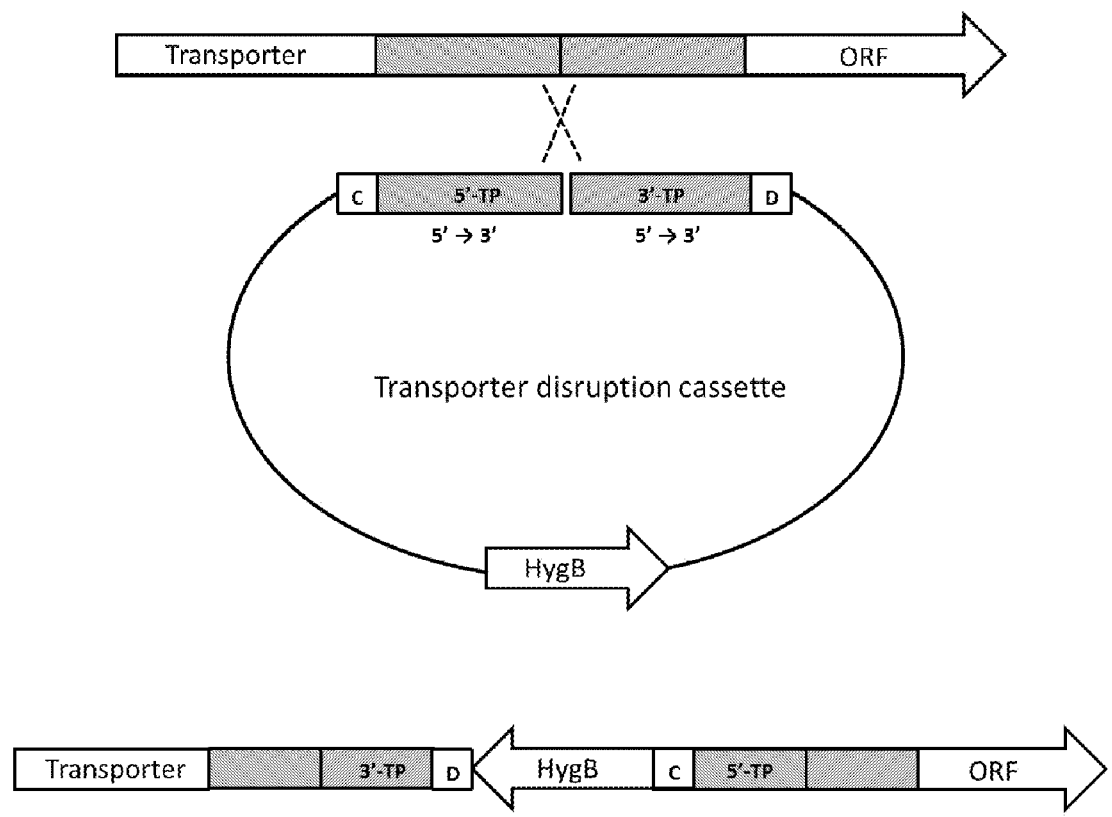
FIG. 20 sets out a schematic representation of the recombination event at the genome resulting in a disruption of the transporter gene and integration of the HygB marker.

The expression cassettes were PCR amplified (FIG. 19) in six 50 µl PCR reactions. The PCR product was purified and concentrated using NucleoSpin Gel and PCR Clean-up Kit (Machery Nagel). 1 µg of the PCR amplified disruption cassette was transformed to *Y. lipolytica* STV2049. After transformation and recovery for 2 hours in YEPhD at 30° C. the cells were plated on YEPhD agar with 100 µg/ml HygB (Invitrogen). The plates were incubated at 30° C. for 2 days. Transformants were purified by re-streaking them on YEPhD agar with 100 µg/ml HygB. Correct integration, as illustrated in FIG. 20, was established with diagnostic PCR using appropriate oligo's.

Example 12. Fermentation of *Y. Lipolytica* STV2049 and STV2049 YALI0E25201 Disruption Transformants A pre-culture was inoculated with colony material from YEPh-D agar. The pre-culture was grown in 96-Half Deep Well Plate containing 200 µl 0.5×YEP with 2% glucose per well. The plates were sealed with a breathable seal and incubated in an Infors incubator at 30° C., 80% humidity, 750 rpm for 48 hours.

40 µl of the 96-well pre-culture was used to inoculate a 24-well deep well plate containing 2.5 ml of 0.25×YEP with 5% glucose per well. Plates were sealed with a breathable seal and incubated in an Infors incubator at 30° C., 80% humidity, 500 rpm for 120 hours.

The 24-well plates were spun down in an MTP centrifuge and 1 ml of the supernatant was harvested. The remaining supernatant was decanted from the pellet. The supernatant fraction was diluted 1000 times in 33% Acetonitrile. The pellet was suspended in 2.5 ml milli-Q and 1 ml was transferred to a 96-well DWP. The plate was sealed with an aluminium seal and incubated for 10 minutes at 90° C. The plate was cooled down to room temperature and 0.5 ml of 100% Acetonitrile was added and homogenized. The plates were centrifuged at 2088×g for 10 minutes to pellet cell material and debris. The supernatant of the pellet fraction was diluted 33 times in 33% acetonitrile resulting in a combined 50 times dilution. Samples were analyzed for Rebaudioside A and other steviolglycosides using LC/MS.

We found that the strains that had the YALI0E25201 disruption produced lower titers of Rebaudioside A in the supernatant compared to the parent strain. The concentration of Rebaudioside A was approximately three fold lower in the transporter disruption strain compared to the parental strain (see Table 1).

TABLE 1

Rebaudioside A supernatant concentrations in 24-well fermentations. Six replicate cultures were performed for parent strain STV2049. Duplicate cultures of three independent STV2049 ΔYALI0E25201 transformants were performed. The averages are taken for the data in Table 1.

| Strain | RebA supernatant (mg/L) |
|---|---|
| STV2049 | 441 |
| STV2049 ΔYALI0E25201 A | 155 |

The observation that the concentration of Rebaudioside A in the supernatant is lower for the transporter disruption strain compared to the reference strain was also seen for Stevioside, Rubusoside, and to a lesser degree for Rebaudioside D and Steviol-19-monoside (see Tables 2 to 5).

TABLE 2

Stevioside supernatant concentrations in 24-well fermentations. Six replicate cultures were performed for parent strain STV2049. Duplicate cultures of three independent STV2049 ΔYALI0E25201 transformants were performed. The averages are taken for the data in Table 2.

| Strain | Stevioside supernatant (mg/L) |
|---|---|
| STV2049 | 144 |
| STV2049 ΔYALI0E25201 A | 46.9 |

TABLE 3

Rubusoside supernatant concentrations in 24-well fermentations. Six replicate cultures were performed for parent strain STV2049. Duplicate cultures of three independent STV2049 ΔYALI0E25201 transformants were performed. The averages are taken for the data in Table 3.

| strain | Rubusoside supernatant (mg/L) |
|---|---|
| STV2049 | 42.2 |
| STV2049 ΔYALI0E25201 A | 17.2 |

TABLE 4

Rebaudioside D supernatant concentrations in 24-well fermentations. Six replicate cultures were performed for parent strain STV2049. Duplicate cultures of three independent STV2049 ΔYALI0E25201 transformants were performed. The averages are taken for the data in Table 4.

| Strain | RebD supernatant (mg/L) |
|---|---|
| STV2049 | 39.7 |
| STV2049 ΔYALI0E25201 A | 32.6 |

TABLE 5

Steviol-19-monoside supernatant concentrations in 24-well fermentations. Six replicate cultures were performed for parent strain STV2049. Duplicate cultures of three independent STV2049 ΔYALI0E25201 transformants were performed. The averages are taken for the data in Table 5.

| Strain | Steviol-19-monoside supernatant (mg/L) |
|---|---|
| STV2049 | 35.7 |
| STV2049 ΔYALI0E25201 A | 20.2 |

The effect of disrupting the transporter gene was most pronounced on the transport of the aforementioned steviol glycosides, and not a consequence of a general decreased production of steviol glycosides. This is illustrated when the concentration of all steviol glycosides are measured in the pellet fraction (Table 6). Here it can be seen that in the YALI0E25201 disruption strain, the concentration of all steviol glycosides in the pellet fraction is increased in the transporter disruption strain, indicative of reduced transport.

TABLE 6

Concentration of the sum of all steviol glycosides (Rebaudioside A, Stevioside, Rebaudioside B, Rebaudioside D, Steviolbioside, Rubusoside, Steviol-19-monoside, Steviol-13-monoside and Rebaudioside M) in the pellet fraction in 24-well fermentations. Six replicate cultures were performed for parent strain STV2049. Duplicate cultures of three independent STV2049 ΔYALI0E25201 transformants were performed. The averages are taken for the data in Table 6.

| strain | Sum steviol glycosides pellet (uM) |
|---|---|
| STV2049 | 34 |
| STV2049 ΔYALI0E25201 A | 67 |

Example 13. Over-Expression of the YALI0E25201 Transporter in Steviol Glycosides Producing *Y. lipolytica* Strains To further demonstrate the functionality of the YALI0E25201 transporter, the YALI0E25201 ORF was assembled in an expression cassette with the *Y. lipolytica* YP006 promoter and *Y. lipolytica* TEF4 terminator. The cassettes were assembled in the pRS417 5_3 vector together with the Nourseothricin marker. As a negative control the same cassette only containing the Nourseothricin marker was constructed. The expression cassettes were PCR amplified and the obtained fragments were transformed to three different strains: strains STV2049 is a strain producing mostly RebA, and is described above. Also, the transporter deletion strain is included (STV2049 ΔYALI0E25201 (described above)). The third strain is STV2170, a strain producing mostly RebM. STV2170 was build similarly to strain STV2049, and the genotype is listed below in Table 7.

TABLE 7

Genotype of strain STV2170. Between brackets indicates the gene copy number present in the strain

| Strain name | genotype |
|---|---|
| STV2170 | tHMG (2; SEQ ID NO: 15) GGS (2; SEQ ID NO: 16) CarG (1; SEQ ID NO: 32) CPS (2 SEQ ID NO: 20) |

TABLE 7-continued

Genotype of strain STV2170. Between brackets indicates
the gene copy number present in the strain

| Strain name | genotype |
|---|---|
| | KS (2; SEQ ID NO: 21) KO_Gib (2; SEQ ID NO: 23), KAH4 (4; SEQ ID NO: 22) CPR3 (2; SEQ ID NO: 24) UGT1 (5; SEQ ID NO: 17) UGT2_6b (2; SEQ ID NO: 33) UGT3 (2; SEQ ID NO: 18) UGT4 (4; SEQ ID NO: 19) RT18 (1; SEQ ID NO:34) |

Six transformants were selected for each combination of strain and expression cassette. The transformants were grown in 24-well fermentation and the supernatant- and pellet fractions were analyzed by LC-MS as described in Example 12.

TABLE 8

RebA supernatant and pellet concentrations in 24-well fermentations in the control strain (STV2049 with NatMX marker) and YALI0E25201 transporter over-expression strain (STV2049 with transporter and NatMX marker)

| Strain | RebA supernatant (mg/L) | RebA pellet (mg/L) |
|---|---|---|
| STV2049 control | 392 | 15 |
| YALI0E25201 O.E. | 461 | 15 |

These data illustrate that over-expression of the YALI0E25201 transporter has a positive effect on extracellular RebA production.

TABLE 9

RebM supernatant and pellet concentrations in 24-well fermentations in the control strain (STV2049 with NatMX marker) and YALI0E25201 transporter over-expression strain (STV2049 with transporter and NatMX marker)

| Strain | RebM supernatant (mg/L) | RebM pellet (mg/L) |
|---|---|---|
| STV2049 control | 59 | 10 |
| YALI0E25201 O.E. | 43 | 4 |

RebM production in this strain is low compared to RebA production, but even so, the effect of the transporter over-expression can be seen in the concentrations of RebM. As RebA is more efficiently exported to outside the cell in the YALI0E25201 over-expression strain, less RebA will be available for further glycosylation inside the cell, and hence resulting in lower production of RebM, particularly in the pellet fraction.

TABLE 10

RebA supernatant and pellet concentrations in 24-well fermentations in the transporter deletion strain (STV2049 ΔYALI0E25201 with NatMX marker) and the same background with the YALI0E25201 transporter over-expressed (STV2049 ΔYALI0E25201 with transporter and NatMX marker.)

| Strain | RebA supernatant (mg/L) | RebA pellet (mg/L) |
|---|---|---|
| STV2049 ΔYALI0E25201 control | 114 | 23 |
| STV2049 ΔYALI0E25201 YALI0E25201 O.E. | 431 | 17 |

Upon over-expression of the YALI0E25201 transporter in the YALI0E25201 deletion strain, the extracellular production of RebA is greatly enhanced, and restored to similar levels as the reference strain without the transporter deletion.

TABLE 11

RebM supernatant and pellet concentrations in 24-well fermentations in the transporter deletion strain (STV2049 ΔYALI0E25201 with NatMX marker) and the same background with the YALI0E25201 transporter over-expressed (STV2049 ΔYALI0E25201 YALI0E25201 O.E.)

| Strain | RebM supernatant (mg/L) | RebM pellet (mg/L) |
|---|---|---|
| STV2049 ΔYALI0E25201 control | 6 | 45 |
| STV2049 ΔYALI0E25201 YALI0E25201 O.E. | 22 | 1 |

In the transporter deletion strain, steviol glycosides including RebA accumulate in the cell, allowing for continued glycosylation inside the cell. As a consequence, RebM concentrations may increase. In the transporter deletion strain, the concentration RebM in the pellet fraction is much higher than in the supernatant. Upon restoring transport this is reversed: less accumulation of intracellular RebM, and more export of RebM.

TABLE 12

RebA supernatant and pellet concentrations in 24-well fermentations in the RebM production control strain (STV2170 with NatMX marker) and YALI0E25201 transporter over-expression strain (STV2170 with transporter and NatMX marker)

| Strain | RebA supernatant (mg/L) | RebA pellet (mg/L) |
|---|---|---|
| STV2170 control | 107 | 22 |
| STV2170 YALI0E25201 O.E. | 283 | 8 |

Over-expression of the YALI0E25201 transporter results in greatly increased extracellular production of RebA, and greatly reduced accumulation of RebA in the pellet.

TABLE 13

RebM supernatant and pellet concentrations in 24-well fermentations in the RebM production control strain (STV2170 with NatMX marker) and YALI0E25201 transporter over-expression strain (STV2170 with transporter and NatMX marker)

| Strain | RebM supernatant (mg/L) | RebM pellet (mg/L) |
|---|---|---|
| STV2170 control | 631 | 132 |
| STV2170 YALI0E25201 O.E. | 660 | 61 |

Over-expression of the YALI0E25201 transporter results in increased extracellular production of RebM, and reduced accumulation of RebM in the pellet.

Together these data illustrate that over-expression of the YALI0E25201 transporter has a positive effect on extracellular RebA and RebM production. Not only is the distribution of RebA and RebM production in the supernatant fraction versus the pellet fraction favourable when the transporter is over-expressed, over-expression of the YALI0E25201 transporter also has a positive effect on the total amount of RebA and RebM production.

TABLE 14

| SEQ ID NO | Description |
|---|---|
| SEQ ID NO: 1 | UGT2_1a CpO for Y. lipolytica |
| SEQ ID NO: 2 | PGM promoter from Y. lipolytica |
| SEQ ID NO: 3 | HSP promoter from Y. lipolytica |
| SEQ ID NO: 4 | HYPO promoter from Y. lipolytica |
| SEQ ID NO: 5 | ENO promoter from Y. lipolytica |
| SEQ ID NO: 6 | CWP promoter from Y. lipolytica |
| SEQ ID NO: 7 | TPI promoter from Y. lipolytica |
| SEQ ID NO: 8 | YP001 promoter from Y. lipolytica |
| SEQ ID NO: 9 | Xpr terminator from Y. lipolytica |
| SEQ ID NO: 10 | Cwp terminator from Y. lipolytica |
| SEQ ID NO: 11 | Gpd terminator from Y. lipolytica |
| SEQ ID NO: 12 | Pgm terminator from Y. lipolytica |
| SEQ ID NO: 13 | Pgk terminator from Y. lipolytica |
| SEQ ID NO: 14 | act1T terminator from Y. lipolytica |
| SEQ ID NO: 15 | tHMG CpO for Y. lipolytica |
| SEQ ID NO: 16 | GGS CpO for Y. lipolytica |
| SEQ ID NO: 17 | UGT1 CpO for Y. lipolytica |
| SEQ ID NO: 18 | UGT3 CpO for Y. lipolytica |
| SEQ ID NO: 19 | UGT4 CpO for Y. lipolytica |

TABLE 14-continued

| SEQ ID NO | Description |
|---|---|
| SEQ ID NO: 20 | tCPS from S. rebaudiana CpO for Y. lipolytica |
| SEQ ID NO: 21 | tKS from S. rebaudiana CpO for Y. lipolytica |
| SEQ ID NO: 22 | KAH_4 CpO for Y. lipolytica |
| SEQ ID NO: 23 | KO from Gibberella fujikori CpO for Y. lipolytica |
| SEQ ID NO: 24 | CPR_3 CpO for Y. lipolytica |
| SEQ ID NO: 25 | UGT2_10b CpO for Y. lipolytica |
| SEQ ID NO: 26 | YALI0C08701 WT CDS |
| SEQ ID NO: 27 | YALI0E25201 WT CDS |
| SEQ ID NO: 28 | YALI0E25201 CpO for Y. lipolytica |
| SEQ ID NO: 29 | YALI0E25201 WT from Y. lipolytica |
| SEQ ID NO: 30 | YP006 promoter from Y. lipolytica |
| SEQ ID NO: 31 | Tef4 terminator from Y. lipolytica |
| SEQ ID NO: 32 | CarG codon optimized for Y. lipolytica |
| SEQ ID NO: 33 | UGT2_6b CpO for Y. lipolytica |
| SEQ ID NO: 34 | RT18 CpO for Y. lipolytica |

The invention claimed is:

1. A recombinant cell capable of producing a steviol glycoside, which has been modified to reduce the expression of a polypeptide comprising the amino acid sequence of SEQ ID NO:29 or an amino acid sequence having at least 98% sequence identity to the amino acid sequence set forth in SEQ ID NO:29, as compared to a corresponding cell which has not been similarly modified.

2. The recombinant cell according to claim 1, which further comprises one or more recombinant nucleotide sequence(s) encoding:
   a polypeptide having ent-copalyl pyrophosphate synthase activity;
   a polypeptide having ent-Kaurene synthase activity;
   a polypeptide having ent-Kaurene oxidase activity; and
   a polypeptide having kaurenoic acid 13-hydroxylase activity.

3. The recombinant cell according to claim 1, which further comprises a recombinant nucleic acid sequence encoding a polypeptide having NADPH-cytochrome p450 reductase activity.

4. The recombinant cell according to claim 1, which further comprises a recombinant nucleic acid sequence encoding one or more of:
   (i) a polypeptide having UGT74G1 activity;
   (ii) a polypeptide having UGT2 activity;
   (iii) a polypeptide having UGT85C2 activity; and
   (iv) a polypeptide having UGT76G1 activity.

5. The recombinant cell according to claim 1, wherein the cell belongs to one of the genera *Saccharomyces, Aspergillus, Pichia, Kluyveromyces, Candida, Hansenula, Humicola, Issatchenkia, Trichosporon, Brettanomyces, Pachysolen, Yarrowia, Yamadazyma* or *Escherichia*.

6. The recombinant cell according to claim 5, wherein the recombinant cell is a *Saccharomyces cerevisiae* cell, a *Yarrowia lipolytica* cell, a *Candida krusei* cell, or an *Escherichia coli* cell.

7. The recombinant cell according to claim 1, wherein the ability of the cell to produce geranylgeranyl diphosphate (GGPP) is upregulated.

8. The recombinant cell according to claim 1, which further comprises a nucleic acid sequence encoding one or more of:
   a polypeptide having hydroxymethylglutaryl-CoA reductase activity; and
   a polypeptide having farnesyl-pyrophosphate synthetase activity.

9. A process for the preparation of a steviol glycoside, comprising fermenting the recombinant cell according to claim 1 in a suitable fermentation medium and, optionally, recovering the steviol glycoside.

10. The process according to claim 9 for the preparation of a steviol glycoside, wherein the process is carried out on an industrial scale.

11. A fermentation broth comprising the host according to claim 1.

* * * * *